US011559576B2

United States Patent
Bray et al.

(10) Patent No.: US 11,559,576 B2
(45) Date of Patent: Jan. 24, 2023

(54) ANTI-HUMAN PAPILLOMAVIRUS (HPV) ANTIGEN-BINDING PROTEINS AND METHODS OF USE THEREOF

(71) Applicant: Regeneron Pharmaceuticals, Inc., Tarrytown, NY (US)

(72) Inventors: Kevin A. Bray, Garnerville, NY (US); Frank Delfino, Poughquag, NY (US); Matthew C. Franklin, Great Neck, NY (US); Elena S. Garnova, White Plains, NY (US); Jessica Kirshner, New York, NY (US); Douglas MacDonald, New York, NY (US); William Olson, Yorktown Heights, NY (US); Gavin Thurston, Briarcliff Manor, NY (US)

(73) Assignee: Regeneran Pharmaceuticals, Inc., Tarrytown, NY (US)

(*) Notice: Subject to any disclaimer, the term of this patent is extended or adjusted under 35 U.S.C. 154(b) by 338 days.

(21) Appl. No.: 16/992,188

(22) Filed: Aug. 13, 2020

(65) Prior Publication Data
US 2022/0001000 A1    Jan. 6, 2022

Related U.S. Application Data

(62) Division of application No. 16/019,703, filed on Jun. 27, 2018, now Pat. No. 10,806,780.

(60) Provisional application No. 62/525,937, filed on Jun. 28, 2017.

(51) Int. Cl.
| | | |
|---|---|---|
| A61K 39/12 | (2006.01) | |
| C07K 16/28 | (2006.01) | |
| A61P 31/20 | (2006.01) | |
| A61P 35/00 | (2006.01) | |
| A61K 39/00 | (2006.01) | |
| C07K 16/08 | (2006.01) | |

(52) U.S. Cl.
CPC .......... *A61K 39/12* (2013.01); *A61K 39/0008* (2013.01); *A61K 39/0011* (2013.01); *A61P 31/20* (2018.01); *A61P 35/00* (2018.01); *C07K 16/084* (2013.01); *C07K 16/2809* (2013.01); *C07K 16/2833* (2013.01); *C07K 16/2875* (2013.01); *A61K 2039/545* (2013.01); *A61K 2039/572* (2013.01); *C07K 2317/32* (2013.01); *C07K 2317/92* (2013.01)

(58) Field of Classification Search
None
See application file for complete search history.

(56) References Cited

U.S. PATENT DOCUMENTS

| 9,453,075 B2 | 9/2016 | Cheung et al. |
| 10,806,780 B2 | 10/2020 | Bray et al. |
| 2016/0175358 A1 | 6/2016 | Jakobovits et al. |
| 2016/0311861 A1 | 10/2016 | Grabowska et al. |

FOREIGN PATENT DOCUMENTS

| CN | 105131113 A | 12/2015 |
| EP | 31215885 A1 | 6/2015 |
| WO | WO-2002/077012 A2 | 10/2002 |
| WO | WO-2010/027973 A1 | 3/2010 |
| WO | WO-2016/182957 A1 | 11/2016 |
| WO | WO-2018/067618 A1 | 4/2018 |

OTHER PUBLICATIONS

International Search Report and Written Opinion from PCT/US2018/039654 dated Nov. 7, 2018.
Riemer et al., "*A conserved E7-derived cytotoxic T lymphocyte epitope expressed on human papillomavirus 16-transformed HLA-A2+ epithelial cancers*", The Journal of Biological Chemistry, vol. 285(38), pp. 29608-29622, (2010).
Xu et al., "Ii-Key/HPV16 E7 hybrid peptide immunotherapy for HPV16+ cancers", Vaccine, vol. 27(34), pp. 4641-4647, (2009).
Bodmer et al., "Anti-HLA-A2 antibody-enhancement of peptide association with HLA-A2 as detected by cytotoxic T lymphocytes", Nature. Nov. 23, 1989;342(6248):443-6.
Youde et al., "Use of Fluorogenic Histocompatibility Leukocyte Antigen-A*0201/HPV 16 E7 Peptide Complexes to Isolate Rare Human Cytotoxic T-Lymphocyte—recognizing Endogenous Human Papillomavirus Antigens", Cancer Res. Jan. 15, 2000;60(2):365-71.
Albers et al., "Antitumor Activity of Human Papillomavirus Type 16 E7-Specific T Cells against Virally Infected Squamous Cell Carcinoma of the Head and Neck", Cancer Res. Dec. 1, 2005;65(23):11146-55.
Lybarger et al., "Enhanced Immune Presentation of a Single-chain Major Histocompatibility Complex Class I Molecule Engineered to Optimize Linkage of a C-terminally Extended Peptide", J Biol Chem. Jul. 18, 2003;278(29):27105-11.
Lybarger et al., "Single-Chain MHC Class I Molecules are Potent Stimulators of Specific CD8+ T Cells and Antibodies, and can Avoid Virus-Mediated Downregulation", FASEB 2002; 22 (1) Supplement; 240.2.
Hansen et al., "Translational and basic applications of peptide-MHCI Single chain trimers", Trends Immunol. Oct. 2010; 31(10): 363-369.
Truscott et al., "Disulfide Bond Engineering to Trap Peptides in the MHC Class I Binding Groove", J Immunol. May 15, 2007;178(10):6280-9.
Truscott et al., "Human Major Histocompatibility Complex (MHC) Class I Molecules with Disulfide Traps Secure Disease-related Antigenic Peptides and Exclude Competitor Peptides", J Biol Chem. Mar. 21, 2008;283(12):7480-90.

(Continued)

*Primary Examiner* — Agnieszka Boesen
(74) *Attorney, Agent, or Firm* — McCarter & English, LLP; Marcie B. J. Clarke D.; Deborah L. Nagle

(57) ABSTRACT

The present invention provides antigen-binding proteins that specifically bind to an HLA-displayed human papillomavirus (HPV) peptide, and therapeutic and diagnostic methods of using those binding proteins.

23 Claims, No Drawings
Specification includes a Sequence Listing.

(56) References Cited

OTHER PUBLICATIONS

Yu et al., "Cutting Edge: Single-Chain Trimers of MHC Class I Molecules Form Stable Structures That Potently Stimulate Antigen-Specific T Cells and B Cells", J Immunol. Apr. 1, 2002;168(7):3145-9.

Rosales et al., "Antibodies against human papillomavirus (HPV) type 16 and 18 E2, E6 and E7 proteins in sera: Correlation with presence of papillomavirus DNA", J. Med. Virol. 65:736-744, 2001.

Nilges, et al. "Human Papillomavirus Type 16 E7 Peptide-Directed CD8+ T Cells from Patients with Cervical Cancer are Cross-Reactive with the Coronavirus NS2 Protein," Journal of Virology. 2003.77:5464-5474.

ANTI-HUMAN PAPILLOMAVIRUS (HPV) ANTIGEN-BINDING PROTEINS AND METHODS OF USE THEREOF

RELATED APPLICATIONS

This application is a divisional of U.S. patent application Ser. No. 16/019,703, filed on Jun. 27, 2018, which claims priority to U.S. Provisional Application No. 62/525,937, filed on Jun. 28, 2017, the entire contents of which are expressly incorporated by reference herein in their entirety.

SEQUENCE LISTING

The instant application contains a Sequence Listing which has been filed electronically in ASCII format and is hereby incorporated by reference in its entirety. Said ASCII copy, created on Aug. 7, 2020, is named 118003_28903_SL.txt and is 253,645 bytes in size.

FIELD OF THE INVENTION

The present invention is related to antigen-binding proteins that specifically bind to an HLA-displayed human papillomavirus (HPV) peptide, and therapeutic and diagnostic methods of using those binding proteins.

BACKGROUND OF THE INVENTION

Human papillomavirus (HPV) is a group of small, non-enveloped DNA viruses that are extremely common worldwide. HPV is mainly transmitted through sexual contact and most people are infected with HPV shortly after the onset of sexual activity.

There are more than 170 types of HPV, some of which can cause warts or benign papillomas, and others, at least 13 of which, cause cancer (also known as high risk type HPVs), including cervical cancer, anogenital cancers (cancers of the anus, penis, vagina and vulva), head/neck cancers, and oropharynx cancers, including the back of the throat, the base of the tongue, and tonsils. Indeed, HPV is present in 20-40% of all head and neck squamous cell carcinomas (HNSCC) and in 100% of cervical cancers.

Cervical cancer is the second most common cancer in women living in less developed regions with an estimated 445,000 new cases in 2012 (84% of the new cases worldwide). In 2012, approximately 270,000 women died from cervical cancer; more than 85% of these deaths occurring in low- and middle-income countries.

Two HPV types (16 and 18) cause approximately 70% of all cervical cancers and precancerous cervical lesions. Cancer development upon persistent infection with a high risk HPV subtype, such as HPV 16 or 18, is mainly attributable to the expression of two viral oncoproteins, E6 and E7, which are continuously expressed in lesions and presented on the cell surface by MHC class I, but are not expressed in normal cells. E6 and E7 promote genomic instability and cellular transformation by degrading the tumor suppressors p53 and Rb in a proteasome-dependent manner. Tumors arise several years after the initial cellular immortalizing events and the continuous expression of E6 and E7 is required for maintenance of the transformed phenotype, and prevention of cell growth arrest and/or apoptosis (McLaughlin-Drubin M. E. & Miinger K., *Virology* (2009) 384:335-344).

Although vaccines targeting the HPV L1 and L2 major capsid proteins of HPV-6, -11, -16 and -18 subtypes have been developed to prevent infection, such vaccines cannot treat subjects having established lesions. Thus, the treatment of subjects having cervical cancer remains the use of traditional approaches which are highly invasive and morbid, such as surgery, radiotherapy, and chemotherapy. Furthermore, although such treatments may provide benefit for subjects having early stage cervical cancer, they are of limited value to patients with advanced or recurrent cervical cancer.

Accordingly, there is an unmet need in the art for new therapeutic strategies to target HPV with high specificity and to treat cervical cancer and other cancers caused by HPV.

BRIEF SUMMARY OF THE INVENTION

The present invention provides antigen-binding proteins that specifically bind to a conformational epitope of an HLA-displayed human papillomavirus (HPV) 16 E7 peptide (HLA-A2:HPV16E7). The antigen-binding proteins of the present invention bind with a high degree of specificity to HLA-displayed HPV16E7 and do not bind to HLA-displayed peptides that differ by 1, 2, 3, 4, 5 or more amino acids. The antigen-binding proteins of the invention allow for specific targeting of HPV16E7 peptide-presenting cells (i.e., cells presenting on their surface an HPV16E7 peptide bound to an MHC molecule, e.g., HLA-A2), such as cancer cells expressing HPV16E7 and, in some embodiments, stimulating T cell activation, e.g., to stimulate T cell-mediated killing of such cells. Furthermore, when fused to a detectable moiety, the antigen-binding proteins of the present invention allow for diagnosis and prognosis of HPV16E7-positive diseases or disorders with high sensitivity to changes in the number and distribution of HPV16E7 peptide-presenting cells, a more relevant measure of disease progression than circulating HPV16E7 levels.

The antigen-binding proteins of the invention may be antibodies, such as full-length (for example, an IgG1 or IgG4 antibody) antibodies, or may comprise only an antigen-binding portion of an antibody (for example, a Fab, F(ab)$_2$ or scFv fragment), and may be modified to affect functionality, e.g., to eliminate residual effector functions (Reddy et al., 2000, *J. Immunol.* 164:1925-1933). In some embodiments, the antigen-binding proteins of the invention may be antibodies, or antigen-binding fragments thereof. In certain embodiments, the antigen-binding proteins may be bispecific.

In a first aspect, the present invention provides isolated recombinant antigen-binding proteins that bind specifically to a conformational epitope of an HLA-displayed human papillomavirus (HPV) 16 E7 peptide, such as a HLA-displayed peptide comprising amino acid residues 11-19 or 82-90 of HPV16E7. In certain embodiments, the antigen-binding proteins are antibodies. In some embodiments, the antibodies are fully human.

Exemplary anti-HLA-A2:HPV16E7 antigen-binding proteins of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-HLA-A2:HPV16E7 antibodies. Table 2 sets forth the nucleic acid sequence identifiers of the HCVRs, LCVRs, HCDR1, HCDR2 HCDR3, LCDR1, LCDR2 and LCDR3 of the exemplary anti-HLA-A2:HPV16E7 antibodies.

The present invention provides antigen-binding proteins comprising an HCVR comprising an amino acid sequence selected from any of the HCVR amino acid sequences listed in Table 1, or a substantially similar sequence thereof having at least 90%, at least 95%, at least 96%, at least 97%, at least 98% or at least 99% sequence identity thereto.

The present invention also provides antigen-binding proteins comprising an LCVR comprising an amino acid sequence selected from any of the LCVR amino acid sequences listed in Table 1, or a substantially similar sequence thereof having at least 90%, at least 95%, at least 96%, at least 97%, at least 98% or at least 99% sequence identity thereto.

The present invention also provides antigen-binding proteins comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antigen-binding proteins comprising an HCVR/LCVR amino acid sequence pair contained within any of the exemplary anti-HLA-A2:HPV16E7 antigen-binding proteins listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530. In certain embodiments, the HCVR/LCVR amino acid sequence pair is selected from one of SEQ ID NOs: 2/10 (e.g., H4sH17364N), 34/42 (e.g., H4sH17670P), 82/90 (e.g., H4sH17675P), 194/202 (e.g., H4sH17930N2), 282/290 (e.g., H4sH21064P), and 506/514 (e.g., H4sH17363N).

In certain embodiments, the present invention provides anti-HLA-A2:HPV16E7 antigen-binding proteins comprising a HCVR and a LCVR, said HCVR comprising an amino acid sequence listed in Table 1 having no more than five amino acid substitutions, and said LCVR comprising an amino acid sequence listed in Table 1 having no more than five amino acid substitutions. For example, the present invention provides anti-HLA-A2:HPV16E7 antigen-binding proteins comprising a HCVR and a LCVR, said HCVR comprising an amino acid sequence of SEQ ID NO: 194 having no more than five amino acid substitutions, and said LCVR comprising an amino acid sequence of SEQ ID NO: 202 having no more than five amino acid substitutions. In another exemplary embodiment, the present invention provides anti-HLA-A2:HPV16E7 antigen-binding proteins comprising a HCVR and a LCVR, said HCVR comprising an amino acid sequence of SEQ ID NO: 194 having at least one amino acid substitution, and said LCVR comprising an amino acid sequence of SEQ ID NO: 202 having at least one amino acid substitution.

The present invention also provides antigen-binding proteins comprising a heavy chain CDR1 (HCDR1) comprising an amino acid sequence selected from any of the HCDR1 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a heavy chain CDR2 (HCDR2) comprising an amino acid sequence selected from any of the HCDR2 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a heavy chain CDR3 (HCDR3) comprising an amino acid sequence selected from any of the HCDR3 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a light chain CDR1 (LCDR1) comprising an amino acid sequence selected from any of the LCDR1 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a light chain CDR2 (LCDR2) comprising an amino acid sequence selected from any of the LCDR2 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a light chain CDR3 (LCDR3) comprising an amino acid sequence selected from any of the LCDR3 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a HCDR3 and a LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antigen-binding proteins, comprising an HCDR3/LCDR3 amino acid sequence pair contained within any of the exemplary anti-HLA-A2:HPV16E7 antigen-binding proteins listed in Table 1. In certain embodiments, the HCDR3/LCDR3 amino acid sequence pair is selected from the group consisting of SEQ ID NOs: 8/16 (e.g., H4sH17364N), 40/48 (e.g., H4sH17670P), 88/96 (e.g., H4sH17675P), 200/208 (e.g., H4sH17930N2), 288/296 (e.g., H4sH21064P), and 512/520 (e.g., H4sH17363N).

The present invention also provides antigen-binding proteins comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antigen-binding proteins comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides anti-HLA-A2:HPV16E7 antigen-binding proteins comprising a HCVR and a LCVR, said HCVR comprising HCDR1 comprising an amino acid sequence of SEQ ID NO: 196 or an amino acid sequence differing from SEQ ID NO: 196 by 1 amino acid, HCDR2 comprising an amino acid sequence of SEQ ID NO: 198 or an amino acid sequence differing from SEQ ID NO: 198 by 1 amino acid, and HCDR3 comprising an amino acid sequence of SEQ ID NO: 200 or an amino acid sequence differing from SEQ ID NO: 200 by 1 amino acid. In another exemplary embodiment, the present invention provides antigen-binding proteins comprising a HCVR and a LCVR, said LCVR comprising LCDR1 comprising an amino acid sequence of SEQ ID NO: 204 or an amino acid sequence differing from SEQ ID NO: 204 by 1 amino acid, LCDR2 comprising an amino acid sequence of SEQ ID NO: 206 or an amino acid sequence differing from SEQ ID NO: 206 by 1 amino acid, and LCDR3 comprising an amino acid sequence of SEQ ID NO: 208 or an amino acid sequence differing from SEQ ID NO: 208 by 1 amino acid.

The present invention also provides antigen-binding proteins comprising a set of six CDRs HCDR1-HCDR2-HCDR3-LCDR1-LCDR2-LCDR3) contained within any of the exemplary antigen-binding proteins listed in Table 1. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., H4sH17364N), 36-38-40-44-46-48 (e.g., H4sH17670P), 84-86-88-92-94-96 (e.g., H4sH17675P), 196-198-200-204-206-208 (e.g., H4sH17930N2), 284-286-288-292-294-296 (e.g., H4sH21064P), and 508-510-512-516-518-520 (e.g., H4sH17363N).

In a related embodiment, the present invention provides antigen-binding proteins comprising a set of six CDRs HCDR1-HCDR2-HCDR3-LCDR1-LCDR2-LCDR3) contained within an HCVR/LCVR amino acid sequence pair as defined by any of the exemplary antigen-binding proteins listed in Table 1. For example, the present invention includes antigen-binding proteins comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H4sH17364N), 34/42 (e.g., H4sH17670P), 82/90 (e.g., H4sH17675P), 194/202 (e.g., H4sH17930N2), 282/290 (e.g., H4sH21064P), and 506/514 (e.g., H4sH17363N).

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antigen-binding protein.

The present invention includes anti-HLA-A2:HPV16E7 antigen-binding proteins having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) *JBC* 277:26733). In other applications, modification of galactosylation can be made in order to modify complement dependent cytotoxicity (CDC).

In certain embodiments, the antigen-binding proteins of the invention are monoclonal antibodies comprising a HCVR and a LCVR amino acid sequence pair (HCVR/LCVR) comprising any of the HCVR amino acid sequences listed in Table 1 paired with any of the LCVR amino acid sequences listed in Table 1. In certain embodiments, the monoclonal antibodies comprise a Fc domain of an isotype selected from the group consisting of IgA, IgD, IgE, IgG, IgG1, IgG2, IgG3, IgG4, IgM and a variant thereof.

The present invention provides antigen-binding proteins, or antigen-binding fragments thereof, comprising a heavy chain comprising an amino acid sequence selected from any of the HC amino acid sequences listed in Table 3, or a substantially similar sequence thereof having at least 90%, at least 95%, at least 98% or at least 99% sequence identity thereto.

The present invention also provides antigen-binding proteins, or antigen-binding fragments thereof, comprising a light chain comprising an amino acid sequence selected from any of the LC amino acid sequences listed in Table 3, or a substantially similar sequence thereof having at least 90%, at least 95%, at least 98% or at least 99% sequence identity thereto.

The present invention also provides antigen-binding proteins, or antigen-binding fragments thereof, comprising a HC and a LC amino acid sequence pair (HC/LC) comprising any of the HC amino acid sequences listed in Table 3 paired with any of the LC amino acid sequences listed in Table 3. According to certain embodiments, the present invention provides antibodies, or antigen-binding fragments thereof, comprising an HC/LC amino acid sequence pair contained within any of the exemplary anti-PD-1 antibodies listed in Table 3. In certain embodiments, the HC/LC amino acid sequence pair is selected from the group consisting of SEQ ID NOs: 578/579, 580/581, 582/583, 584/585, 586/587, 588/589, 590/591, and 592/593.

In one aspect, the present invention provides antigen-binding proteins or antigen-binding fragments thereof that bind to a HLA-peptide complex wherein the antigen-binding protein or antigen-binding fragment thereof contacts at least 60%, at least 70%, at least 80% or at least 90% of the amino acid residues of the peptide that is comprised in the HLA-peptide complex. In certain embodiments, the antigen-binding protein or antigen-binding fragment thereof "covers" or contacts all of the amino acid residues of the peptide comprised in the HLA-peptide complex. In certain embodiments, the antigen-binding protein or antigen-binding fragment thereof binds to a HLA-peptide complex with high affinity and specificity, wherein the antigen-binding protein or antigen-binding fragment thereof contacts the entire length of the displayed peptide. "Contact", as used herein includes direct or water-mediated hydrogen bonds, charge-charge interactions, or hydrophobic/van der Waals interactions. In one embodiment, the antigen-binding protein or antigen-binding fragment thereof binds to HLA-A2-HPV16E7 11-19 peptide complex wherein the antigen-binding protein binds to at least 6 of 10 amino acid residues of peptide 11-19 (SEQ ID NO: 538) and to HLA-A2 such that it covers the HLA-A2-peptide complex completely. In certain embodiments, the antigen-binding protein or antigen-binding fragment thereof comprises the CDRs of a HCVR and the CDRs of a LCVR, wherein the HCVR and LCVR each has an amino acid sequence selected from the HCVR and LCVR sequences listed in Table 1. In one embodiment, the antigen-binding protein is fully human. In certain embodiments, the fully human antigen-binding proteins are not obtained using phage display methods and technologies. In one embodiment, the antigen-binding proteins comprise a light chain variable region of the IGKV1-39 sub-type.

In certain embodiments, the present invention provides antigen-binding proteins or antigen-binding fragments thereof that bind to HLA-A2:HPV16E7 11-19 peptide, wherein the antigen-binding protein binds to one or more amino acids of SEQ ID NO: 538. In one embodiment, the antigen-binding protein binds to at least 6 amino acids of SEQ ID NO: 538. In one embodiment, the antigen-binding protein binds to one or more amino acids selected from the group consisting of Y11, D14, L15, P 17 and E18 of SEQ ID NO: 538.

In certain embodiments, the present invention provides antigen-binding protein that binds specifically to a conformational epitope of an HLA-A2 presented human papillomavirus (HPV) 16 E7 peptide (HPV16E7 peptide), wherein the conformational epitope comprises one or more amino acids of SEQ ID NO: 538. In the certain embodiments, the conformational epitope comprises one or more amino acids selected from the group consisting of Y11, D14, L15, P 17 and E18 of SEQ ID NO: 538.

The present invention also provides for antigen-binding proteins that compete for specific binding to HLA-A2:HPV16E7 with an antigen-binding protein comprising the CDRs of a HCVR and the CDRs of a LCVR, wherein the HCVR and LCVR each has an amino acid sequence selected from the HCVR and LCVR sequences listed in Table 1.

The present invention also provides antigen-binding proteins that cross-compete for binding to HLA-A2:HPV16E7 with a reference antigen-binding protein comprising the CDRs of a HCVR and the CDRs of a LCVR, wherein the HCVR and LCVR each has an amino acid sequence selected from the HCVR and LCVR sequences listed in Table 1.

The present invention also provides antigen-binding proteins that bind to the same epitope as a reference antigen-binding protein comprising the CDRs of a HCVR and the CDRs of a LCVR, wherein the HCVR and LCVR each has an amino acid sequence selected from the HCVR and LCVR sequences listed in Table 1. In certain embodiments, the present invention provides antigen-binding proteins that bind to the same epitope as a reference antigen-binding protein comprising the CDRs of a HCVR and the CDRs of a LCVR, wherein the HCVR is selected from the group consisting of SEQ ID NOs: 2, 34, 82, 194, 282 and 504, and the LCVR is selected from the group consisting of SEQ ID Nos: 10, 42, 90, 202, 290 and 514.

In one embodiment, the invention provides a recombinant isolated antigen-binding protein that binds specifically to a conformational epitope of an HLA-A2 presented human papillomavirus (HPV) 16 E7 peptide (HPV16E7 peptide), wherein the antigen-binding protein has a property selected from the group consisting of: (a) binds monomeric HLA-A2:HPV16E7 11-19 peptide with a binding dissociation equilibrium constant ($K_D$) of less than about 20 nM as measured in a surface plasmon resonance assay at 25° C.; (b) binds monomeric HLA-A2:HPV16E7 82-90 peptide with a binding dissociation equilibrium constant ($K_D$) of less than about 25 nM as measured in a surface plasmon resonance assay at 25° C.; (c) binds to HLA-A2:HPV16E7 11-19 peptide expressing cells with an $EC_{50}$ less than about 6 nM and does not bind to cells expressing predicted off-target peptides as determined by luminescence assay; (d) binds to HLA-A2:HPV16E7 82-90 peptide expressing cells with an $EC_{50}$ less than about 1 nM and do not substantially bind to cells expressing predicted off-target peptides as determined by luminescence assay; (e) binds to HLA-A2:HPV16E7 11-19 peptide expressing cells with an $EC_{50}$ less than about 30 nM as determined by flow cytometry assay; (f) binds to HLA-A2:HPV16E7 82-90 peptide expressing cells with an $EC_{50}$ less than about 75 nM as determined by flow cytometry assay; and (g) the conformational epitope comprises one or more amino acids of SEQ ID NO: 538. As disclosed elsewhere herein, an "off-target peptide" refers to a peptide that differs by 1, 2, 3, 4, 5 or more amino acids from a target peptide (e.g., HPV16 E7 11-19 peptide).

In a second aspect, the present invention provides nucleic acid molecules encoding anti-HLA-A2:HPV16E7 antigen-binding proteins. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-HLA-A2:HPV16E7 antigen-binding proteins listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-HLA-A2:HPV16E7 antigen-binding proteins listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 96%, at least 97%, at least 98% or at least 99% sequence identity thereto. In certain embodiments according to this aspect of the invention, the nucleic acid molecule encodes an HCVR and LCVR, wherein the HCVR and LCVR are both derived from the same anti-HLA-A2:HPV16E7 antigen-binding protein listed in Table 1.

The present invention provides nucleic acid molecules encoding any of the heavy chain amino acid sequences listed in Table 3. The present invention also provides nucleic acid molecules encoding any of the light chain amino acid sequences listed in Table 3.

The present invention also provides nucleic acid molecules encoding both heavy chain (HC) and a light chain (LC), wherein the HC comprises an amino acid sequence of any of the HC amino acid sequences listed in Table 3, and wherein the LC comprises an amino acid sequence of any of the LC amino acid sequences listed in Table 3.

In a related aspect, the present invention provides recombinant expression vectors capable of expressing a polypeptide comprising a heavy and/or or light chain variable region of an anti-HLA-A2:HPV16E7 antigen-binding protein. For example, the present invention includes recombinant expression vectors comprising any of the nucleic acid molecules mentioned above, i.e., nucleic acid molecules encoding any of the HCVR, LCVR, and/or CDR sequences as set forth in Table 1. The present invention also provides recombinant expression vectors capable of expressing a polypeptide comprising a heavy and/or light chain of an anti-HLA-A2:HPV16E7 antigen-binding protein. For example, the present invention includes recombinant expression vectors comprising any of the nucleic acid molecules mentioned above, i.e., nucleic acid molecules encoding any of the heavy chain or light chain sequences as set forth in Table 2. Also included within the scope of the present invention are host cells into which such vectors have been introduced, as well as methods of producing the antigen-binding proteins by culturing the host cells under conditions permitting production of the antigen-binding proteins, and recovering the antigen-binding proteins so produced.

In a third aspect, the present invention provides a pharmaceutical composition comprising a therapeutically effective amount of a recombinant isolated antigen-binding protein that binds specifically to a conformational epitope of an HLA-A2 presented HPV16E7 peptide (e.g., a peptide comprising amino acid residues 11-19 or 82-90 of HPV16E7), and a pharmaceutically acceptable carrier. In a related aspect, the invention features a composition which is a combination of an anti-HLA-A2:HPV16E7 antigen-binding protein and a second therapeutic agent. In one embodiment, the second therapeutic agent is any agent that is advantageously combined with an anti-HLA-A2:HPV16E7 antigen-binding protein. Exemplary agents that may be advantageously combined with an anti-HLA-A2:HPV16E7 antigen-binding protein include, without limitation, other agents that bind and/or modulate HPV replication or infection (including other antibodies or antigen-binding fragments thereof, etc.) and/or agents which modulate immune cell activation. Additional therapies that can be used in combination with the anti-HLA-A2:HPV16E7 antigen-binding proteins of the present invention are disclosed elsewhere herein.

In a fourth aspect, the invention provides methods to treat a subject having an HPV-associated disease or disorder, such as an HPV16E7-positive cancer. The methods include administering a therapeutically effective amount of an anti-HLA-A2:HPV16E7 antigen-binding protein of the invention or a pharmaceutical composition of the invention to the subject in need thereof. The disorder treated is any disease or condition which is improved, ameliorated, inhibited or prevented by the antigen-binding proteins and compositions provided herein. In certain embodiments, the antigen-binding protein (or pharmaceutical composition) of the invention is administered in combination with a second therapeutic agent to the subject in need thereof. The second therapeutic agent may be selected from the group consisting of an antibody to a T cell co-inhibitor, an antibody to a tumor cell antigen, an antibody to a T cell receptor, an antibody to an epitope on a virally infected cell, a cytotoxic agent, an anti-cancer drug, an anti-viral drug, an anti-inflammatory drug (e.g., corticosteroids), chemotherapeutic agent, surgery, radiation therapy, an immunosuppressant and any other drug or therapy known in the art. In certain embodiments, the second therapeutic agent may be an agent that helps to counteract or reduce any possible side effect(s) associated with antigen-binding protein of the invention, if such side effect(s) should occur.

In certain embodiments, the present invention provides methods for suppressing growth of a HPV-associated cancer. For example, the present invention provides methods to suppress tumor growth due to a primary tumor or a metastatic tumor in a subject. In certain embodiments, the present invention provides methods to enhance survival (e.g., progression-free survival or overall survival) of a subject with a HPV-associated cancer. Examples of cancer include, but are not limited to, squamous cell carcinomas, such as squamous cell carcinoma of head and neck, cervical cancer, anogenital cancer, oropharyngeal cancer.

In certain embodiments, the present invention provides methods for inhibiting or suppressing growth of established tumors. The methods comprise administering to a subject in need thereof a pharmaceutical composition comprising a therapeutically effective amount of an antigen-binding protein of the present invention. In certain embodiments, the antigen-binding protein is administered in combination with a second therapeutic agent.

The antigen-binding protein, e.g., antibody, or antigen-binding fragment thereof, may be administered subcutaneously, intravenously, intradermally, intraperitoneally, orally, intramuscularly, or intracranially. The antigen-binding protein, e.g., antibody or antigen-binding fragment thereof, may be administered at a dose of about 0.1 mg/kg of body weight to about 100 mg/kg of body weight of the subject.

In a fifth aspect, the present invention provides an isolated nucleic acid molecule encoding a chimeric antigen receptor (CAR). The CAR may include an extracellular binding domain that specifically binds to a conformational epitope of an HLA-A2 presented human papillomavirus (HPV) 16 E7 peptide (HPV16E7 peptide), e.g., amino acid residues 11-19 or 82-90 of HPV16E7, a transmembrane domain, and an intracellular signaling domain. In one embodiment, the extracellular binding domain is an anti-HLA-A2:HPV16E7 antigen-binding protein or an antigen-binding fragment thereof. Exemplary anti-HLA-A2:HPV16E7 antigen-binding proteins of the present invention are any of the antigen-binding proteins described herein.

For example, in certain embodiments, the antigen-binding protein suitable for use in the CARs of the invention comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In other embodiments, the antigen-binding protein suitable for use in the CARs of the invention comprises a HCVR having an amino acid sequence selected from the group consisting of HCVR sequences listed in Table 1; and/or a LCVR having an amino acid sequence selected from the group consisting of LCVR sequences listed in Table 1.

In some embodiments, the antigen-binding protein suitable for use in the CARs of the invention comprises (a) a HCVR having an amino acid sequence selected from the group consisting of HCVR sequences listed in Table 1; and (b) a LCVR having an amino acid sequence selected from the group consisting of LCVR sequences listed in Table 1.

In one embodiments, the antigen-binding protein suitable for use in the CARs of the invention comprises (a) a HCDR1 domain having an amino acid sequence selected from the group consisting of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524; (b) a HCDR2 domain having an amino acid sequence selected from the group consisting of SEQ ID NOs: 6, 22, 38, 54, 70, 86, 102, 118, 134, 150, 166, 182, 198, 214, 222, 238, 254, 270, 286, 302, 318, 334, 350, 366, 382, 398, 414, 430, 446, 462, 478, 494, 510, and 526; (c) a HCDR3 domain having an amino acid sequence selected from the group consisting of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528; (d) a LCDR1 domain having an amino acid sequence selected from the group consisting of SEQ ID NOs: 12, 28, 44, 60, 76, 92, 108, 124, 140, 156, 172, 188, 204, 228, 244, 260, 276, 292, 308, 324, 340, 356, 372, 388, 404, 420, 436, 452, 468, 484, 500, 516, and 532; (e) a LCDR2 domain having an amino acid sequence selected from the group consisting of SEQ ID NOs: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534; and (f) a LCDR3 domain having an amino acid sequence selected from the group consisting of SEQ ID NOs: 16, 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536.

In further embodiment, the antigen-binding protein suitable for use in the CARs of the invention comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530, such as an HCVR/LCVR amino acid sequence pair selected from the group consisting of SEQ ID NOs: 2/10, 34/42, 82/90, 194/202, 282/290, and 506/514.

In some embodiments the isolated antigen-binding protein for use in the CARs of the present invention is an scFv.

In other aspects, the present invention provides vectors comprising the isolated CAR nucleic acid molecules; and immune effector cells comprising such vectors.

In yet other aspects of the present invention, methods for treating a subject having a HPV-associated disease or disorder, such as an HPV16E7-positive cancer, e.g., squamous cell carcinoma, e.g., cervical cancer, head and neck small cell carcinoma, anogenital cancer, and oropharyngeal cancer are provided. The methods include administering to the subject a population of immune effector cells comprising a CAR of the invention.

In some aspects, the present invention provides methods for detecting HPV16E7-positive cells, e.g., in a subject or in a sample obtained from a subject. The methods include contacting a cell, such as a cell sample obtained from a subject, or administering to a subject, an antigen-binding protein of the invention comprising a detectable moiety, and detecting the presence of the detectable moiety.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "human papilloma virus" ("HPV") refers to a small, non-enveloped deoxyribonucleic acid (DNA) virus that infects skin or mucosal cells. The circular, double-stranded viral genome is approximately 8-kb in length. The genome encodes for 6 early proteins responsible for virus replication and 2 late proteins, L1 and L2, which are the viral structural proteins. There are over 170 types of HPV that have been identified, and they are designated by numbers. Some HPV types, such as HPV-5, may establish infections that persist for the lifetime of the individual without ever manifesting any clinical symptoms. HPV types 1 and 2 can cause common warts in some infected individuals. HPV types 6 and 11 can cause genital warts and respiratory papillomatosis. HPV types 16, 18, 31, 33, 35, 39, 45, 51, 52, 56, 58, 59, 68, 73, and 82 are considered carcinogenic.

The term "HPV16E7" refers to the HPV type 16 early gene, designated E7, and the protein translated from the gene.

The amino acid sequence of full-length HPV16E7 is provided in GenBank as accession number NP_041326.1 (SEQ ID NO: 537). The term "HPV16E7" includes recombinant HPV16E7 or a fragment thereof. The term also encompasses HPV16E7 or a fragment thereof coupled to, for example, histidine tag, mouse or human Fc, or a signal sequence such as ROR1. In certain embodiments, the term comprises HPV16E7 or a fragment thereof in the context of HLA-A2, linked to HLA-A2 or as displayed by HLA-A2.

The term "HLA" refers to the human leukocyte antigen (HLA) system or complex, which is a gene complex encoding the major histocompatibility complex (MHC) proteins in humans. These cell-surface proteins are responsible for the regulation of the immune system in humans. HLAs corresponding to MHC class I (A, B, and C) present peptides from inside the cell.

The term "HLA-A" refers to the group of human leukocyte antigens (HLA) that are coded for by the HLA-A locus. HLA-A is one of three major types of human MHC class I cell surface receptors. The receptor is a heterodimer, and is composed of a heavy α chain and smaller β chain. The α chain is encoded by a variant HLA-A gene, and the β chain (β2-microglobulin) is an invariant β2 microglobulin molecule.

The term "HLA-A2" is one particular class I major histocompatibility complex (MHC) allele group at the HLA-A locus; the α chain is encoded by the HLA-A*02 gene and the β chain is encoded by the β2-microglobulin or B2M locus.

The term "antigen-binding protein," "binding protein" or "binding molecule," as used herein includes molecules that contain at least one antigen-binding site that specifically binds to a molecule of interest, such as a conformational epitope of an HLA-A2 presented human papillomavirus (HPV) 16 E7 peptide (HPV16E7 peptide), e.g., a HLA-A2-displayed peptide comprising amino acid residues 11-19 or 82-90. A binding protein may be an antibody, such as a full-length antibody, or an antigen-binding fragment of an antibody, or a chimeric antigen receptor (CAR), or any other polypeptide, e.g., a receptor-antibody (Rab) protein.

The term "HLA-A2:HPV16E7 antigen-binding protein" or "HLA-A2:HPV16E7 antigen-binding protein," or the like, refers to the an antigen-binding protein, such as an antibody, or antigen-binding portion thereof, that specifically binds to a conformational epitope by the presentation of a peptide fragment of HPV16E7, e.g., amino acid residues 11-19 or amino acid residues 82-90), by HLA-A2. In certain embodiments, the conformational epitope is created on the surface of a cell by the HLA-A2-presented HPV16E7 peptide.

The term "epitope" refers to an antigenic determinant that interacts with a specific antigen-binding site in the variable region of an antigen-binding protein known as a paratope. A single antigen may have more than one epitope. Thus, different antigen-binding proteins may bind to different areas on an antigen and may have different biological effects. The term "epitope" also refers to a site on an antigen to which B and/or T cells respond. It also refers to a region of an antigen that is bound by an antigen-binding protein. Epitopes may be defined as structural or functional. Functional epitopes are generally a subset of the structural epitopes and have those residues that directly contribute to the affinity of the interaction. Epitopes may also be "conformational," that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In some embodiments of the invention, a binding protein is an antibody, or an antigen-binding fragment thereof, such as a full-length antibody, or antigen-binding fragment thereof.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen-binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antigen binding proteins, such as antibodies, have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The anti-HLA-A2:HPV16E7 antigen-binding proteins, e.g., fully human anti-HLA-A2:HPV16E7 monoclonal antibodies, or antigen-binding fragments thereof, or CARs, disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antigen-binding proteins, e.g., antibodies, or antigen-binding fragments thereof, or CARs, which are derived from any of the amino acid sequences disclosed herein, wherein one or more amino acids within one or more framework and/or CDR regions are mutated to the corresponding residue(s) of the germline sequence from which the antigen-binding protein was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antigen-binding proteins, e.g., antibodies, or antigen-binding fragments thereof, or CARs, which comprise one or more individual germline mutations or combinations thereof. In certain embodiments, all of the framework and/or CDR residues within the $V_H$ and/or $V_L$ domains are mutated back to the residues found in the original germline sequence from which the antigen-binding protein, e.g., antibody, was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antigen-binding proteins, e.g., antibodies, or antigen-binding fragments thereof, or CARs, of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding proteins, e.g., antibodies and antigen-binding fragments, that contain one or more germline mutations can be easily tested for one or more desired property such as, improved binding specificity, increased binding affinity, improved or enhanced antagonistic or agonistic biological properties (as the case may be), reduced immunogenicity, etc. Antigen binding proteins, e.g., antibodies, or antigen-binding fragments thereof, or CARs, obtained in this general manner are encompassed within the present invention.

The present invention also includes antigen-binding proteins, e.g., fully human anti-HLA-A2:HPV16E7 monoclonal antibodies, or antigen-binding fragments thereof, or CARs, comprising variants of any of the HCVR, LCVR, and/or CDR amino acid sequences disclosed herein having one or more conservative substitutions. For example, the present invention includes anti-HLA-A2:HPV16E7 antigen-binding proteins having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human monoclonal antibodies (mAbs) of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antigen-binding proteins, e.g., antibodies or antigen-binding fragments thereof, of the invention created, expressed, isolated or obtained by technologies or methods known in the art as recombinant DNA technology which include, e.g., DNA splicing and transgenic expression. The term refers to antigen-binding proteins, e.g., antibodies expressed in a non-human mammal (including transgenic non-human mammals, e.g., transgenic mice), or a cell (e.g., CHO cells) expression system or isolated from a recombinant combinatorial human antibody library.

As used herein, the terms "chimeric antigen receptor" or "CAR", used interchangeably herein, refer to a recombinant fused protein comprising an extracellular domain capable of binding to an antigen (e.g., a conformational epitope of an HLA-A2 displayed HPV16E7 peptide, e.g., a peptide comprising amino acid residues 11-19 or 82-90 of HPV16E7), a transmembrane domain, and at least one intracellular signaling domain.

An "immune effector cell," as used herein, refers to any cell of the immune system that has one or more effector functions (e.g., cytotoxic cell killing activity, secretion of cytokines, induction of ADCC and/or CDC). In one embodiment, the immune effector cells used with the CARs as described herein are T lymphocytes, in particular cytotoxic T cells (CTLs; CD8+ T cells) and helper T cells (HTLs; CD4+ T cells). Other populations of T cells are also useful herein, for example naïve T cells and memory T cells. As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in this regard, immune effector cell includes progenitors of immune effectors cells such as hematopoietic stem cells (HSCs) contained within the CD34+ population of cells derived from cord blood, bone marrow or mobilized peripheral blood which upon administration in a subject differentiate into mature immune effector cells, or which can be induced in vitro to differentiate into mature immune effector cells.

As disclosed herein, the term "off-target peptide" refers to a peptide that differs by 1, 2, 3, 4, 5 or more amino acids from a target peptide (e.g., HPV16 E7 11-19 peptide). In certain embodiments, the term includes a peptide that differs by less than or equal to 3 amino acids than the target peptide. For example, for a 9-mer peptide, if 1, 2, or 3 amino acids are not identical to the target peptide, it is considered an "off-target" peptide. In certain embodiments, amino acid identity is expressed in terms of 'degree of similarity' (DoS). If 6 or more amino acids within a 9-mer peptide are identical, the DoS is 6. In certain embodiments, a peptide with DoS≤6 is considered an "off-target" peptide. The term "off-target" peptide also refers to a peptide that is similar to the target peptide based on sequence homology, is predicted to bind to HLA-A2 and is comprised in a protein that is expressed in essential, normal tissues.

The term "specifically binds," or "binds specifically to", or the like, means that an antigen-binding protein, e.g., antibody, or antigen-binding fragments thereof, or CAR, forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antigen-binding proteins, e.g., antibodies, have been identified by surface plasmon resonance, e.g., BIACORE™, which bind specifically to a conformational epitope of an HLA-A2 presented human papillomavirus (HPV) 16 E7 peptide (HPV16E7 peptide), e.g., a peptide comprising amino acid residues 11-19 or 82-90 of HPV16E7.

The term "high affinity" antigen-binding protein, e.g., antibody, refers to those antigen-binding proteins, e.g., mAbs, having a binding affinity to conformational epitope of an HLA-A2 presented HPV16E7 peptide, e.g., a peptide comprising amino acid residues 11-19 or 82-90 of HPV16E7, expressed as $K_D$, of at least $10^{-8}$ M; preferably $10^{-9}$M; more preferably $10^{-10}$M; even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antigen-binding protein that dissociates from HLA-A2:HPV16E7, with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antigen-binding protein (e.g., antibody), "antigen-binding fragment" of an antigen-binding protein (e.g., antibody), and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to conformational epitope of an HLA-A2 presented HPV16E7 peptide, e.g., a peptide comprising amino acid residues 11-19 or 82-90 of HPV16E7 coupled to HLA-A2.

In specific embodiments, antigen-binding proteins, e.g., antibody or antibody fragments, or CARs, of the invention may be conjugated to a moiety such as a ligand, a detectable moiety, or a therapeutic moiety ("immunoconjugate"), such as a cytotoxin, a second anti-HLA-A2:HPV16E7 antigen-binding protein, an antibody to a tumor-specific antigen, an anti-cancer drug, or any other therapeutic moiety useful for treating a disease or condition including HPV-associated disease or disorder, such as an HPV16E7-positive cancer or HPV infection including chronic HPV infection.

An "isolated antigen-binding protein", e.g., an isolated antibody, as used herein, is intended to refer to an antigen-binding protein, e.g., antibody, that is substantially free of other antigen-binding proteins, e.g., antibodies (Abs), having different antigenic specificities (e.g., an isolated antibody that specifically binds HLA-A2:HPV16E7, or a fragment thereof, is substantially free of antigen-binding proteins, e.g., antibodies, that specifically bind antigens other than a conformational epitope of an HLA-A2 presented HPV16E7 peptide.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antigen-binding protein-antigen interaction.

The term "cross-competes", as used herein, means an antigen-binding protein, e.g., antibody or antigen-binding fragment thereof, binds to an antigen and inhibits or blocks the binding of another antigen-binding protein, e.g., antibody or antigen-binding fragment thereof. The term also includes competition between two antigen-binding proteins, e.g., antibodies, in both orientations, i.e., a first antigen-binding protein, e.g., antibody, that binds and blocks binding of second antigen-binding protein, e.g., antibody, and vice-versa. In certain embodiments, the first antigen-binding protein, e.g., antibody, and second antigen-binding protein, e.g., antibody, may bind to the same epitope. Alternatively, the first and second antigen-binding proteins, e.g., antibodies, may bind to different, but overlapping epitopes such that binding of one inhibits or blocks the binding of the second, e.g., via steric hindrance. Cross-competition between antigen-binding proteins, e.g., antibodies, may be measured by methods known in the art, for example, by a real-time, label-free bio-layer interferometry assay. Cross-competition between two antigen-binding proteins, e.g., antibodies, may be expressed as the binding of the second antigen-binding protein, e.g., antibody, that is less than the background signal due to self-self binding (wherein first and second antigen-binding proteins, e.g., antibodies, is the same antigen-binding protein, e.g., antibody). Cross-competition between 2 antigen-binding proteins, e.g., antibodies, may be expressed, for example, as % binding of the second antigen-binding protein, e.g., antibody, that is less than the baseline self-self background binding (wherein first and second antigen-binding proteins, e.g., antibodies is the same antigen-binding protein, e.g., antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, *J. Mol. Biol.* 48: 443-453) for global alignment, or the Smith Waterman algorithm (Smith and Waterman 1981, *J. Mol. Biol.* 147: 195-197) for local alignment. Another preferred algorithm is described by Dufresne et al in Nature Biotechnology in 2002 (vol. 20, pp. 1269-71) and is used in the software GenePAST (GQ Life Sciences, Inc. Boston, Mass.).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 96%, 97%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra).

Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215: 403-410 and (1997) *Nucleic Acids Res.* 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) *The Art, Science and Technology of Pharmaceutical Compounding*).

As used herein, the term "subject" refers to an animal, preferably a mammal, in need of amelioration, prevention and/or treatment of a disease or disorder such as HPV infection, or a HPV-associated disease or disorder, such as a HPV-associated cancer (e.g., an HPV16E7-positive cancer). The term includes human subjects who have or are at risk of having HPV-associated disease or disorder, such as an HPV-associated cancer, metastatic HPV-associated cancer or HPV infection.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug" includes, but is not limited to zidovudine, lamivudine, abacavir, ribavirin, lopinavir, efavirenz, cobicistat, tenofovir, rilpivirine, analgesics and corticosteroids.

An immunogen comprising any one of the following can be used to generate antigen-binding proteins, e.g., antibodies, to a conformational epitope of an HLA-A2 presented HPV16E7 peptide, e.g., a peptide comprising amino acid residues 11-19 or residues 82-90 of HPV16E7 linked to HLA-A2. In certain embodiments, the antigen-binding proteins, e.g., antibodies, of the invention are obtained from mice immunized with a full length native HPV16E7 protein (See NCBI accession number NP_041326.1) (SEQ ID NO: 537) or with a recombinant HPV16E7 peptide, such as a peptide comprising either amino acids residues 11-19 (YMLDLQPET; SEQ ID NO: 538) of GenBank Accession NP_041326.1 (SEQ ID NO: 537) or amino acid residues 82-90 (LLMGTLGIV; SEQ ID NO: 539) of GenBank Accession NP_041326.1 (SEQ ID NO: 537), linked to HLA-A2.

Alternatively, HPV16E7 or a fragment thereof may be produced using standard biochemical techniques and modified in the context of HLA-A2 and used as immunogen.

In some embodiments, the immunogen may be a recombinant HPV16E7 peptide expressed in *E. coli* or in any other eukaryotic or mammalian cells such as Chinese hamster ovary (CHO) cells.

In certain embodiments, antigen-binding proteins that bind specifically a conformational epitope of an HLA-A2 presented HPV16E7 peptide may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of HLA-A2:HPV16E7 specific antigen-binding proteins, e.g., antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Non-limiting, exemplary in vitro assays for measuring binding activity are illustrated in Examples herein. In Example 4, the binding affinities and kinetic constants of human anti-HLA-A2:HPV16E7 specific antigen-binding proteins, e.g., antibodies were determined by surface plasmon resonance and the measurements were conducted on a Biacore 4000 or T200 instrument. Examples 6 and 7 describe the binding of the antibodies to cells overexpressing fragments of HPV16E7.

The antigen-binding proteins, e.g., antibodies, specific for HLA-A2:HPV16E7 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antigen-binding proteins may be used in diagnostic assays including imaging assays.

Antigen Binding Proteins

The present invention provides antigen-binding proteins that include antibodies, or antigen-binding fragments thereof, and CARs (e.g., nucleic acid molecules encoding a CAR of the invention) (described below). Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to a conformational epitope of an HLA-A2 presented HPV16E7 peptide. An antigen-binding protein, such as an antibody fragment, may include a Fab fragment, a F(ab')$_2$ fragment, a Fv fragment, a dAb fragment, a fragment containing a CDR, or an isolated CDR. Antigen binding proteins, such as antigen-binding fragments of an antibody, may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments of an antibody, include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antigen-binding protein (e.g., antibody), will typically comprise at least one variable domain. The variable domain may be of any size or amino acid composition and will generally comprise at least one CDR, which is adjacent to or in frame with one or more framework sequences. In antigen-binding proteins having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody, may contain a monomeric $V_H$ or $V_L$ domain.

In certain embodiments, an antigen-binding fragment of an antibody, may contain at least one variable domain covalently linked to at least one constant domain. Non-limiting, exemplary configurations of variable and constant domains that may be found within an antigen-binding fragment of an antigen-binding protein of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; $V_H$-$C_L$; $V_L$-$C_H1$; (ix) $V_L$-$C_H2$; (X) $V_L$-$C_H3$; (xi) $V_L$-$C_H1$-$C_H2$; (XII) $V_L$-$C_H1$-$C_H2$-$C_H3$; $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody, of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding proteins, e.g., antigen-binding fragments of an antibody, may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Antigen-Binding Proteins

Methods for generating antigen-binding proteins, such as human antibodies, in transgenic mice are known in the art. Any such known methods can be used in the context of the present invention to make human antibodies that specifically bind to a conformational epitope of an HLA-A2 presented human papillomavirus (HPV) 16 E7 peptide (HPV16E7 peptide).

Using VELOCIMMUNE® technology (see, for example, U.S. Pat. No. 6,596,541, Regeneron Pharmaceuticals, VELOCIMMUNE®) or any other known method for generating antigen-binding proteins, e.g., monoclonal antibodies, high affinity antigen-binding proteins, e.g., chimeric antibodies, to conformational epitope of an HLA-A2 presented HPV16E7 peptide, are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antigen-binding protein, e.g., antibody, comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antigen-binding proteins, e.g., antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antigen-binding protein may be produced in a cell, such as a CHO cell. Alternatively, DNA encoding the antigen-specific antigen-binding proteins, e.g., chimeric antibodies, or the variable domains of the light and heavy chains may be isolated directly from antigen-specific lymphocytes.

Initially, high affinity antigen-binding proteins, e.g., chimeric antibodies, are isolated having a human variable region and a mouse constant region. As in the experimental section below, the antigen-binding proteins are characterized and selected for desirable characteristics, including affinity, selectivity, epitope, etc. The mouse constant regions are replaced with a desired human constant region to generate the antigen-binding proteins, e.g., fully human antibodies, of the invention, for example wild-type or modified IgG1 or IgG4. While the constant region selected may vary according to specific use, high affinity antigen-binding and target specificity characteristics reside in the variable region.

Bioequivalents

The anti-HLA-A2:HPV16E7 antigen-binding proteins of the present invention encompass proteins having amino acid sequences that vary from those of the described antigen-binding proteins, e.g., antibodies, but that retain the ability to bind a conformational epitope of an HLA-A2 presented HPV16E7 peptide. Such variant antigen-binding proteins comprise one or more additions, deletions, or substitutions of amino acids when compared to parent sequence, but exhibit biological activity that is essentially equivalent to that of the described antigen-binding proteins. Likewise, the antigen-binding protein-encoding DNA sequences of the present invention encompass sequences that comprise one or more additions, deletions, or substitutions of nucleotides when compared to the disclosed sequence, but that encode an antigen-binding protein that is essentially bioequivalent to an antigen-binding protein of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antigen-binding proteins or antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins (or antibodies) are bioequivalent if there are no clinically meaningful differences in their safety, purity, or potency.

In one embodiment, two antigen-binding proteins (or antibodies) are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins (or antibodies) are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antigen-binding protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antigen-binding protein (or its target) is measured as a function of time; and (d) in a well-controlled clinical trial that establishes safety, efficacy, or bioavailability or bioequivalence of an antigen-binding protein.

Bioequivalent variants of the antigen-binding proteins (or antibodies) of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include antigen-binding protein variants comprising amino acid changes, which modify the glycosylation characteristics of the antigen-binding proteins, e.g., mutations that eliminate or remove glycosylation.

Anti-HLA-A2:HPV16E7 Antigen Binding-Proteins Comprising Fc Variants

According to certain embodiments of the present invention, anti-HLA-A2:HPV16E7 antigen-binding proteins, e.g., antibodies, are provided comprising an Fc domain comprising one or more mutations which enhance or diminish antigen-binding protein binding to the FcRn receptor, e.g., at acidic pH as compared to neutral pH. For example, the present invention includes anti-HLA-A2:HPV16E7 antigen-binding proteins comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antigen-binding protein when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-HLA-A2:HPV16E7 antigen-binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present invention includes anti-HLA-A2:HPV16E7 antigen-binding proteins comprising an Fc domain comprising a S108P mutation in the hinge region of IgG4 to promote dimer stabilization. All possible combinations of the foregoing Fc domain mutations, and other mutations within the antigen-binding protein variable domains disclosed herein, are contemplated within the scope of the present invention.

The present invention also includes anti-HLA-A2:HPV16E7 antigen-binding proteins comprising a chimeric heavy chain constant ($C_H$) region, wherein the chimeric $C_H$ region comprises segments derived from the $C_H$ regions of more than one immunoglobulin isotype. For example, the antigen-binding proteins of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antigen-binding proteins of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antigen-binding protein comprising a chimeric $C_H$ region as described herein may, in certain embodiments, exhibit modified Fc effector functions without adversely affecting the therapeutic or pharmacokinetic properties of the antigen-binding protein. (See, e.g., U.S. Patent Publication No. 20140243504, the disclosure of which is hereby incorporated by reference in its entirety).

Biological Characteristics of the Antigen-Binding Proteins

In general, the antigen-binding proteins of the present invention function by binding to a conformational epitope of an HLA-A2 presented human papillomavirus (HPV) 16 E7 peptide (HPV16E7) peptide.

The present invention includes anti-HLA-A2:HPV16E7 antigen-binding proteins that bind HPV16E7 peptide in the context of HLA-A2 with high specificity. The anti-HLA-A2:HPV16E7 antigen-binding proteins do not bind to the HPV16E7 peptide in the absence of HLA-A2. Further, the anti-HLA-A2:HPV16E7 antigen-binding proteins do not bind to an off-target peptide in the context of HLA-A2.

The present invention includes anti-HLA-A2:HPV16E7 antigen-binding proteins that bind monomeric HLA-A2:HPV16E7 11-19 peptide with high affinity. For example, the present invention includes antigen-binding proteins that bind monomeric HLA-A2:HPV16E7 11-19 peptide (e.g., at 25° C. or at 37° C.) with a $K_D$ of less than about 20 nM as measured by surface plasmon resonance, e.g., using the assay format as defined in Example 4 herein. In certain embodiments, the antigen-binding proteins bind monomeric HLA-A2:HPV16E7 11-19 peptide with a $K_D$ of less than about 15 nM, less than about 12 nM, less than about 10 nM, less than about 5 nM, less than about 2 nM, less than about 1 nM, less than about 0.5 nM less than about 0.1 nM, less than about 0.05 nM or less than about 0.04 nM, as measured by surface plasmon resonance, e.g., using the assay format as defined in Example 4 herein, or a substantially similar assay.

The present invention includes antigen-binding proteins that bind monomeric HLA-A2:HPV16E7 82-90 peptide (e.g., at 25° C. or at 37° C.) with a $K_D$ of less than about 25 nM as measured by surface plasmon resonance, e.g., using the assay format as defined in Example 4 herein, or a substantially similar assay. In certain embodiments, the antigen-binding proteins bind monomeric HLA-A2:HPV16E7 82-90 peptide with a $K_D$ of less than about 20 nM, less than about 15 nM, less than about 12 nM, less than about 10 nM, less than about 5 nM, less than about 2 nM, less than about 1 nM, less than about 0.5 nM less than about 0.1 nM, less than about 0.05 nM or less than about 0.04 nM, as measured by surface plasmon resonance, e.g., using the assay format as defined in Example 4 herein, or a substantially similar assay.

The present invention also includes antigen-binding proteins that bind to a cell expressing an HLA-A2:HPV16E7 11-19 peptide with an $EC_{50}$ less than about 6 nM and do not bind to cells expressing predicted off-target peptides as determined by luminescence assay, as defined in Example 6 herein, or a substantially similar assay. In certain embodiments, the antigen-binding proteins bind to a cell expressing an HLA-A2:HPV16E7 11-19 peptide with an $EC_{50}$ less than about less than about 6 nM, less than about 5 nM, less than about 2 nM, less than about 1 nM, or less than about 0.5 nM, and do not bind to cells expressing predicted off-target peptides as determined by luminescence assay, as defined in Example 6 herein, or a substantially similar assay. e.g., using the assay format in Example 6 herein, or a substantially similar assay.

The present invention also includes antigen-binding proteins that bind to a cell expressing an HLA-A2:HPV16E7 82-90 peptide with an $EC_{50}$ less than about 1 nM and do not bind to cells expressing predicted off-target peptides as determined by luminescence assay, as defined in Example 6 herein, or a substantially similar assay. In certain embodiments, the antigen-binding proteins bind to a cell expressing an HLA-A2:HPV16E7 82-90 peptide with an $EC_{50}$ less than about less than about 1 nM, less than about 0.5 nM, less than about 0.2 nM, or less than about 0.01 nM and do not bind to cells expressing predicted off-target peptides as determined by luminescence assay, as defined in Example 6 herein, or a substantially similar assay. e.g., using the assay format in Example 6 herein, or a substantially similar assay.

The present invention also includes antigen-binding proteins that bind to a cell expressing an HLA-A2:HPV16E7 11-19 peptide with an $EC_{50}$ less than about 30 nM as measured by a flow cytometry assay as defined in Example 7 herein, or a substantially similar assay. In certain embodiments, the antigen-binding proteins bind to a cell expressing an HLA-A2:HPV16E7 11-19 peptide with an $EC_{50}$ less than about 25 nM, less than about 20 nM, less than about 15 nM, less than about 10 nM, less than about 5 nM, less than about 2 nM, less than about 1 nM, or less than about 0.5 nM, as measured by a flow cytometry assay, e.g., using the assay format in Example 7 herein, or a substantially similar assay.

The present invention also includes antigen-binding proteins that bind to a cell expressing an HLA-A2:HPV16E7 82-90 peptide with an $EC_{50}$ less than about 75 nM as measured by a flow cytometry assay as defined in Example 7 herein, or a substantially similar assay. In certain embodiments, the antigen-binding proteins bind to a cell expressing an HLA-A2:HPV16E7 82-90 peptide with an $EC_{50}$ less than about 75 nM, less than about 70 nM, less than about 65 nM, less than about 60 nM, less than about 55 nM, less than about 50 nM, less than about 45 nM, less than about 40 nM, less than about 35 nM, less than about 30 nM, less than about 25 nM, less than about 20 nM, less than about 15 nM, less than about 10 nM, less than about 5 nM, less than about 2 nM, less than about 1 nM, or less than about 0.5 nM, as measured by a flow cytometry assay, e.g., using the assay format in Example 7 herein, or a substantially similar assay.

In certain embodiments, the antigen-binding proteins of the present invention are useful in inhibiting the growth of a tumor or delaying the progression of cancer when administered prophylactically to a subject in need thereof and may increase survival of the subject. For example, the administration of an antigen-binding protein of the present invention may lead to shrinking of a primary tumor and may prevent metastasis or development of secondary tumors. In certain embodiments, the antigen-binding proteins of the present invention are useful in inhibiting the growth of a tumor when administered therapeutically to a subject in need thereof and may increase survival of the subject. For example, the administration of a therapeutically effective amount of an antigen-binding protein of the invention to a subject may lead to shrinking and disappearance of an established tumor in the subject.

In one embodiment, the invention provides an isolated recombinant antigen-binding protein thereof that binds to a conformational epitope of an HLA-A2 presented HPV16E7 peptide, wherein the antigen-binding protein exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 218, 234, 250, 266, 282, 298, 314, 330, 346, 362, 378, 394, 410, 426, 442, 458, 474, 490, 506, and 522, or a substantially similar sequence thereof having at least 90%, at least 95%, at least 96%, at least 97%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 226, 242, 258, 274, 290, 306, 322, 338, 354, 370, 386, 402, 418, 434, 450, 466, 482, 498, 514, and 530, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528, or a substantially similar sequence thereof having at least 90%, at least 95%, at least 96%, at least 97%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536, or a substantially similar sequence thereof having at least 90%, at least 95%, at least 96%, at least 97%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524, or a substantially similar sequence thereof having at least 90%, at least 95%, at least 96%, at least 97%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 228, 244, 260, 276, 292, 308, 324, 340, 356, 372, 388, 404, 420, 436, 452, 468, 484, 500, 516, and 532, or a substantially similar sequence thereof having at least 90%, at least 95%, at least 96%, at least 97%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534, or a substantially similar sequence thereof having at least 90%, at least 95%, at least 96%, at least 97%, at least 98% or at least 99% sequence identity; (v) binds monomeric HLA-A2:HPV16E7 11-19 peptide with a binding dissociation equilibrium constant (KD) of less than about 20 nM as measured in a surface plasmon resonance assay at 25° C.; (vi) binds monomeric HLA-A2:HPV16E7 82-90 peptide with a binding dissociation equilibrium constant (KD) of less than about 25 nM as measured in a surface plasmon resonance assay at 25° C.; (vii) binds to HLA-A2:HPV16E7 11-19 peptide expressing cells with an EC50 less than about 6 nM and do not bind to cells expressing predicted off-target peptides as determined by luminescence assay; (viii) binds to HLA-A2:HPV16E7 82-90 peptide expressing cells with an EC50 less than about 1 nM and do not substantially bind to cells expressing predicted off-target peptides as determined by luminescence assay; (ix) binds to HLA-A2:HPV16E7 11-19 peptide expressing cells with an EC50 less than about 30 nM as determined by flow cytometry assay; (x) binds to HLA-A2:HPV16E7 82-90 peptide expressing cells with an EC50 less than about 75 nM as determined by flow cytometry assay; (xi) does not bind to a HLA-A2-displayed off-target peptide wherein the peptide differs by 1, 2, 3, 4, 5 or more amino acids from SEQ ID NO: 538; and (xii) does not bind to a HLA-A2-displayed off-target peptide wherein the peptide differs by 1, 2, 3, 4, 5 or more amino acids from SEQ ID NO: 539.

The antigen-binding proteins of the present invention may possess one or more of the aforementioned biological characteristics, or any combinations thereof. Other biological characteristics of the antigen-binding proteins of the present invention will be evident to a person of ordinary skill in the art from a review of the present disclosure including the working Examples herein.

Epitope Mapping and Related Technologies

The present invention includes anti-HLA-A2:HPV16E7 antigen-binding proteins which interact with one or more amino acids found within one or more domains of the HLA-A2 displayed HPV16E7 peptide. The epitope may consist of a plurality of non-contiguous amino acids (or amino acid sequences) located within either or both of the aforementioned domains of the HPV16E7 molecule (e.g. a conformational epitope).

Various techniques known to persons of ordinary skill in the art can be used to determine whether an antigen-binding protein "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein interacts is hydrogen/deuterium exchange detected by mass spectrometry. In general terms, the hydrogen/deuterium exchange method involves deuterium-labeling the protein of interest, followed by binding the antigen-binding protein to the deuterium-labeled protein. Next, the protein/antigen-binding protein complex is transferred to water and exchangeable protons within amino acids that are protected by the antigen-binding protein complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein, the target protein is subjected to protease cleavage and mass spectrometry analysis, thereby revealing the deuterium-labeled residues which correspond to the specific amino acids with which the antigen-binding protein interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antigen-binding proteins, e.g., antibodies (mAbs), directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antigen-binding proteins, such that characterization can be focused on genetically distinct antigen-binding proteins. When applied to hybridoma screening, MAP may facilitate identification of rare hybridoma clones that produce antigen-binding proteins having the desired characteristics. MAP may be used to sort the antigen-binding proteins of the invention into groups of antigen-binding proteins binding different epitopes.

The present invention includes anti-HLA-A2:HPV16E7 antigen-binding proteins that bind to the same epitope, or a portion of the epitope, as any of the specific exemplary antigen-binding proteins described herein in Table 1, or an antigen-binding protein having the CDR sequences of any of the exemplary antigen-binding proteins described in Table 1. Likewise, the present invention also includes anti-HLA-A2:HPV16E7 antigen-binding proteins that compete for binding to HLA-A2:HPV16E7 or a fragment thereof with any of the specific exemplary antigen-binding proteins described herein in Table 1, or an antigen-binding protein having the CDR sequences of any of the exemplary antigen-binding proteins described in Table 1.

One can easily determine whether an antigen-binding protein binds to the same epitope as, or competes for binding with, a reference anti-HLA-A2:HPV16E7 antigen-binding protein by using routine methods known in the art. For example, to determine if a test antigen-binding protein binds to the same epitope as a reference anti-HLA-A2:HPV16E7 antigen-binding protein of the invention, the reference antigen-binding protein is allowed to bind to a HLA-A2:HPV16E7 protein or peptide under saturating conditions. Next, the ability of a test antigen-binding protein to bind to the HLA-A2:HPV16E7 molecule is assessed. If the test antigen-binding protein is able to bind to HLA-A2:HPV16E7 following saturation binding with the reference anti-HLA-A2:HPV16E7 antigen-binding protein, it can be concluded that the test antigen-binding protein binds to a different epitope than the reference anti-HLA-A2:HPV16E7 antigen-binding protein. On the other hand, if the test antigen-binding protein is not able to bind to the HLA-A2:HPV16E7 protein following saturation binding with the reference anti-HLA-A2:HPV16E7 antigen-binding protein, then the test antigen-binding protein may bind to the same epitope as the epitope bound by the reference anti-HLA-A2:HPV16E7 antigen-binding protein of the invention.

To determine if an antigen-binding protein competes for binding with a reference anti-HLA-A2:HPV16E7 antigen-binding protein, the above-described binding methodology is performed in two orientations: In a first orientation, the reference antigen-binding protein is allowed to bind to a HLA-A2:HPV16E7 protein under saturating conditions followed by assessment of binding of the test antigen-binding protein to the HLA-A2:HPV16E7 molecule. In a second orientation, the test antigen-binding protein is allowed to bind to a HLA-A2:HPV16E7 molecule under saturating conditions followed by assessment of binding of the reference antigen-binding protein to the HLA-A2:HPV16E7 molecule. If, in both orientations, only the first (saturating) antigen-binding protein is capable of binding to the HLA-A2:HPV16E7 molecule, then it is concluded that the test antigen-binding protein and the reference antigen-binding protein compete for binding to HLA-A2:HPV16E7. As will be appreciated by a person of ordinary skill in the art, an antigen-binding protein that competes for binding with a reference antigen-binding protein may not necessarily bind to the identical epitope as the reference antigen-binding protein, but may sterically block binding of the reference antigen-binding protein by binding an overlapping or adjacent epitope.

Two antigen-binding proteins bind to the same or overlapping epitope if each competitively inhibits (blocks) binding of the other to the antigen. That is, a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990 50:1495-1502). Alternatively, two antigen-binding proteins have the same epitope if essentially all amino acid mutations in the antigen that reduce or eliminate binding of one antigen-binding protein reduce or eliminate binding of the other. Two antigen-binding proteins have overlapping epitopes if some amino acid mutations that reduce or eliminate binding of one antigen-binding protein reduce or eliminate binding of the other.

Additional routine experimentation (e.g., peptide mutation and binding analyses) can then be carried out to confirm whether the observed lack of binding of the test antigen-binding protein is in fact due to binding to the same epitope as the reference antigen-binding protein or if steric blocking (or another phenomenon) is responsible for the lack of observed binding. Experiments of this sort can be performed using ELISA, RIA, surface plasmon resonance, flow cytometry or any other quantitative or qualitative antigen-binding protein-binding assay available in the art.

Immunoconjugates

The invention encompasses anti-HLA-A2:HPV16E7 antigen-binding proteins conjugated to a therapeutic moiety ("immunoconjugate"), such as a cytotoxin or a chemotherapeutic agent to treat cancer. As used herein, the term "immunoconjugate" refers to an antigen-binding protein which is chemically or biologically linked to a cytotoxin, a radioactive agent, a cytokine, an interferon, a target or reporter moiety, such as a detectable moiety, an enzyme, a toxin, a peptide or protein or a therapeutic agent. The antigen-binding protein may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antigen-binding protein-drug conjugates and antigen-binding protein-toxin fusion proteins. In one embodiment, the agent may be a second different antibody to HPV16E7 or HLA-A2:HPV16E7. In certain embodiments, the antigen-binding protein may be conjugated to an agent specific for a tumor cell or a virally infected cell, i.e., an HPV infected cell. The type of therapeutic moiety that may be conjugated to the anti-HLA-A2:HPV16E7 antigen-binding protein and will take into account the condition to be treated and the desired therapeutic effect to be achieved. Examples of suitable agents for forming immunoconjugates are known in the art; see for example, PCT Publication No. WO 05/103081.

Chimeric Antigen Receptors (CAR)

Chimeric antigen receptors (CARs) redirect T cell specificity toward antibody-recognized antigens expressed on the surface of cancer cells, while T cell receptors (TCRs) extend the range of targets to include intracellular tumor antigens. CAR redirected T cells specific for the B cell differentiation antigen CD19 have shown dramatic efficacy in the treatment of B cell malignancies, while TCR-redirected T cells have shown benefits in patients suffering from solid cancer. Stauss et al. describe strategies to modify therapeutic CARs and TCRs, for use in the treatment of cancer, for example, to enhance the antigen-specific effector function and limit toxicity of engineered T cells (*Current Opinion in Pharmacology* 2015, 24:113-118).

One aspect of the invention includes a chimeric antigen receptor (CAR) which is specific for an HPV16E7 peptide displayed on the surface of tumor cells by HLA-A2, such as a peptide comprising amino acid residues 11-19 or 82-90 of HPV16E7. In one embodiment of the present invention, a CAR as described herein comprises an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, CD28, CD137, CD134 or CD278. In one embodiment, the CAR includes a hinge or spacer region between the extracellular binding domain and the transmembrane domain, such as a CD8alpha hinge. In another embodiment of the present invention, a CAR as described herein comprises an extracellular target-specific binding domain, and a T cell receptor constant domain ("T-body construct").

It is to be understood that, for use in any of the CARs described herein, the extracellular target-specific binding domain may comprise a Fab, a Fab', a (Fab')2, an Fv, or a single chain Fv (scFv) of an antigen-binding protein of the invention.

As used herein, the binding domain or the extracellular domain of the CAR, provides the CAR with the ability to bind to the target antigen of interest. A binding domain can be any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable regions, or the light and heavy chain variable regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE analysis), and are described herein. The target may be any antigen of clinical interest against which it would be desirable to trigger an effector immune response that results in tumor killing. In one embodiment, the target antigen of the binding domain of the chimeric antigen receptor is a conformational epitope of an HLA-A2 presented HPV16E7 peptide on the surface of tumor cells, such as a peptide comprising amino acid residues 11-19 or 82-90 of HPV16E7.

Illustrative binding domains include antigen-binding proteins, such as antigen-binding fragments of an antibody, such as scFv, scTCR, extracellular domains of receptors, ligands for cell surface molecules/receptors, or receptor binding domains thereof, and tumor binding proteins. In certain embodiments, the antigen-binding domains included in a CAR of the invention can be a variable region (Fv), a CDR, a Fab, an scFv, a VH, a VL, a domain antibody variant (dAb), a camelid antibody (VHH), a fibronectin 3 domain variant, an ankyrin repeat variant and other antigen-specific binding domain derived from other protein scaffolds.

In one embodiment, the binding domain of the CAR is an anti-HLA-A2:HPV16E7 single chain antibody (scFv), and may be a murine, human or humanized scFv. Single chain antibodies may be cloned form the V region genes of a hybridoma specific for a desired target. A technique which can be used for cloning the variable region heavy chain (VH) and variable region light chain (VL) has been described, for example, in Orlandi et al., *PNAS,* 1989; 86: 3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs of the present invention may comprise a linker between the various domains, added for appropriate spacing and conformation of the molecule. For example, in one embodiment, there may be a linker between the binding domain VH or VL which may be between 1-10 amino acids long. In other embodiments, the linker between any of the domains of the chimeric antigen receptor may be between 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long. Ranges including the numbers described herein are also included herein, e.g., a linker 10-30 amino acids long.

In certain embodiments, linkers suitable for use in the CAR described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR can include linkers that are all or partially flexible, such that the linker can include a flexible linker as well as one or more portions that confer less flexible structure to provide for a desired CAR structure.

The binding domain of the CAR may be followed by a "spacer," or, "hinge," which refers to the region that moves the antigen-binding domain away from the effector cell surface to enable proper cell/cell contact, antigen-binding and activation (Patel et al., *Gene Therapy,* 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered. In one embodiment, the hinge region comprises a CD8alpha hinge.

The "transmembrane," region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain," refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen-binding to the extracellular CAR domain. The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Primary cytoplasmic signaling sequences regulate primary activation of the T cell receptor complex either an inhibitory way, or in an inhibitory way. Primary cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular used in the invention include those derived from TCRzeta, FcRgamma, FcRbeta, CD3gamma, CD3delta, CD3epsilon, CD5, CD22, CD79a, CD79b and CD66d. In certain particular embodiments, the intracellular signaling domain of the anti-HLA-A2: HPV16E7 CARs described herein are derived from CD3zeta or FcRgamma.

As used herein, the term, "co-stimulatory signaling domain," or "co-stimulatory domain", refers to the portion of the CAR comprising the intracellular domain of a co-stimulatory molecule. Co-stimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta and 4-1BB, other costimulatory domains are contemplated for use with the CARs described herein. The inclusion of one or more co-stimulatory signaling domains may enhance the efficacy and expansion of T cells expressing CAR receptors. The intracellular signaling and co-stimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant co-stimulatory signal. Other CARs containing a binding domain, a hinge, a transmembrane and the signaling domain derived from CD3zeta or FcRgamma together with one or more co-stimulatory signaling domains (e.g., intracellular co-stimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., *Molecular Therapy*, 2009; 17: 1453-1464; Zhong et al., *Molecular Therapy*, 2010; 18: 413-420; Carpenito et al., *PNAS*, 2009; 106:3360-3365).

In one embodiment, the HLA-A2:HPV16E7 CARs of the invention comprise (a) an anti-HLA-A2:HPV16E7 scFv as a binding domain (e.g., an scFv having binding regions (e.g., CDRs or variable domains) from any one or more of the HLA-A2:HPV16E7 antibodies described in Table 1) (b) a hinge region derived from human CD8alpha, (c) a human CD8alpha transmembrane domain, and (d) a human T cell receptor CD3 zeta chain (CD3) intracellular signaling domain, and optionally one or more co-stimulatory signaling domains derived from CD28, CD137, CD134, and CD278. In one embodiment, the different protein domains are arranged from amino to carboxyl terminus in the following order: binding domain, hinge region and transmembrane domain. The intracellular signaling domain and optional co-stimulatory signaling domains are linked to the transmembrane carboxy terminus in any order in tandem to form a single chain chimeric polypeptide. In one embodiment, a nucleic acid construct encoding an HLA-A2:HPV16E7 CAR is a chimeric nucleic acid molecule comprising a nucleic acid molecule comprising different coding sequences, for example, (5' to 3') the coding sequences of a human anti-HLA-A2:HPV16E7 scFv, a human CD8alpha-hinge, a human CD8alpha transmembrane domain and a CD3zeta intracellular signaling domain. In another embodiment, a nucleic acid construct encoding an HLA-A2: HPV16E7 CAR is a chimeric nucleic acid molecule comprising a nucleic acid molecule comprising different coding sequences, for example, (5' to 3') the coding sequences of a human anti-HLA-A2:HPV16E7 scFv, a human CD8alpha-hinge, a human CD8alpha transmembrane domain, a CD137 co-stimulatory domain, and a CD3zeta co-stimulatory domain. In certain embodiments, a nucleic acid construct encoding an HLA-A2:HPV16E7 CAR is a chimeric nucleic acid molecule comprising a nucleic acid molecule comprising different coding sequences, for example, (5' to 3') the coding sequences of a human anti-HLA-A2:HPV16E7 scFv, a human CD8alpha-hinge, a human CD8alpha transmembrane domain, a CD137 co-stimulatory domain, and a CD3zeta co-stimulatory domain, wherein the anti-HLA-A2: HPV16E7 scFv comprises a $V_H$ selected from the group consisting of SEQ ID Nos: 2, 34, 82, 194, 282, and 506, and a $V_L$ selected from the group consisting of SEQ ID Nos: 10, 42, 90, 202, 290 and 514. In some embodiments, the present invention includes a nucleic acid molecule that encodes for a HLA-A2:HPV16E7 CAR selected from the group consisting of SEQ ID Nos: 540, 541, 542, 543, 544 and 545.

In certain embodiments, the polynucleotide encoding the CAR described herein is inserted into a vector. The term "vector" as used herein refers to a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha. promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine, c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR of the present invention are provided in a viral vectors. A viral vector can be those derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for a the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immunodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.*, 1998; 72: 8463-8471 and Zufferey et al., *J. Virol.* 1998; 72:9873-9880).

Retroviral vectors (i.e., both lentiviral and non-lentiviral) for use in the present invention can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a HLA-A2:HPV16E7 CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

The CARs of the present invention are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or a may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding an anti-HLA-A2:HPV16E7 CAR carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the CAR of the present invention is introduced and expressed in immune effector cells so as to redirect their specificity to a target antigen of interest, e.g., a conformational epitope of an HLA-A2 displayed HPV16E7 peptide, e.g., amino acid residues 11-19 or 82-90.

The present invention provides methods for making the immune effector cells which express the CAR as described herein. In one embodiment, the method comprises transfecting or transducing immune effector cells isolated from a subject, such as a subject having an HPV16E7-associate disease or disorder, such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. Such recombinant T cells are referred to herein as "T-bodies."

In one embodiment of the present invention, a T-body includes a CAR of the invention comprising an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, CD28, CD137, CD134 or CD278. In another embodiment of the present invention, a T-body includes a CAR of the invention comprising an extracellular target-specific binding domain, a transmembrane domain, a hinge or spacer region between the extracellular binding domain and the transmembrane domain, an intracellular signaling domain (such as a signaling domain derived from CD3zeta or FcRgamma), and/or one or more co-stimulatory signaling domains derived from a co-stimulatory molecule. In yet another embodiment of the present invention, a T-body includes a T-body construct CAR comprising an extracellular target-specific binding domain, and a T cell receptor constant domain. The extracellular target-specific binding domain suitable for use in a T-body comprising any of the CARs described herein may comprise a Fab, a Fab', a (Fab')2, an Fv, or a single chain Fv (scFv) of an antigen-binding protein of the invention.

T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium and may lack magnesium or may lack many if not all divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMC may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+ T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+ T helper cells can be sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000, US 2016/0175358. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

The invention provides a population of modified immune effector cells for the treatment of an HPV-associated disease or disorder, e.g., cancer, the modified immune effector cells comprising an HLA-A2:HPV16E7 CAR as disclosed herein.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations of the present invention may be administered either alone, or as a pharmaceutical composition in combination with diluents and/or with other components such as IL-2 or other cytokines or cell populations. Briefly, pharmaceutical compositions of the present invention may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

The anti-tumor immune response induced in a subject by administering CAR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

Thus, the present invention provides for methods of treating an individual diagnosed with or suspected of having, or at risk of developing, an HPV-associated disease or disorder, e.g., HPV16E7-positive cancer, comprising administering the individual a therapeutically effective amount of the CAR-expressing immune effector cells as described herein.

In one embodiment, the invention provides a method of treating a subject diagnosed with an HPV16E7-positive cancer comprising removing immune effector cells from a subject diagnosed with an HPV16E7-positive cancer, genetically modifying said immune effector cells with a vector comprising a nucleic acid encoding a chimeric antigen receptor of the instant invention, thereby producing a population of modified immune effector cells, and administering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a CAR of the invention in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the invention and returning the transduced cells into the subject.

Therapeutic Administration and Formulations

The invention provides therapeutic compositions comprising the anti-HLA-A2:HPV16E7 antigen-binding proteins, e.g., antibodies, or antigen-biding fragments thereof, or CARs, of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of the antigen-binding protein, e.g., antibody, or antigen-biding fragments thereof, may vary depending upon the age and the size of a subject to be administered, target disease, conditions, route of administration, and the like. When an antigen-binding protein of the present invention is used for treating a disease or disorder in an adult patient, or for preventing such a disease, it is advantageous to administer the antigen-binding protein, e.g., antibody, or antigen-biding fragments thereof, of the present invention normally at a single dose of about 0.1 to about 60 mg/kg body weight, more preferably about 5 to about 60, about 20 to about 50, about 10 to about 50, about 1 to about 10, or about 0.8 to about 11 mg/kg body weight. Depending on the severity of the condition, the frequency and the duration of the treatment can be adjusted. In certain embodiments, the antigen-binding protein, e.g., antibody, or antigen-biding fragments thereof, of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antigen-binding protein, e.g., antibody, or antigen-biding fragments thereof, in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing mutant viruses, receptor mediated endocytosis (see, e.g., Wu et al. (1987) *J. Biol. Chem.* 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) *Science* 249: 1527-1533).

The use of nanoparticles to deliver the antigen-binding proteins, e.g., antibody, or antigen-biding fragments thereof, of the present invention is also contemplated herein. Antigen binding protein-conjugated nanoparticles may be used both for therapeutic and diagnostic applications. Antigen binding protein-conjugated nanoparticles and methods of preparation and use are described in detail by Arruebo, M., et al. 2009 ("Antibody-conjugated nanoparticles for biomedical applications" in *J. Nanomat*. Volume 2009, Article ID 439389, 24 pages, doi: 10.1155/2009/439389), incorporated herein by reference. Nanoparticles may be developed and conjugated to antigen-binding proteins contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™ OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antigen-binding protein contained is generally about 5 to about 500 mg per dosage form in a unit dose; especially in the form of injection, it is preferred that the antigen-binding protein is contained in about 5 to about 100 mg and in about 10 to about 250 mg for the other dosage forms.

Therapeutic Uses of the Antigen-Binding Proteins

The antibodies of the invention are useful, inter alia, for the treatment, prevention and/or amelioration of any disease or disorder associated with or mediated by HPV16. For example, the present invention provides methods for treating a HPV-associated disease or disorder, such as an HPV-associated cancer (e.g., a HPV16E7-positive cancer) (tumor growth inhibition) and/or HPV infections by administering an anti-HLA-A2:HPV16E7 antigen-binding protein (or pharmaceutical composition comprising an anti-HLA-A2:HPV16E7 antigen-binding protein) as described herein to a patient in need of such treatment, and anti-HLA-A2:HPV16E7 antigen-binding proteins (or pharmaceutical composition comprising an anti-HLA-A2:HPV16E7 antigen-binding protein) for use in the treatment of a HPV-associated cancer (tumor growth inhibition) and/or HPV infections. The antigen-binding proteins of the present invention are useful for the treatment, prevention, and/or amelioration of disease or disorder or condition such as an HPV-associated cancer or a HPV infection and/or for ameliorating at least one symptom associated with such disease, disorder or condition. In the context of the methods of treatment described herein, the anti-HLA-A2:HPV16E7 antigen-binding protein may be administered as a monotherapy (i.e., as the only therapeutic agent) or in combination with one or more additional therapeutic agents (examples of which are described elsewhere herein).

In some embodiments of the invention, the antibodies described herein are useful for treating subjects suffering from primary or recurrent cancer, including, but not limited to, HPV-associated cancer, e.g., squamous cell carcinomas, such as squamous cell carcinoma of head and neck, cervical cancer, anogenital cancer, oropharyngeal cancer.

The antigen-binding proteins may be used to treat early stage or late-stage symptoms of the HPV-associated cancer. In one embodiment, an antibody or fragment thereof of the invention may be used to treat advanced or metastatic cancer. The antigen-binding proteins are useful in reducing or inhibiting or shrinking tumor growth. In certain embodiments, treatment with an antigen-binding protein of the invention leads to more than 40% regression, more than 50% regression, more than 60% regression, more than 70% regression, more than 80% regression or more than 90% regression of a tumor in a subject. In certain embodiments, the antigen-binding proteins may be used to prevent relapse of a tumor. In certain embodiments, the antigen-binding proteins are useful in extending progression-free survival or overall survival in a subject with HPV-associated cancer. In some embodiments, the antibodies are useful in reducing toxicity due to chemotherapy or radiotherapy while maintaining long-term survival in a patient suffering from HPV-associated cancer.

In certain embodiments, the antigen-binding proteins of the invention are useful to treat subjects suffering from a chronic HPV infection. In some embodiments, the antigen-binding proteins of the invention are useful in decreasing viral titers in the host.

One or more antibodies of the present invention may be administered to relieve or prevent or decrease the severity of one or more of the symptoms or conditions of the disease or disorder.

It is also contemplated herein to use one or more antibodies of the present invention prophylactically to patients at risk for developing a disease or disorder such as HPV-associated disease or disorder, such as an HPV-associated cancer, and HPV infection.

In a further embodiment of the invention, the present antibodies are used for the preparation of a pharmaceutical composition for treating patients suffering from HPV-associated disease or disorder, such as an HPV-associated cancer, or HPV infection. In another embodiment of the invention, the present antibodies are used as adjunct therapy with any other agent or any other therapy known to those skilled in the art useful for treating HPV-associated cancer or HPV infection.

Combination Therapies and Formulations

Combination therapies may include an anti-HLA-A2:HPV16E7 antigen-binding protein of the invention, such as a CAR of the invention (e.g., an immune effector cell comprising a CAR of the invention) or a pharmaceutical composition of the invention, and any additional therapeutic agent that may be advantageously combined with an antigen-binding protein of the invention. The antigen-binding proteins of the present invention may be combined synergistically with one or more anti-cancer drugs or therapy used to treat or inhibit an HPV16E7-associated disease or disorder, such as HPV-positive cancer, e.g., squamous cell carcinoma, cervical cancer, anogenital cancer, head and neck cancer, or oropharyngeal cancer.

It is contemplated herein to use the anti-HLA-A2:HPV16E7 antigen-binding proteins of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antigen-binding proteins of the present invention may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, surgery, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as antioxidants or any other therapy care to treat cancer. In certain embodiments, the anti-HLA-A2:HPV16E7 antigen-binding protein of the present invention may be used in combination with an HPV vaccine. Exemplary HPV vaccines include Gardasil, Gardasil 9, and Cervarix, Lm-LLo-E7 (ADXS11-001; ADXS-HPV; Advaxis, Inc.); GLBL101c (GENOLAC BL Corp); TA-HPV (European Organization for Research and Treatment of Cancer (EORTC)); TG4001 (Transgene/Roche); MVA E2 (Instituto Mexicano del Seguro Social); HPV16-SLP (ISA Pharmaceuticals); GL-0810 (Gliknik Inc.); Pepcan+Candin (University of Arkansas); GTL001 (ProCervix; Genticel); TA-CIN (Xenova Research Limited); TA-CIN+TA-HPV (Celtic Pharma); pNGVL4a-sig/E7(detox)/HSP70+TA-HPV (Sidney Kimmel Comprehensive Cancer Center); pNGVL4a-CRT/E7(detox) (Sidney Kimmel Comprehensive Cancer Center); GX-188E (Genexine, Inc); VGX-3100 (Inovio Pharmaceuticals); Dendritic Cells pulsed with HPV-16 and HPV-18 E7 and keyhole limpet hemocyanin (National Institutes of Health); DC pulsed with HPV+ tumor lysate (Department of Biotechnology (DBT, Govt. of India)); PDS0101 (PDS Biotechnology Corp); ProCervix (Genticel); GX-188E (Genexine, Inc); pNGVL4a-CRT/E7(detox) (Sidney Kimmel Comprehensive Cancer Center); pNGVL4a-sig/E7(detox)/HSP70+TA-HPV (Sidney Kimmel Comprehensive Cancer Center); TVGV-1+GPI-0100 (THEVAX Genetics Vaccine Co.); Pepcan+Candin (University of Arkansas); ISA101 (SLP-HPV-01; HPV16-SLP; ISA Pharmaceuticals); ADXS11-001 (Lm-LLo-E7; Advaxis, Inc.); ISA101 (SLP-HPV-01; HPV16-SLP; ISA Pharmaceuticals); DPX-E7 (Dana-Farber Cancer Institute); ADXS11-001 (Lm-LLo-E7; Advaxis, Inc.); INO-3112 (VGX-3100+INO-9012; Inovio Pharmaceuticals);

ADXS11-001 (Lm-LLo-E7; Advaxis, Inc.); INO-3112 (VGX-3100+INO-9012; Inovio Pharmaceuticals); ISA101 (SLP-HPV-01; HPV16-SLP; ISA Pharmaceuticals); and TA-CIN+GPI-0100 (Sidney Kimmel Comprehensive Cancer Center). In certain embodiments, the anti-HLA-A2:HPV16E7 antigen-binding protein of the present invention may be used in combination with cancer vaccines including dendritic cell vaccines, oncolytic viruses, tumor cell vaccines, etc. to augment the anti-tumor response. Examples of cancer vaccines that can be used in combination with anti-HLA-A2:HPV16E7 antigen-binding proteins of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+cancers).

In certain embodiments, the anti-HLA-A2:HPV16E7 antigen-binding proteins of the invention may be administered in combination with radiation therapy in methods to generate long-term durable anti-tumor responses and/or enhance survival of patients with cancer. In some embodiments, the anti-HLA-A2:HPV16E7 antigen-binding proteins of the invention may be administered prior to, concomitantly or after administering radiation therapy to a cancer patient. For example, radiation therapy may be administered in one or more doses to tumor lesions followed by administration of one or more doses of anti-HLA-A2:HPV16E7 antigen-binding proteins of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-HLA-A2:HPV16E7 antigen-binding protein of the invention. For example, intracranial radiation may be administered to a patient with brain cancer (e.g., glioblastoma multiforme) in combination with systemic administration of an anti-HLA-A2:HPV16E7 antigen-binding protein of the invention. In certain embodiments, the anti-HLA-A2:HPV16E7 antigen-binding proteins of the invention may be administered in combination with radiation therapy and a chemotherapeutic agent (e.g., temozolomide) or a VEGF antagonist (e.g., aflibercept).

In certain embodiments, the anti-HLA-A2:HPV16E7 antigen-binding proteins of the invention may be administered in combination with one or more anti-viral drugs to treat chronic HPV infection. Examples of anti-viral drugs include, but are not limited to, zidovudine, lamivudine, abacavir, ribavirin, lopinavir, efavirenz, cobicistat, tenofovir, rilpivirine and corticosteroids.

The additional therapeutically active agent(s)/component(s) may be administered prior to, concurrent with, or after the administration of the anti-HLA-A2:HPV16E7 antigen-binding proteins of the present invention. For purposes of the present disclosure, such administration regimens are considered the administration of an anti-HLA-A2:HPV16E7 antigen-binding protein "in combination with" a second therapeutically active component.

The additional therapeutically active component(s) may be administered to a subject prior to administration of an anti-HLA-A2:HPV16E7 antigen-binding protein of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-HLA-A2:HPV16E7 antigen-binding protein of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-HLA-A2:HPV16E7 antigen-binding protein of the present invention. "Concurrent" administration, for purposes of the present invention, includes, e.g., administration of an anti-HLA-A2:HPV16E7 antigen-binding protein and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-HLA-A2:HPV16E7 antigen-binding protein and the additional therapeutically active component may be administered intravenously, subcutaneously, etc.); alternatively, each dosage form may be administered via a different route (e.g., the anti-HLA-A2:HPV16E7 antigen-binding protein may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-HLA-A2:HPV16E7 antigen-binding protein "prior to", "concurrent with," or "after" (as those terms are defined herein above) administration of an additional therapeutically active component is considered administration of an anti-HLA-A2:HPV16E7 antigen-binding protein "in combination with" an additional therapeutically active component).

The present invention includes pharmaceutical compositions in which an anti-HLA-A2:HPV16E7 antigen-binding protein of the present invention is co-formulated with one or more of the additional therapeutically active component(s) as described elsewhere herein using a variety of dosage combinations.

Administrative Regimens

According to certain embodiments of the present invention, multiple doses of an anti-HLA-A2:HPV16E7 antigen-binding protein (or a pharmaceutical composition comprising a combination of an anti-HLA-A2:HPV16E7 antigen-binding protein and any of the additional therapeutically active agents mentioned herein) may be administered to a subject over a defined time course. The methods according to this aspect of the invention comprise sequentially administering to a subject multiple doses of an anti-HLA-A2:HPV16E7 antigen-binding protein of the invention. As used herein, "sequentially administering" means that each dose of anti-HLA-A2:HPV16E7 antigen-binding protein is administered to the subject at a different point in time, e.g., on different days separated by a predetermined interval (e.g., hours, days, weeks or months). The present invention includes methods which comprise sequentially administering to the patient a single initial dose of an anti-HLA-A2: HPV16E7 antigen-binding protein, followed by one or more secondary doses of the anti-HLA-A2:HPV16E7 antigen-binding protein, and optionally followed by one or more tertiary doses of the anti-HLA-A2:HPV16E7 antigen-binding protein. The anti-HLA-A2:HPV16E7 antigen-binding protein may be administered at a dose between 0.1 mg/kg to 100 mg/kg body weight of the subject.

The terms "initial dose," "secondary doses," and "tertiary doses," refer to the temporal sequence of administration of the anti-HLA-A2:HPV16E7 antigen-binding protein of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-HLA-A2: HPV16E7 antigen-binding protein, but generally may differ from one another in terms of frequency of administration. In certain embodiments, however, the amount of anti-HLA-A2:HPV16E7 antigen-binding protein contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain embodiments, the amount of anti-HLA-A2: HPV16E7 antigen-binding protein contained in the initial, secondary and/or tertiary doses may be sub-optimal or sub-therapeutic. As used herein, the terms "sub-therapeutic" or "sub-optimal" refer to an antibody dose administered at too low a level to produce a therapeutic effect or below the level necessary to treat a disease such as cancer.

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-HLA-A2:HPV16E7 antigen-binding protein which is administered to a patient prior to the administration of the very next dose in the sequence with no intervening doses.

The methods according to this aspect of the invention may comprise administering to a patient any number of secondary and/or tertiary doses of an anti-HLA-A2:HPV16E7 antigen-binding protein. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antigen Binding Proteins

The anti-HLA-A2:HPV16E7 antigen-binding proteins of the present invention may be used to detect and/or measure HPV16E7 in a sample, e.g., for diagnostic purposes. Some embodiments contemplate the use of one or more antigen-binding proteins of the present invention in assays to detect a disease or disorder such as HPV-associated disease or disorder, such as an HPV16E7-positive cancer, or HPV infection. Exemplary diagnostic assays for HPV16E7 may comprise, e.g., contacting a sample, obtained from a subject (e.g., a patient), with an anti-HLA-A2:HPV16E7 antigen-binding protein of the invention, wherein the anti-HLA-A2: HPV16E7 antigen-binding protein is labeled with a detectable label or reporter molecule or used as a capture ligand to selectively isolate HPV16E7 from subject samples. Alternatively, an unlabeled anti-HLA-A2:HPV16E7 antigen-binding protein can be used in diagnostic applications in combination with a secondary antigen-binding protein, e.g., antibody, which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure HPV16E7 in a sample include enzyme-linked immunosorbent assay (ELISA), radioimmunoassay (RIA), and fluorescence-activated cell sorting (FACS).

Samples that can be used in HPV16E7 diagnostic assays according to the present invention include any tissue or fluid sample obtainable from a subject, which contains detectable quantities of either HPV16E7 protein, or fragments thereof, under normal or pathological conditions. Generally, levels of HPV16E7 in a particular sample obtained from a healthy patient (e.g., a patient not afflicted with a HPV16E7-associated disease or disorder, e.g., HPV16E7-positive cancer) will be measured to initially establish a baseline, or standard, level of HPV16E7. This baseline level of HPV16E7 can then be compared against the levels of HPV16E7 measured in samples obtained from individuals suspected of having a cancer-related condition, or symptoms associated with such condition.

The antigen-binding proteins specific for HPV16E7 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antigen-binding proteins as markers for predicting prognosis of HPV16E7-positive cancer or HPV infection in patients. Antigen binding proteins of the present invention may be used in diagnostic assays to evaluate prognosis of cancer in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to HLA-A2:HPV16E7

Human antibodies to HLA-A2:HPV16E7 were generated using peptide fragments of HPV16E7 that include either amino acids 11-19 (YMLDLQPET; SEQ ID NO: 538) of GenBank Accession NP_041326.1 (SEQ ID NO: 537) or amino acid residues 82-90 (LLMGTLGIV; SEQ ID NO: 539) of GenBank Accession NP_041326.1 (SEQ ID NO: 537), coupled to HLA-A2. The immunogen was administered directly, with an adjuvant to stimulate the immune response, to a VELOCIMMUNE® mouse (i.e., an engineered mouse comprising DNA encoding human Immunoglobulin heavy and kappa light chain variable regions), e.g., as described in U.S. Pat. No. 8,502,018. The antibody immune response was monitored by an HLA-A2:HPV16E7-specific immunoassay. When a desired immune response was achieved splenocytes were harvested and fused with mouse myeloma cells to preserve their viability and form hybridoma cell lines. The hybridoma cell lines were screened and selected to identify cell lines that produce HLA-A2:HPV16E7-specific antibodies. Using this technique, and the immunogen described above, several anti-HPV16E7 chimeric antibodies (i.e., antibodies possessing human variable domains and mouse constant domains) were obtained. Exemplary antibodies generated in this manner were designated as follows: H4sH17364N; H4sH17368N2; H4sH17930N; H4sH17930N2; H4sH17363N and H4sH17368N3.

Anti-HLA-A2:HPV16E7 antibodies were also isolated directly from antigen-positive B cells (from either of the immunized mice) without fusion to myeloma cells, as described in U.S. Pat. No. 7,582,298, herein specifically incorporated by reference in its entirety. Using this method, several fully human anti-HLA-A2:HPV16E7 antibodies (i.e., antibodies possessing human variable domains and human constant domains) were obtained.

Exemplary antibodies generated according to the foregoing methods were designated as follows: H4sH17670P; H4sH17672P; H4sH17673P; H4sH17675P; H4sH17680P; H4sH17697P; H4sH17707P; H4sH17715P; H4sH17726P; H4sH17730P; H4sH21051P; H4sH21054P; H4sH21055P; H4sH21058P; H4sH21064P; H4sH21073P; H4sH21077P; H4sH21079P; H4sH21080P; H4sH21083P; H4sH21086P; H4sH21090P; H4sH21091P; H4sH21093P; H4sH21099P; H4sH21100P; H4sH21103P; and H4sH21104P.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-HLA-A2:HPV16E7 antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4sH17364N | 2 | 4 | 6 | 8 | 10 | 12 | 14 | 16 |
| H4sH17368N2 | 18 | 20 | 22 | 24 | 26 | 28 | 30 | 32 |
| H4sH17670P | 34 | 36 | 38 | 40 | 42 | 44 | 46 | 48 |
| H4sH17672P | 50 | 52 | 54 | 56 | 58 | 60 | 62 | 64 |
| H4sH17673P | 66 | 68 | 70 | 72 | 74 | 76 | 78 | 80 |
| H4sH17675P | 82 | 84 | 86 | 88 | 90 | 92 | 94 | 96 |
| H4sH17680P | 98 | 100 | 102 | 104 | 106 | 108 | 110 | 112 |
| H4sH17697P | 114 | 116 | 118 | 120 | 122 | 124 | 126 | 128 |
| H4sH17707P | 130 | 132 | 134 | 136 | 138 | 140 | 142 | 144 |
| H4sH17715P | 146 | 148 | 150 | 152 | 154 | 156 | 158 | 160 |
| H4sH17726P | 162 | 164 | 166 | 168 | 170 | 172 | 174 | 176 |
| H4sH17730P | 178 | 180 | 182 | 184 | 186 | 188 | 190 | 192 |
| H4sH17930N | 210 | 212 | 214 | 216 | 202 | 204 | 206 | 208 |
| H4sH17930N2 | 194 | 196 | 198 | 200 | 202 | 204 | 206 | 208 |
| H4sH21051P | 218 | 220 | 222 | 224 | 226 | 228 | 230 | 232 |
| H4sH21054P | 234 | 236 | 238 | 240 | 242 | 244 | 246 | 248 |
| H4sH21055P | 250 | 252 | 254 | 256 | 258 | 260 | 262 | 264 |
| H4sH21058P | 266 | 268 | 270 | 272 | 274 | 276 | 278 | 280 |
| H4sH21064P | 282 | 284 | 286 | 288 | 290 | 292 | 294 | 296 |
| H4sH21073P | 298 | 300 | 302 | 304 | 306 | 308 | 310 | 312 |
| H4sH21077P | 314 | 316 | 318 | 320 | 322 | 324 | 326 | 328 |
| H4sH21079P | 330 | 332 | 334 | 336 | 338 | 340 | 342 | 344 |
| H4sH21080P | 346 | 348 | 350 | 352 | 354 | 356 | 358 | 360 |
| H4sH21083P | 362 | 364 | 366 | 368 | 370 | 372 | 374 | 376 |
| H4sH21086P | 378 | 380 | 382 | 384 | 386 | 388 | 390 | 392 |
| H4sH21090P | 394 | 396 | 398 | 400 | 402 | 404 | 406 | 408 |
| H4sH21091P | 410 | 412 | 414 | 416 | 418 | 420 | 422 | 424 |
| H4sH21093P | 426 | 428 | 430 | 432 | 434 | 436 | 438 | 440 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4sH21099P | 442 | 444 | 446 | 448 | 450 | 452 | 454 | 456 |
| H4sH21100P | 458 | 460 | 462 | 464 | 466 | 468 | 470 | 472 |
| H4sH21103P | 474 | 476 | 478 | 480 | 482 | 484 | 486 | 488 |
| H4sH21104P | 490 | 492 | 494 | 496 | 498 | 500 | 502 | 504 |
| H4sH17363N | 506 | 508 | 510 | 512 | 514 | 516 | 518 | 520 |
| H4sH17368N3 | 522 | 524 | 526 | 528 | 530 | 532 | 534 | 536 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4sH17364N | 1 | 3 | 5 | 7 | 9 | 11 | 13 | 15 |
| H4sH17368N2 | 17 | 19 | 21 | 23 | 25 | 27 | 29 | 31 |
| H4sH17670P | 33 | 35 | 37 | 39 | 41 | 43 | 45 | 47 |
| H4sH17672P | 49 | 51 | 53 | 55 | 57 | 59 | 61 | 63 |
| H4sH17673P | 65 | 67 | 69 | 71 | 73 | 75 | 77 | 79 |
| H4sH17675P | 81 | 83 | 85 | 87 | 89 | 91 | 93 | 95 |
| H4sH17680P | 97 | 99 | 101 | 103 | 105 | 107 | 109 | 111 |
| H4sH17697P | 113 | 115 | 117 | 119 | 121 | 123 | 125 | 127 |
| H4sH17707P | 129 | 131 | 133 | 135 | 137 | 139 | 141 | 143 |
| H4sH17715P | 145 | 147 | 149 | 151 | 153 | 155 | 157 | 159 |
| H4sH17726P | 161 | 163 | 165 | 167 | 169 | 171 | 173 | 175 |
| H4sH17730P | 177 | 179 | 181 | 183 | 185 | 187 | 189 | 191 |
| H4sH17930N | 209 | 211 | 213 | 215 | 201 | 203 | 205 | 207 |
| H4sH17930N2 | 193 | 195 | 197 | 199 | 201 | 203 | 205 | 207 |
| H4sH21051P | 217 | 219 | 221 | 223 | 225 | 227 | 229 | 231 |
| H4sH21054P | 233 | 235 | 237 | 239 | 241 | 243 | 245 | 247 |
| H4sH21055P | 249 | 251 | 253 | 255 | 257 | 259 | 261 | 263 |
| H4sH21058P | 265 | 267 | 269 | 271 | 273 | 275 | 277 | 279 |
| H4sH21064P | 281 | 283 | 285 | 287 | 289 | 291 | 293 | 295 |
| H4sH21073P | 297 | 299 | 301 | 303 | 305 | 307 | 309 | 311 |
| H4sH21077P | 313 | 315 | 317 | 319 | 321 | 323 | 325 | 327 |
| H4sH21079P | 329 | 331 | 333 | 335 | 337 | 339 | 341 | 343 |
| H4sH21080P | 345 | 347 | 349 | 351 | 353 | 355 | 357 | 359 |
| H4sH21083P | 361 | 363 | 365 | 367 | 369 | 371 | 373 | 375 |
| H4sH21086P | 377 | 379 | 381 | 383 | 385 | 387 | 389 | 391 |
| H4sH21090P | 393 | 395 | 397 | 399 | 401 | 403 | 405 | 407 |
| H4sH21091P | 409 | 411 | 413 | 415 | 417 | 419 | 421 | 423 |
| H4sH21093P | 425 | 427 | 429 | 431 | 433 | 435 | 437 | 439 |
| H4sH21099P | 441 | 443 | 445 | 447 | 449 | 451 | 453 | 455 |
| H4sH21100P | 457 | 459 | 461 | 463 | 465 | 467 | 469 | 471 |
| H4sH21103P | 473 | 475 | 477 | 479 | 481 | 483 | 485 | 487 |
| H4sH21104P | 489 | 491 | 493 | 495 | 497 | 499 | 501 | 503 |
| H4sH17363N | 505 | 507 | 509 | 511 | 513 | 515 | 517 | 519 |
| H4sH17368N3 | 521 | 523 | 525 | 527 | 529 | 531 | 533 | 535 |

Antibodies are typically referred to herein according to the following nomenclature: Fc prefix (e.g. "H1M," "H4sH," "H4H," etc.), followed by a numerical identifier (e.g. "17670," "17930," etc., as shown in Table 1), followed by a "P," "N," or "N2" suffix. Thus, according to this nomenclature, an antibody may be referred to herein as, e.g., "H4sH17670P," "H4sH17930N," "H4sH17368N2," etc. The H4sH and H4H prefixes on the antibody designations used herein indicate the particular Fc region isotype of the antibody. For example, an "H4sH" antibody has a human IgG4 Fc with 2 or more amino acid changes as disclosed in U.S. Patent Publication No. 20140243504 (herein incorporated in its entirety), an "H4H" antibody has a human IgG4 Fc with a serine to proline mutation in the hinge region (S108P), an "H1M" antibody has a mouse IgG1 Fc, and an "H2M" antibody has a mouse IgG2 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

In certain embodiments, selected antibodies with a mouse IgG1 Fc were converted to antibodies with human IgG4 Fc. In certain embodiments, the antibody comprises a human IgG4 Fc with 2 or more amino acid changes as disclosed in U.S. Patent Publication No. 20100331527 (herein incorporated in its entirety). In one embodiment, the IgG4 Fc domain comprises a serine to proline mutation in the hinge region (S108P) to promote dimer stabilization.

Table 3 sets forth the amino acid sequence identifiers of heavy chain and light chain sequences of selected antibodies of the invention.

TABLE 3

Heavy chain and light chain sequence identifiers

| Antibody Designation | SEQ ID NOs: Heavy Chain | Light Chain |
|---|---|---|
| H4sH17363N | 578 | 579 |
| H4sH17364N | 580 | 581 |
| H4sH17670P | 582 | 583 |
| H4sH17675P | 584 | 585 |
| H4sH17930N2 | 586 | 587 |
| H4sH21058P | 588 | 589 |
| H4sH21064P | 590 | 591 |
| H4sH21104P | 592 | 593 |

Example 3: Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each heavy chain variable region (HCVR) and light chain variable region (LCVR) (Table 4).

TABLE 4

| Antibody Designation | HCVR (HPV) $V_H$ | $D_H$ | $J_H$ | LCVR (HPV) $V_H$ | $J_H$ |
|---|---|---|---|---|---|
| H4sH17363N | V3-23 | D6-6 | J6 | V1-39 | J5 |
| H4sH17364N | V3-23 | D6-6 | J6 | V1-39 | J5 |
| H4sH17368N2 | V3-23 | D3-9 | J4 | V1-39 | J5 |
| H4sH17368N3 | V3-23 | D3-9 | J4 | V1-39 | J5 |
| H4sH17670P | V3-64 | D1-26 | J6 | V1-39 | J5 |
| H4sH17672P | V3-64 | D1-26 | J6 | V1-39 | J5 |
| H4sH17673P | V3-23 | D4-11 | J6 | V1-39 | J5 |
| H4sH17675P | V3-64 | D1-26 | J6 | V1-39 | J5 |
| H4sH17680P | V3-23 | D4-23 | J6 | V1-39 | J5 |
| H4sH17697P | V3-11 | D6-13 | J4 | V1-39 | J2 |
| H4sH17707P | V3-23 | D1-20 | J4 | V1-39 | J5 |
| H4sH17715P | V6-1 | D1-7 | J3 | V1-39 | J2 |
| H4sH17726P | V1-18 | D1-7 | J4 | V3-15 | J4 |
| H4sH17730P | V3-11 | D1-7 | J4 | V1-17 | J2 |
| H4sH17930N | V3-64 | D2-2 | J6 | V1-39 | J5 |
| H4sH17930N2 | V3-64 | D2-2 | J6 | V1-39 | J5 |
| H4sH21051P | V3-23 | D7-27 | J4 | V1-39 | J5 |
| H4sH21054P | V3-23 | D1-7 | J4 | V1-39 | J5 |
| H4sH21055P | V3-11 | D7-27 | J2 | V1-39 | J2 |
| H4sH21058P | V3-20 | D2-2 | J5 | V1-39 | J2 |
| H4sH21064P | V3-64 | D6-6 | J6 | V1-39 | J5 |
| H4sH21073P | V3-43 | D6-19 | J3 | V1-39 | J2 |
| H4sH21077P | V3-23 | D6-19 | J3 | V1-39 | J2 |
| H4sH21079P | V3-15 | D1-7 | J4 | V1-39 | J2 |
| H4sH21080P | V3-23 | D1-7 | J6 | V2-28 | J1 |
| H4sH21083P | V3-23 | D1-7 | J2 | V3-15 | J5 |
| H4sH21086P | V3-33 | D2-21 | J6 | V4-1 | J5 |
| H4sH21090P | V3-23 | D1-20 | J4 | V3-15 | J4 |
| H4sH21091P | V3-15 | D6-19 | J6 | V1-17 | J4 |
| H4sH21093P | V3-33 | D3-3 | J3 | V1-6 | J2 |
| H4sH21099P | V3-9 | D1-1 | J6 | V1-39 | J5 |
| H4sH21100P | V3-9 | D1-7 | J3 | V1-39 | J5 |

TABLE 4-continued

| Antibody Designation | HCVR (HPV) $V_H$ | $D_H$ | $J_H$ | LCVR (HPV) $V_H$ | $J_H$ |
|---|---|---|---|---|---|
| H4sH21103P | V3-15 | D1-7 | J4 | V1-39 | J5 |
| H4sH21104P | V3-11 | D3-10 | J3 | V1-39 | J5 |

Example 4: Surface Plasmon Resonance Derived Binding Affinities and Kinetic Constants of Human Monoclonal Anti-HLA-A2:HPV16E7 Monospecific Antibodies Binding affinities and kinetic constants of human anti-HLA-A2/HPV16E7 antibodies were determined via real-time surface plasmon resonance (SPR; Biacore 4000 or Biacore T-200, GE Healthcare Life Sciences, Pittsburgh, Pa.) at 25° C. Antibodies were captured onto a CM5 Biacore sensor surface (GE Healthcare Life Sciences) derivatized via amine coupling with a monoclonal anti-human Fc antibody (GE, #BR-1008-39). Various concentrations of monomeric HLA-A2: HPV16E7 peptide complex containing either the E7:11-19 peptide (SEQ ID NO: 538) or the E7:82-90 peptide (SEQ ID NO: 539) were injected over the anti-HLA-A2: HPV16E7 antibody captured surface at a flow rate of 50 μL/minute (Biacore T-200) or 304/minute (Biacore 4000). Antibody-reagent association was monitored for 4-5 min. and the dissociation was monitored for 10 min. All binding studies were performed in HBS-ET buffer (0.01M HEPES pH 7.4, 0.15M NaCl, 0.05% v/v Surfactant P20).

Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ks}, \text{ and } t1/2 \text{ (min)} = \frac{\ln(s)}{sc + kd}.$$

Binding kinetic parameters for the monospecific anti-HLA-A2:HPV16E7 antibodies to monomeric HLA-A2/HPV16E7 peptide complex are shown below in Tables 5 and 6.

TABLE 5

Biacore binding affinities of anti-HLA-A2/HPV16E7 (11-19) antibodies at 25° C.

| | HLA-A2:HPV16E7(11-19) | | | |
|---|---|---|---|---|
| Antibody | ka (1/Ms) | kd (1/s) | KD (M) | t½ (min) |
| H4sH17670P | 8.16E+04 | 1.43E-03 | 1.75E-08 | 8.1 |
| H4sH17672P | 1.29E+05 | 8.19E-04 | 6.37E-09 | 14.1 |
| H4sH17673P | NB | NB | NB | NB |
| H4sH17675P | 5.99E+04 | 1.38E-03 | 2.31E-08 | 8.4 |
| H4sH17680P | NB | NB | NB | NB |
| H4sH17697P | NB | NB | NB | NB |
| H4sH17707P | NB | NB | NB | NB |
| H4sH17715P | NB | NB | NB | NB |
| H4sH17726P | NB | NB | NB | NB |
| H4sH17730P | NB | NB | NB | NB |
| H4sH17363N | 8.72E+04 | 1.54E-03 | 1.76E-08 | 7.5 |
| H4sH17364N | 8.56E+04 | 1.57E-03 | 1.83E-08 | 7.4 |
| H4sH17368N2 | NB | NB | NB | NB |
| H4sH17368N3 | NB | NB | NB | NB |

TABLE 5-continued

Biacore binding affinities of anti-HLA-
A2/HPV16E7 (11-19) antibodies at 25° C.

| | HLA-A2:HPV16E7(11-19) | | | |
|---|---|---|---|---|
| Antibody | ka (1/Ms) | kd (1/s) | KD (M) | t½ (min) |
| H4sH17930N | 7.84E+04 | 7.96E−04 | 1.02E−08 | 14.5 |
| H4sH17930N2 | 8.28E+04 | 7.92E−04 | 9.57E−09 | 14.6 |
| H4sH21051P | NB | NB | NB | NB |
| H4sH21054P | NB | NB | NB | NB |
| H4sH21055P | NB | NB | NB | NB |
| H4sH21058P | NB | NB | NB | NB |
| H4sH21064P | 5.47E+04 | 7.91E−04 | 1.44E−08 | 14.6 |
| H4sH21073P | NB | NB | NB | NB |
| H4sH21077P | NB | NB | NB | NB |
| H4sH21079P | 3.74E+04 | 1.09E−02 | 2.90E−07 | 1.1 |
| H4sH21080P | 1.79E+05 | 3.90E−02 | 2.18E−07 | 0.3 |
| H4sH21083P | NB | NB | NB | NB |
| H4sH21086P | NB | NB | NB | NB |
| H4sH21090P | NB | NB | NB | NB |
| H4sH21091P | NB | NB | NB | NB |
| H4sH21093P | NB | NB | NB | NB |
| H4sH21099P | NB | NB | NB | NB |
| H4sH21100P | NB | NB | NB | NB |
| H4sH21103P | NB | NB | NB | NB |
| H4sH21104P | NB | NB | NB | NB |

*NB indicates that under experimental conditions, HLA-A2:HPV16E7(11-19) peptide reagent did not bind to the captured anti-HLA-A2:HPV16E7 monoclonal antibody

TABLE 6

Biacore binding affinities of anti-HLA-
A2/HPV16E7 (82-90) antibodies at 25° C.

| | HLA-A2:HPV16E7(82-90) | | | |
|---|---|---|---|---|
| Antibody | ka (1/Ms) | kd (1/s) | KD (M) | t½ (min) |
| H4sH17670P | NB | NB | NB | NB |
| H4sH17672P | NB | NB | NB | NB |
| H4sH17673P | NB | NB | NB | NB |
| H4sH17675P | NB | NB | NB | NB |
| H4sH17680P | NB | NB | NB | NB |
| H4sH17697P | NB | NB | NB | NB |
| H4sH17707P | 7.15E+04 | 3.61E−04 | 5.05E−09 | 32.0 |
| H4sH17715P | 4.58E+04 | 5.68E−04 | 1.24E−08 | 20.3 |
| H4sH17726P | 5.17E+04 | 4.19E−04 | 8.10E−09 | 27.6 |
| H4sH17730P | NB | NB | NB | NB |
| H4sH17363N | NB | NB | NB | NB |
| H4sH17364N | NB | NB | NB | NB |
| H4sH17368N2 | 8.31E+05 | 1.92E−03 | 2.30E−09 | 6.0 |
| H4sH17368N3 | 7.12E+05 | 1.22E−03 | 1.71E−09 | 9.5 |
| H4sH17930N | NB | NB | NB | NB |
| H4sH17930N2 | NB | NB | NB | NB |
| H4sH21051P | 1.37E+04 | 3.31E−04 | 2.41E−08 | 34.9 |
| H4sH21054P | 1.98E+05 | 7.65E−04 | 3.86E−09 | 15.1 |
| H4sH21055P | 1.56E+05 | 1.21E−03 | 7.76E−09 | 9.6 |
| H4sH21058P | 2.46E+05 | 2.60E−04 | 1.06E−09 | 44.5 |
| H4sH21064P | NB | NB | NB | NB |
| H4sH21073P | 5.77E+05 | 1.15E−04 | 2.00E−10 | 100.3 |
| H4sH21077P | NB | NB | NB | NB |
| H4sH21079P | NB | NB | NB | NB |
| H4sH21080P | NB | NB | NB | NB |
| H4sH21083P | 5.38E+04 | 2.12E−04 | 3.94E−09 | 54.5 |
| H4sH21086P | 6.97E+04 | 1.14E−03 | 1.63E−08 | 10.2 |
| H4sH21090P | 8.11E+04 | 1.91E−04 | 2.35E−09 | 60.6 |
| H4sH21091P | 1.74E+05 | 1.46E−04 | 8.42E−10 | 79.1 |
| H4sH21093P | 1.18E+05 | 1.92E−03 | 1.63E−08 | 6.0 |
| H4sH21099P | 1.24E+05 | 9.79E−05 | 7.88E−10 | 118.0 |
| H4sH21100P | 2.90E+05 | 1.82E−04 | 6.26E−10 | 63.5 |
| H4sH21103P | 8.35E+05 | 3.22E−03 | 3.86E−09 | 3.6 |
| H4sH21104P | 4.36E+04 | 2.15E−04 | 4.94E−09 | 53.7 |

*NB indicates that under experimental conditions, HLA-A2:HPV16E7(82-90) peptide reagent did not bind to the captured anti-HLA-A2:HPV16E7 monoclonal antibody The data demonstrate that a majority of the anti-HLA-A2/HPV16E7 antibodies of this invention selectively bound to soluble HLA-A2/HPV16E7 peptide complex, some displaying sub-nanomolar affinity. Some antibodies, however, displayed no binding to the HLA-A2/HPV16E7 complex.

Example 5: Prediction of Potential Off-Target Peptides

Given a target 9-mer peptide-HLA-A2 complex, an associated potential off-target peptide is defined based on three criteria: A) the peptide is a 9-mer and is predicted to bind HLA-A2, B) the peptide is similar to the target peptide based on sequence homology, and C) the peptide is derived from a gene that is expressed in essential, normal tissues. Therefore, to predict potential off-target peptides associated with YMLDLQPET (HPV16 E711-19; SEQ ID NO: 538) and LLMGTLGIV (HPV16 E782-90; SEQ ID NO:539) the following methodology was used (generally see, Dhanik, Ankur, et al. (2016) BMC Bioinformatics 17(1):286).

As a first step, canonical human protein sequences were downloaded from the UniprotKB database (version September 2014) (Magrane, Michele, and UniProt Consortium. Database 2011 (2011): bar009) and all 9-mers were extracted. This resulted in 11,118,076 peptides from 20,014 protein sequences.

Next, the binding affinities of the peptides with HLA-A2 were computed using NetMHCstab webserver (version 1.0) (Jorgensen, Kasper W., et al. (2014) Immunology 141(1): 18-26). Peptides with affinity value <500 nM were predicted to bind HLA-A2, and the rest were discarded resulting in the remaining 338,452 peptides.

The peptide sequences were then evaluated for sequence homology with the target peptide. For each peptide, its Degree of Similarity (DoS) was calculated to the target peptide. The DoS value represents the number of identical amino acids at identical positions between the two peptides. Peptides with DoS value <6 were rejected resulting in the remaining 21 peptides in the case of HLA-A2/HPV16E7: 11-19 and 78 peptides in the case of HLA-A2/HPV16E7: 82-90.

The genes corresponding to the 21 peptides were checked for their expression in the essential, normal tissues. The evaluation for the expression was done using the gene expression data derived from the GTEx (Gene Tissue Expression) and TCGA (The Cancer Genome Atlas) databases as provided by OmicSoft (Hu, Jun, et al. Bioinformatics (2012) 28(14):1933-1934). The data was available in RPKM (Reads Per Kilobase Per Million) values from 497 TCGA adjacent normal samples (across 15 essential tissue types), and 2,928 GTEx normal samples (across 22 essential tissue types). Tissues other than the breast, cervix, fallopian tube, testis, uterus, and vagina, were considered essential. A gene was considered to be expressed in the essential, normal tissues if the maximum of the 95 percentile expression in each essential, normal tissue type in the GTEx and TOGA databases is >=0.5 RPKM. For HLA-A2/HPV16E7:11-19 (YMLDLQPET), out of the 21 peptides, 10 peptides were derived from genes that are expressed in the essential, normal tissues. For HLA-A2/HPV16E7:82-90 (LLMGTLGIV), out of the 78 peptides, 49 peptides were derived from genes that are expressed in the essential, normal tissues.

The 10 peptides constitute the predicted off-targets associated with the target YMLDLQPET-HLA-A2 complex (Table 7). Out of the 49 potential peptides predicted to constitute likely off-targets associated with the LLMGTLGIV-HLA-A2 complex, 13 were picked at random for experimental validation and are listed in Table 8.

TABLE 7

Predicted off-target peptides similar to
HLA-A2/HPV16E7: 11-19 (YMLDLQPET; SEQ ID NO: 538)

| No. | Peptide Sequence | Peptide Name | Gene | Predicted IC50 (nM) |
|---|---|---|---|---|
| 1 | YMLDLQKQL (SEQ ID NO: 546) | SH3GLB1: 244-252 | SH3GLB1 | 9.2 |
| 2 | KMLDKNPET (SEQ ID NO: 547) | CAMKK1: 388-396 | CAMKK1 | 107.9 |
| 3 | YMFDLLLET (SEQ ID NO: 548) | USP47: 691-699 | USP47 | 3.5 |
| 4 | YTLDLQLEA (SEQ ID NO: 549) | CHPF: 463:471 | CHPF | 132.8 |
| 5 | MMLILQAET (SEQ ID NO: 550) | PKD1: 2694-2702 | PKD1 | 244.3 |
| 6 | LMLPLQPCT (SEQ ID NO: 551) | NBR1: 357-365 | NBR1 | 487.8 |
| 7 | YILDLLPDT (SEQ ID NO: 552) | CBL: 83-91 | CBL | 145.9 |
| 8 | YMEDLQELT (SEQ ID NO: 553) | PPP4R4: 20-28 | PPP4R4 | 482.1 |
| 9 | GLLDLDPET (SEQ ID NO: 554) | SBK3: 285-293 | SBK3 | 91.6 |
| 10 | VMKDLLPET (SEQ ID NO: 555) | FNDC3B: 921-929 | FNDC3B | 379.9 |

TABLE 8

Predicted off-target peptides similar to
HLA-A2/HPV16E7: 82-90 (LLMGTLGIV; SEQ ID NO: 539)

| No. | Peptide Sequence | Peptide Name | Gene | Predicted IC50 (nM) |
|---|---|---|---|---|
| 1 | LLMGTFLSV (SEQ ID NO: 556) | VPREB3: 9-17 | VPREB3 | 5.9 |
| 2 | LLGGTLERV (SEQ ID NO: 557) | B4GALT2: 4-12 | B4GALT2 | 93.6 |
| 3 | LLMGSNTIV (SEQ ID NO: 558) | GCAT: 312-320 | GCAT | 13.2 |
| 4 | LLQATLDIV (SEQ ID NO: 559) | CYP39A1: 246-254 | CYP39A1 | 88.7 |
| 5 | LLLTFLGIV (SEQ ID NO: 560) | ALDH3A2: 467-475 | ALDH3A2 | 85.4 |
| 6 | LLAGTLAGV (SEQ ID NO: 561) | CLCN4: 79-87 | CLCN4 | 11.0 |
| 7 | LLQDTLGHV (SEQ ID NO: 562) | ZHX2: 234-242 | ZHX2 | 50.5 |
| 8 | LLLAVLGIV (SEQ ID NO: 563) | GRM6: 590-598 | GRM6 | 64.4 |
| 9 | LVMETLCIV (SEQ ID NO: 564) | IPO9: 582-590 | IPO9 | 18.8 |
| 10 | LLNETLGEV (SEQ ID NO: 565) | IPO4: 163-171 | IPO4 | 25.8 |
| 11 | KLMGHLGVV (SEQ ID NO: 566) | SF3B1: 969-977 | SF3B1 | 11.2 |
| 12 | LLMCYLYIV (SEQ ID NO: 567) | DOCK11: 1282-1290 | DOCK11 | 2.7 |
| 13 | LLNKVLGIV (SEQ ID NO: 568) | Human CNOT1: 1962-1970 | CNOT1 | 247.8 |

Example 6: T2 Peptide Pulsing to Determine HLA-A2/HPV16E7 M Specificity

To determine anti-HLA-A2/HPV16E7 monoclonal antibody specificity, peptide-pulsed T2 cells loaded with target or off-target peptides (identified in the previous Example) were used. Experiments were carried out as follows: For the exogenous loading of HPV16E7 target or off-target peptides, T2 cells were rinsed in AIM V® Medium and counted with a Cellometer™ Auto T4 cell counter (Nexcelom Bioscience). Approximately 6 million T2 cells per T-75 flask were cultured for 24 hours at 26° C. in 9 mL of AIM V® Medium containing 10 μg of human b2 m and 100 μg of HPV16E7 peptide or off-target peptide (Tables 6 and 7). Peptide-loaded T2 cells were washed once with PBS without Ca2+/Mg2+ and counted. Approximately 10,000 cells per well of the peptide-loaded T2 or untreated T2 in cell washing buffer were seeded into the 96-well carbon electrode plates (MULTI-ARRAY high bind plate, MSD) and incubated for 1 hour at 37° C. to allow cells to adhere to the plate. Nonspecific binding sites were blocked using 2% BSA (w/v) in PBS for 1 hour at room temperature. To the plate-bound cells, solutions of anti-HLA-A2/HPV16E7:11-19, anti-HLA-A2/HPV16E7:82-90 or control antibody in serial dilutions ranging from 1.7 pM to 100 nM, as well as solutions without antibody were added. Plates were incubated for 1 hour at room temperature, then washed to remove the unbound antibody using an AquaMax2000 plate washer (MDS Analytical Technologies). Plate-bound antibodies were detected with SULFO-TAG™-conjugated goat polyclonal anti-human IgG antibody specific for the Fc gamma fragment (Jackson Immunoresearch, Meso Scale Discovery) for 1 hour at room temperature. After washes, the plates were developed with the Read Buffer (MSD) according to manufacturer's recommended procedure, and the luminescent signals were recorded with a SECTOR Imager 600 (Meso Scale Discovery) instrument. The luminescence intensity, measured in relative light units (RLU), was recorded to indicate the binding intensity of each antibody at the range of concentrations. The ratio of cell binding signal for each anti-HLA-A2/HPV16E7 antibody compared to isotype control at 11 nM, is reported in Tables 8 and 9 and is an indication of specificity. At 11 nM concentration most antibodies displayed minimal binding to T2 untreated cells. Not all antibodies were tested with all corresponding related off-target peptides. Those not tested are marked as NT for "Not Tested". Antibodies with a binding ratio of greater than 15 are marked (+++), with a ratio equal to or less than 15 but greater than or equal to 10 are marked (++), with a ratio less than 10 but greater than or equal to 3 are marked (+) and antibodies with a binding ratio less than 3 were classified as non-binders and denoted as (−). In addition, direct binding signals (in RLU) were analyzed as a function of the antibody concentration and data fitted to a sigmoidal (four-parameter logistic) dose-response model using GraphPad Prism™. The $EC_{50}$ values, defined as the concentration of antibody at which 50% of the maximal binding signal on cells is detected, were determined, where possible, to indicate potency of each antibody. $EC_{50}$ values for binding to cell-surface HLA-A2/HPV16E7:11-19 or HLA-A2/HPV16E7:82-90 only, are also reported in Tables 9 and 10.

Ten of 13 anti-HLA-A2/HPV16E7:11-19 antibodies of the invention bind to T2 cell-surface HLA-A2/peptide complex. Seven of these 10 antibodies (H4sH17670P; H4sH17675P; H4sH17363N; H4sH17364N; H4sH17930N; H4sH17930N2; and H4sH21064P are specific for the HLA-A2/HPV16E7:11-19 complex. Three antibodies (H4sH17672P, H4sH21079P, H4sH21080P) showed displayed higher potency with $EC_{50}$ values below 1.1 nM. Three antibodies (H4sH17673P, H4sH17680P, H4sH17697P) did not bind to T2 peptide loaded cells and are denoted with a (−) in the first column of Table 9.

The cell binding results on T2 cells loaded with HPV16E7:82-90 target and predicted off-target peptides are summarized in Table 9. Sixteen of 21 anti-HLA-A2/HPV16E7:82-90 mAbs of the invention bound T2 cell-surface HLA-A2/peptide complex. Only 2 mAbs from this group (H4sH17368N2, H4sH21086P) showed specificity to the HLA-A2/HPV16E7 82-90 complex. Five antibodies (H4sH17730P, H4sH21051P, H4sH21054P, H4sH21055P, H4sH21077P) did not bind to T2 peptide loaded cells and are denoted with a (−) in the Table 10.

TABLE 9

Binding Specificity of Anti-HLA-A2/HPV16E7:11-19 Monoclonal Antibodies

| AbPID | Cell Binding EC50 (M) T2 + HPV16E7 11-19 | HPV16E7 11-19 | SH3GLB1 244-252 | CAMKK1 388-396 | USP47 691-699 | CHPF 463:471 | PKD1 2694-2702 | NBR1 357-365 | CBL 83-91 | PPP4R4 20-28 | SBK3 285-293 | T2 untreated |
|---|---|---|---|---|---|---|---|---|---|---|---|---|
| H4sH17670P | 1.3E−09 | ++ | − | − | − | − | − | − | − | − | − | − |
| H4sH17672P | 4.5E−10 | ++ | − | − | + | − | − | − | − | − | − | − |
| H4sH17673P | − | − | − | − | − | − | − | − | − | − | − | − |
| H4sH17675P | 1.1E−09 | + | − | − | − | − | − | − | − | − | − | − |
| H4sH17680P | − | − | − | − | − | − | − | − | − | − | − | − |
| H4sH17697P | − | − | − | − | − | − | − | − | − | − | − | − |
| H4sH17363N | 2.1E−09 | ++ | − | − | − | − | − | − | − | − | − | − |
| H4sH17364N | 2.0E−09 | ++ | − | − | − | − | − | − | − | − | − | − |
| H4sH17930N | 3.1E−09 | ++ | − | − | − | − | − | − | − | − | − | − |
| H4sH17930N2 | 5.8E−09 | ++ | − | − | − | − | − | − | − | − | − | − |
| H4sH21064P | 2.2E−09 | +++ | NT | NT | NT | − | NT | − | − | NT | NT | − |
| H4sH21079P | 1.1E−09 | +++ | NT | NT | NT | + | NT | − | + | NT | NT | − |
| H4sH21080P | 2.2E−10 | ++ | NT | NT | NT | + | NT | − | + | NT | NT | − |
| | | Cell binding signal at 11 nM, RLU | | | | | | | | | | |
| Isotype Ctrl. | − | 1029 | 976 | 772 | 1102 | 1077 | 1123 | 820 | 1104 | 1038 | 945 | 847 |

TABLE 10

Binding Specificity of Anti-HLA-A2/HPV16E7:82-90 Monoclonal Antibodies

| AbPID | Cell Binding EC50 (M) T2 + HPV16E7 82-90 | T2 + peptide cell binding specificity compared to irrelevant hIgG4s isotype control at 11 nM ||||||||
|---|---|---|---|---|---|---|---|---|---|
| | | HPV16E7 82-90 | VPREB3 9-17 | B4GALT2 4-12 | GCAT 312-320 | CYP39A1 246-254 | ALDH3A2 467-475 | CLCN4 79-87 | ZHX2 234-242 |
| H4sH17707P | 2.3E-08 | + | − | − | − | − | − | − | + |
| H4sH17715P | 2.9E-10 | ++ | − | − | − | − | + | − | − |
| H4sH17726P | 4.1E-10 | ++ | +++ | ++ | − | ++ | + | ++ | + |
| H4sH17730P | − | − | − | − | − | − | − | − | − |
| H4sH17368N2 | 7.5E-10 | ++ | − | − | − | − | − | − | − |
| H4sH17368N3 | 1.8E-10 | ++ | − | − | − | − | − | + | − |
| H4sH21051P | − | − | − | − | NT | NT | NT | NT | − |
| H4sH21054P | − | − | − | − | NT | NT | NT | NT | − |
| H4sH21055P | − | − | − | − | NT | NT | NT | NT | − |
| H4sH21077P | − | − | − | − | NT | NT | NT | NT | − |
| H4sH21086P | 5.0E-10 | +++ | − | − | NT | NT | NT | NT | − |
| H4sH21090P | 5.6E-10 | +++ | − | − | NT | NT | NT | NT | +++ |
| H4sH21091P | 1.7E-10 | +++ | − | − | NT | NT | NT | NT | +++ |
| H4sH21093P | 3.0E-10 | ++ | − | − | NT | NT | NT | NT | + |
| H4sH21058P | 1.9E-10 | ++ | − | − | − | − | − | − | − |
| H4sH21073P | 9.0E-11 | ++ | − | − | − | − | − | − | − |
| H4sH21083P | 3.3E-10 | ++ | − | − | − | − | + | − | − |
| H4sH21099P | 8.7E-11 | ++ | − | − | − | − | + | − | − |
| H4sH21100P | 9.6E-11 | ++ | − | − | − | − | − | − | − |
| H4sH21103P | 4.5E-11 | ++ | − | − | − | − | + | − | − |
| H4sH21104P | 4.8E-10 | ++ | − | − | − | + | − | − | − |
| | | Cell binding signal at 11 nM, RLU ||||||||
| Isotype Ctrl. | − | 835 | 871 | 926 | 872 | 562 | 856 | 725 | 797 |

| AbPID | T2 + peptide cell binding specificity compared to irrelevant hIgG4s isotype control at 11 nM |||||||
|---|---|---|---|---|---|---|---|
| | GRM6 590-598 | IPO9 582-590 | IPO4 163-171 | SF3B1 969-977 | DOCK11 1282-1290 | CNOT1 1962-1970 | T2 Non-Pulsed |
| H4sH17707P | − | − | − | − | − | − | − |
| H4sH17715P | ++ | − | − | + | − | + | − |
| H4sH17726P | ++ | + | − | + | + | + | − |
| H4sH17730P | − | − | − | − | − | − | − |
| H4sH17368N2 | − | − | − | − | − | − | − |
| H4sH17368N3 | − | − | − | − | − | − | − |
| H4sH21051P | NT | NT | NT | NT | NT | NT | − |
| H4sH21054P | NT | NT | NT | NT | NT | NT | − |
| H4sH21055P | NT | NT | NT | NT | NT | NT | − |
| H4sH21077P | NT | NT | NT | NT | NT | NT | − |
| H4sH21086P | NT | NT | NT | NT | NT | NT | − |
| H4sH21090P | NT | NT | NT | NT | NT | NT | − |
| H4sH21091P | NT | NT | NT | NT | NT | NT | − |
| H4sH21093P | NT | NT | NT | NT | NT | NT | − |
| H4sH21058P | + | − | − | + | − | − | − |
| H4sH21073P | + | − | − | − | − | − | − |
| H4sH21083P | + | − | − | ++ | − | + | − |
| H4sH21099P | + | − | − | + | − | + | − |
| H4sH21100P | + | − | − | + | − | − | − |
| H4sH21103P | + | ++ | + | +++ | ++ | ++ | − |
| H4sH21104P | − | − | − | + | − | − | − |
| | Cell binding signal at 11 nM, RLU |||||||
| Isotype Ctrl. | 807 | 768 | 1067 | 702 | 776 | 780 | 860 |

As shown in Tables 9 and 10, anti-HLA-A2:HPV16E7 antigen-binding proteins of the invention bound with high specificity only to the specific HPV peptide (SEQ ID No: 538 in Table 9, or to SEQ ID NO: 539 in Table 10) as presented by HLA-A2 and did not bind to any off-target peptides presented by HLA-A2.

Example 7: Binding Specificity Analysis Using Peptide Pulsed T2 Cells & FACS Analysis Relative binding and specificity of HPV16E7 antibodies were accessed by flow cytometry on NIH3T3 cells expressing HLA-A2 complex presenting either HPV 11-19 peptide (3T3/HLA.A2/hB2M/HPV16E7:11-19) or HPV 82-90 peptide (3T3/HLA.A2/hB2M/HPV16E7 (82-90). NIH3T3 cells expressing HLA complex was generated by transfecting human HLA.A2 (accession number P01892), human B2M (accession number NP_004039.1) and an ubiquitin peptide cassette (Lévy F., et al. (1996) *Proceedings of the National Academy of Sciences of the United States of America* 93(10): 4907-4912; Valmori D, et al. (1999) *Journal of Experimental Medicine* 189(6):895-906) comprising either amino acids 11-19 of HPV16E7 (SEQ ID NO: 538) or amino acids 82-90 (SEQ ID NO: 539) (accession number AKI85233) using lipofectomine 2000 (Invitrogen, Cat #11668) followed by selection for at least 2 weeks in 1 µg/ml puromycin, 500 µg/ml G418, and 100 µg/ml hygromycin. To stain, cells were harvested using cell dissociation buffer (Millipore, Cat #S-004-C) and counted. Cells were plated in staining buffer (PBS, without Calcium and Magnesium (Irving 9240)+2% FBS (ATCC 30-2020) at a density of 200,000 cells per well in a 96-well V-Bottom plate and stained with three-fold serial dilutions (1.7 pM-100 nM) of primary antibodies for 30 min. at 4° C. Following primary antibody incubation, cells were washed once in staining buffer, and stained with an Alexa-Flour 647 conjugated secondary antibody (Jackson ImmunoResearch, Cat #109-606-170) at 10 µg/ml for 30 mins at 4° C. Cells were then washed and fixed using a 50% solution of BD Cytofix (BD, Cat #554655) diluted in staining buffer. Samples were run and analyzed on an intelliCyt iQue flow cytometer to calculate mean fluorescence intensity (MFI). MFI values were plotted in Graphpad Prism using a four-parameter logistic equation over a 12-point response curve to calculate $EC_{50}$ values. The secondary antibody alone (i.e. no primary antibody) for each dose-response curve is also included in the analysis as a continuation of the three-fold serial dilution and is represented as the lowest dose. $EC_{50}$ values (M) and max fold binding (fold changed from highest dose to lowest does) are shown in Table 11. Several antibodies specifically bound to either the 3T3/HLA.A2/hB2M/HPV16E7:11-19 or the 3T3/HLA.A2/hB2M/HPV16E7:82-90 cell line. $EC_{50}$ values ranged from 5-500 nM and fold binding ranged from 1.0× to 43.8λ.

TABLE 11

FACS Binding of HPV16E7 antibodies

| Abtibody Designation | 3T3/HLA.A2/hB2M/HPV16E7 (11-19) | | 3T3/HLA.A2/hB2M/HPV16E7 (82-90) | | HEK293 | |
|---|---|---|---|---|---|---|
| | $EC_{50}$ | Max Fold | $EC_{50}$ | Max Fold | $EC_{50}$ | Max Fold |
| *H4sH17363N | 1.40E−08 | 11.4 | ND | 1.7 | ND | 1.3 |
| *H4sH17364N | 2.40E−08 | 11.4 | 2.91E−08 | 2.3 | ND | 1.2 |
| H4sH17368N2 | ND | 1.8 | 1.94E−07 | 9.1 | ND | 1.8 |
| H4sH17368N3 | ND | 1.1 | 3.26E−08 | 6.1 | ND | 1.7 |
| *H4sH17670P | 2.37E−08 | 6.7 | ND | 1.5 | ND | 0.8 |
| H4sH17672P | 3.72E−08 | 10.2 | ND | 1.4 | ND | 1.6 |
| H4sH17673P | ND | 1.8 | ND | 1.3 | ND | 1.6 |
| *H4sH17675P | 1.27E−08 | 5.1 | ND | 1.3 | ND | 0.65 |
| H4sH17680P | ND | 1.5 | ND | 1.1 | ND | 1 |
| H4sH17697P | ND | 1.2 | ND | 1.5 | ND | 1.1 |
| H4sH17707P | ND | 1.5 | ND | 1.8 | ND | 2 |
| H4sH17715P | ND | 1.7 | 6.60E−06 | 6.7 | 3.47E−08 | 3.1 |
| H4sH17726P | 5.20E−08 | 28.11 | 7.19E−08 | 43.8 | ND | 2.0 |
| H4sH17730P | ND | 0.9 | 5.80E−08 | 2.9 | ND | 0.9 |
| H4sH17930N | 1.73E−08 | 13.5 | 6.62E−08 | 10.3 | 1.53E−07 | 4.3 |
| *H4sH17930N2 | 2.78E−08 | 11.4 | 7.48E−08 | 3 | 3.93E−08 | 3 |
| H4sH21051P | ND | 1.2 | ND | 2.0 | ND | 1.2 |
| H4sH21054P | ND | 3.8 | ND | 4.9 | 3.51E−08 | 3.6 |
| H4sH21055P | ND | 1.4 | ND | 1.5 | ND | 1.9 |
| H4sH21058P | ND | 1.3 | 1.01E−08 | 8.6 | ND | 0.9 |
| *H4sH21064P | 2.05E−08 | 12.3 | 6.60E−08 | 2.2 | ND | 0.7 |
| H4sH21073P | ND | 0.9 | 4.09E−08 | 6.5 | ND | 0.9 |
| H4sH21077P | ND | 2.0 | ND | 1.5 | ND | 1.6 |
| H4sH21079P | 4.02−08 | 26.6 | 5.40E−08 | 20.5 | ND | 1.3 |
| H4sH21080P | 3.10E−08 | 11.7 | 2.11E−08 | 7.4 | 5.19E−08 | 4.4 |
| H4sH21083P | ND | 1.5 | 3.31E−09 | 8.5 | ND | 1.4 |
| H4sH21086P | 5.537E−07 | 14.6 | 3.49E−07 | 22 | ND | 1.3 |
| H4sH21090P | ND | 1.6 | 1.85E−09 | 6.25 | ND | 1.1 |
| H4sH21091P | ND | 1.5 | 3.74E−10 | 5.6 | ND | 1.6 |
| H4sH21093P | ND | 1.9 | 2.95E−08 | 3.9 | ND | 1.4 |
| H4sH21099P | ND | 1 | 1.19E−09 | 4.8 | ND | 2 |
| H4sH21100P | 3.55E−08 | 4.4 | 1.19E−08 | 10.3 | ND | 0.7 |

TABLE 11-continued

FACS Binding of HPV16E7 antibodies

| Antibody Designation | 3T3/HLA.A2/hB2M/HPV16E7 (11-19) | | 3T3/HLA.A2/hB2M/HPV16E7 (82-90) | | HEK293 | |
|---|---|---|---|---|---|---|
| | $EC_{50}$ | Max Fold | $EC_{50}$ | Max Fold | $EC_{50}$ | Max Fold |
| H4sH21103P | ND | 1.6 | 9.20E−09 | 6.3 | ND | 1.5 |
| H4sH21104P | ND | 1.6 | 5.481E−09 | 8.5 | ND | 1 |
| Isotype Ctrl | ND | 1 | ND | 1 | ND | 1.2 |

Antibodies with (*) were run together in a separate experiment
ND = $EC_{50}$ Not Determined when max fold binding was less than or equal to 2 fold The specificity of six HPV16E7:11-19 antibodies was further characterized by assessing binding to T2 (174 CEM.T2) cells pulsed with HPV16E7:11-19, HPV16E7:82-90 or predicted off-target peptides (Table 7). To pulse, T2 (174 CEM.T2) were re-suspended in AIM V medium at a density of 1×106 cells/ml (Gibco. Cat #31035-025). Cells were pulsed by adding 10 µg/ml hB2M (EMD Millipore Cat #475828) and 100 µg/ml of the indicated peptide. T2 cells were then incubated overnight at 26° C., washed in staining buffer and stained with the indicated antibodies at a concentration of 10 µg/ml following the protocol described above. WI values were calculated and presented as fold change over unstained cells. Relative binding of the six HPV16E7:11-19 antibodies on T2 cells pulsed with HPV16E7:11-19 range from 986-1200 fold above unstained cells. No significant binding above isotype control was observed on T2 cells pulsed with the other peptides (Table 12).

TABLE 12

FACS Binding of HPV16E7 antibodies to T2 pulsed cells. (Fold change over unstained)

| | HPV16E7:11-19 YMLDLQPET | SH3GLB1 244-252 | CAMKK1 388-396 | USP47 691-699 | CHPF 463:471 | PKD1 2694-2702 | NBR1 357-365 | CBL 83-91 | PPP4R4 20-28 | SBK3 285-293 | Unpulsed Cells |
|---|---|---|---|---|---|---|---|---|---|---|---|
| H4sH17363N | 1001.4 | 13.6 | 2.0 | 0.6 | 7.4 | 1.2 | 3.6 | 19.5 | 6.1 | 0.4 | 8.5 |
| H4sH17364N | 986.1 | 15.2 | 1.0 | 1.3 | 10.9 | 1.0 | 3.0 | 23.9 | 9.0 | 0.8 | 11.7 |
| H4sH17670P | 1005.5 | 3.7 | 2.9 | 5.3 | 3.6 | 3.5 | 2.2 | 2.0 | 2.9 | 2.6 | 5.0 |
| H4sH17675P | 1204.2 | 10.5 | 2.4 | 13.3 | 5.0 | 2.9 | 2.2 | 4.9 | 5.5 | 2.9 | 7.2 |
| H4sH17930N2 | 1166.7 | 28.2 | 2.6 | 8.9 | 7.5 | 3.3 | 3.3 | 4.6 | 7.3 | 3.0 | 6.7 |
| H4sH21064P | 1204.2 | 10.5 | 2.4 | 13.3 | 5.0 | 2.9 | 2.2 | 4.9 | 5.5 | 2.9 | 7.2 |
| Isotype Ctrl | 17.1 | 8.5 | 6.3 | 11.5 | 9.9 | 9.8 | 8.7 | 9.0 | 8.0 | 6.8 | 10.2 |
| Secondary Alone | 14.2 | 3.7 | 5.8 | 5.2 | 4.8 | 4.4 | 3.7 | 4.4 | 4.0 | 4.1 | 6.5 |
| Unstained | 1.0 | 1.0 | 1.0 | 1.0 | 1.0 | 1.0 | 1.0 | 1.0 | 1.0 | 1.0 | 1.0 |

Example 8: Epitope Analysis Using Alanine Scanning Peptides

Alanine scanning was performed to determine which residues in the HPV16E7:11-19 peptide were critical for antibody binding. T2 cells were pulsed with alanine scanning peptides and stained with HPV16E7:11-19 antibodies as described above. The following alanine scanning peptides were used (Table 13).

TABLE 13

Alanine scanning peptides used in the study

| SEQ ID NO: | Peptide | Ala substitution |
|---|---|---|
| 569 | AMLDLQPET | Y11A |
| 570 | YALDLQPET | M12A |
| 571 | YMADLQPET | L13A |
| 572 | YMLALQPET | D14A |
| 573 | YMLDAQPET | L15A |
| 574 | YMLDLAPET | Q16A |
| 575 | YMLDLQAET | P17A |
| 576 | YMLDLQPAT | E18A |
| 577 | YMLDLQPEA | T19A |

Conversion of aspartate 14 to alanine (D14A) and glutamine 16 to alanine (Q16A) drastically reduced antibody binding for all the tested antibodies. Conversion of tyrosine 11 to alanine (Y11A) reduced binding of H4sH17670P, H4sH17675P, H4sH21064P, and H4sH17930N2; but not H4sH17363N or H4sH17364N. Conversion of leucine 13 to alanine (L13A) and proline 17 to alanine (P17A) reduced overall antibody binding (Table 14).

To summarize, D14 and Q16 are critical residues for antibody binding.

TABLE 14

FACS Binding of HPV16E7 antibodies to T2 cells pulsed with alanine scanning peptides

|  | AMLDLQPET (Y11A) | YALDLQPET (M12A) | YMADLQPET (L13A) | YMLALQPET (D14A) | YMLDAQPET (L15A) |
|---|---|---|---|---|---|
| H4sH17363N | 694.8 | 998.5 | 529.9 | 58.2 | 1019.3 |
| H4sH17364N | 708.3 | 997.9 | 489.9 | 69.7 | 1008.4 |
| H4sH17670P | 8.1 | 670.3 | 374.9 | 10.7 | 1062.8 |
| H4sH17675P | 19.0 | 823.8 | 527.2 | 6.3 | 1153.1 |
| H4sH17930N2 | 39.0 | 972.9 | 665.7 | 5.8 | 1245.9 |
| H4sH21064P | 19.0 | 823.8 | 527.2 | 6.3 | 1153.1 |
| Isotype Ctrl | 14.4 | 10.9 | 8.4 | 9.9 | 8.1 |
| Secondary Alone | 9.7 | 6.9 | 4.9 | 6.4 | 6.3 |
| Unstained | 1.0 | 1.0 | 1.0 | 1.0 | 1.0 |

|  | YMLDLAPET (Q16A) | YMLDLQAET (P17A) | YMLDLQPAT (E18A) | YMLDLQPEA (T19) |
|---|---|---|---|---|
| H4sH17363N | 13.3 | 401.8 | 775.7 | 1034.3 |
| H4sH17364N | 13.2 | 384.8 | 756.2 | 1075.7 |
| H4sH17670P | 6.2 | 168.8 | 614.7 | 1150.1 |
| H4sH17675P | 5.8 | 371.1 | 808.3 | 1165.0 |
| H4sH17930N2 | 6.8 | 531.9 | 1035.4 | 1330.3 |
| H4sH21064P | 5.8 | 371.1 | 808.3 | 1165.0 |
| Isotype Ctrl | 9.0 | 8.2 | 9.1 | 9.6 |
| Secondary Alone | 5.5 | 4.6 | 4.5 | 6.5 |
| Unstained | 1.0 | 1.0 | 1.0 | 1.0 |

Example 9: Reformatting HLA-A2/HPV16E7 Antibodies into ScFv for Use in Chimeric Antigen Receptors Six HLA-A2/HPV16E7:11-19 antibodies (17363N, 17364N, 17670P, 17675P, 17930N2 and 21064P) were reformatted into VL-VH single chain variable fragments (ScFv) and placed into a chimeric antigen receptor (CAR) construct that used a CD8α hinge and transmembrane domain, 4-1BB costimulatory domain, and a CD3ζ stimulatory domain (SEQ ID NOs: 540-545). The HLA-A2/HPV16E7:11-19 specific CARs were cloned into a lentiviral expression vector (Lenti-X™ Bicistronic Expression System (Neo), Clontech Cat #632181) and lentiviral particles were generated via the Lenti-X Packaging Single-Shot (VSV-G) system (Clontech Cat #631276) according to manufacturer protocols. Jurkat cells engineered to express an NFAT-luciferase reporter (Jurkat/NFATLuc cl.3C7) were then transduced with the 6 different CAR constructs using RetroNectin® Pre-coated Dishes (Clontech, Cat #T110a) according to manufacturer's protocols. Following selection for at least 2 weeks in 500 μg/ml G418 (Gibco, Cat #11811-098), CAR-T cell lines were generated.

Activity of CAR-T lines was assessed in a CAR-T/Antigen Presenting Cell (APC) bioassay.

To perform the bioassay, 50,000 Jurkat/NFATLuc cl. 3C7 CAR-T cells were added to Thermo-Nunc 96-well white plates (Thermo Scientific, Cat #136101) in 50 μl of assay media (RPMI media with 10% FBS and 1% P/S/G) followed by the addition of a 3-fold serial dilution of APCs (150,000 cells to 200 cells) in 50 μl of assay media. The following APCs were utilized: CASKI (HLA-A2+/HPV16+), CASKI cells overexpressing a single chain version of HLA-A2 presenting the 11-19 or 82-90 peptide, HEK293 (HLA-A2+/HPV16−), or C33a (HLA-A2+/HPV16−). The cell mixture was incubated in a 37° C., 5% C02, humidified incubator for 5 hours. NFAT-Luciferase activity was measured using Promega One-Glo (Cat #E6130) and a Perkin Elmer Envision plate reader. Relative luciferase units (RLU) were generated and plotted in Graphpad Prism using a four-parameter logistic equation over an 8-point response curve to calculate EC50 values. The zero APC condition for each dose-response curve is also included in the analysis as a continuation of the three-fold serial dilution and is represented as the lowest dose. Max fold activation was determined by taking the ratio of the highest RLU on the curve to the lowest. All six HLA-A2/HPV16E7:11-19 CAR-T cell lines were activated by CASKI cells that overexpressed the HPV16E7:11-19 peptide with max fold activations between 2.5-32.3 fold. No CAR-T cell lines were activated by the APCs that overexpressed the HPV16E7:82-90 peptide or HEK293 and C33a cells. Interestingly, one CAR-T cell line, that used the ScFv from antibody 17675P was activated by native CASKI cells with a fold activation of 4.1 and an EC50 of 68654 cells (Table 15).

TABLE 15

Activation of HPV16E7 (11-19) CAR-T's in a CAR-T/APC Bioassay

| | Jurkat/NFATLuc Chimeric Antigen Receptor Construct | | | | | | | | | | |
|---|---|---|---|---|---|---|---|---|---|---|---|
| | 17363N | | 17364N | | 17670P | | 17675P | | 17930N2 | | 21064P | |
| APC | EC50 (cells) | Fold Activation | EC50 (cells) | Fold Activation | EC50 (cells) | Fold Activation | EC50 (cells) | Fold Activation | EC50 (cells) | Fold Activation | EC50 (cells) | Fold Activation |
| CASKI | ND | 0.9 | ND | 1 | ND | 0.8 | 68654 | 4.1 | ND | 0.9 | ND | 1.2 |
| CASKI 11-19 | 5108 | 2.5 | 6632 | 10.4 | 4145 | 8.5 | 9703 | 32.3 | 7885 | 16.8 | 7220 | 20.7 |
| CASKI 82-90 | ND | 0.9 | ND | 1 | ND | 0.9 | ND | 1.5 | ND | 0.7 | ND | 0.9 |

TABLE 15-continued

Activation of HPV16E7 (11-19) CAR-T's in a CAR-T/APC Bioassay

| | Jurkat/NFATLuc Chimeric Antigen Receptor Construct | | | | | | | | | | | |
|---|---|---|---|---|---|---|---|---|---|---|---|---|
| | 17363N | | 17364N | | 17670P | | 17675P | | 17930N2 | | 21064P | |
| APC | EC50 (cells) | Fold Activation | EC50 (cells) | Fold Activation | EC50 (cells) | Fold Activation | EC50 (cells) | Fold Activation | EC50 (cells) | Fold Activation | EC50 (cells) | Fold Activation |
| HEK293 | ND | 0.8 | ND | 0.9 | ND | 0.8 | ND | 0.7 | ND | 0.7 | ND | 0.8 |
| C33a | ND | 0.7 | ND | 1.2 | ND | 0.8 | ND | 0.6 | ND | 0.6 | ND | 0.4 |

ND = EC50 Not Determined when max fold binding was less than or equal to 2-fold

Increasing the amount of HPV16E7:11-19 presented peptide HLA-A2 should result in an increase in the activation of the HLA-HPV16E7:11-19 CARs. It has been reported that interferon gamma can increase antigen presentation by MHC class 1 molecules though up-regulation of the proteasome (Früh K. and Yang Y. (1999) *Curr Opin Immunol.* 11(1):76-81). Based on this observation, it was determined whether wildtype CASKI cells or HEK293 cells pre-treated with interferon gamma could result in increased activation of the CAR-T cell lines. CASKI cells and HEK293 cells were pretreated with 500 units/ml recombinant human IFN-γ (Peprotech Cat #300-02) for 48 hours and then used in the CAR-T/APC bioassay as described above (Table 16). IFNγ pretreated CASKI cells activate all 6 HPV16E7:11-19 CAR-T cell lines with a fold activation ranging from 2.4-10.6

Thermo-Nunc 96 well white plates (Thermo Scientific, Cat #136101) in 50 μL of assay media. Then, 50,000 pulsed T2 cells were added to the plates in 50 μL assay media. The cell mixture was incubated in a 37° C., 5% C02, humidified incubator for 5 hours. NFAT-Luciferase activity was determined using Promega One-Glo™ (Cat #E6130) and a Perkin Elmer Envision plate reader. RLU were plotted in Graphpad Prism using a four-parameter logistic equation over a 12-point response curve to calculate $EC_{50}$ values. The un-pulsed condition for each dose-response curve is also included in the analysis as a continuation of the three-fold serial dilution and is represented as the lowest dose. Max fold activation was determined as described previously. All CAR-T cell lines were activated by T2 cells pulsed with the HPV16E7:11-19 peptide. The Jurkat/NFATLuc CART line

TABLE 16

Activation of HPV16E7 (11-19) CAR-T's in the presence of IFN-γ

| Jurkat/ NFATLuc CART | CASKI | | CASKI + IFN-g | | HEK293 | | HEK293 + IFN-g | |
|---|---|---|---|---|---|---|---|---|
| | $EC_{50}$ (cells) | Max Fold | $EC_{50}$ (cells) | Max Fold | $EC_{50}$ (cells) | Max Fold | $EC_{50}$ (cells) | Max Fold |
| 17363N | ND | 1.0 | 51837 | 2.4 | ND | 1.0 | ND | 0.81 |
| 17364N | ND | 1.0 | 6440 | 5.6 | ND | 0.86 | ND | 0.75 |
| 17670P | ND | 1.0 | 51360 | 2.7 | ND | 0.77 | ND | 0.78 |
| 17675P | 13844 | 1.77 | 64903 | 10.6 | ND | 0.81 | ND | 0.71 |
| 17930N2 | ND | 0.97 | 57186 | 8.1 | ND | 0.75 | ND | 0.71 |
| 21064P | ND | 1.0 | 55863 | 8.97 | ND | 0.8 | ND | 0.7 |

ND = $EC_{50}$ Not Determined when max fold binding was less than or equal to 2-fold To further asses the specificity of the HPV16E7:11-19 CAR-T lines in the luciferase assay, we used T2 cells as the APC and pulsed with predicted off-target peptides (Table 17). Briefly, T2 cells were pulsed with a three-fold serial dilution of the indicated peptides (1.7 μg/ml to 100 ng/ml). Following pulsing, 50,000 CAR-T cells were added to utilizing the ScFv from antibody 17364N was activated non-specifically by T2 cells pulsed with Endophilin-B1 (SH3GLB1:244-252), Chondroitin sulfate synthase 2 (CHPF:463:471) and E3 ubiquitin-protein ligase CBL (CBL:83-91). All other CAR-T cells lines had no significant activation with any off-target peptide.

TABLE 17

Max Fold Activation of HPV16E7 (11-19) CAR-T's against T2 pulsed cells.

| Peptide | Jurkat/NFATLuc Chimeric Antigen Receptor Construct | | | | | |
|---|---|---|---|---|---|---|
| | 17363N | 17364N | 17670P | 17675P | 17930N2 | 21064P |
| | | | Max Fold Activation | | | |
| HPV16E7:11-19 | 6.5 | 10.9 | 1.9 | 10.6 | 7.8 | 12.9 |
| HPV16E7:82-90 | 0.9 | 0.9 | 0.9 | 0.9 | 0.9 | 0.8 |
| SH3GLB1:244-252 | 1.3 | 6.1 | 0.9 | 1.1 | 1.4 | 3.4 |
| CAMKK1:388-396 | 0.9 | 1.0 | 0.9 | 0.9 | 0.9 | 0.8 |
| USP47:691-699 | 1.0 | 0.9 | 0.9 | 1.0 | 0.9 | 1.1 |
| CHPF:463:471 | 1.1 | 5.2 | 0.9 | 1.0 | 0.9 | 1.1 |
| PKD1:2694-2702 | 0.8 | 0.9 | 1.0 | 1.0 | 0.9 | 0.9 |
| NBR1:357-365 | 0.9 | 0.9 | 0.9 | 0.9 | 0.9 | 0.9 |
| CBL:83-91 | 1.3 | 7.2 | 0.9 | 1.1 | 0.9 | 1.5 |
| PPP4R4:20-28 | 0.9 | 0.9 | 1.0 | 1.0 | 0.9 | 0.9 |
| SBK3:285-293 | 1.0 | 0.9 | 1.0 | 1.0 | 0.9 | 0.9 |

Example 10: Structural Analysis of Fab Binding to HLA-A2+HPV16E7:11-19 Peptide

In an effort to better understand the specific interactions between antibody and HLA-peptide complex, X-ray crystal structures of an antibody Fab fragment bound to HLA-A2/b2m displaying the HPV16E7:11-19 peptide were determined. One structure contains the 17670P Fab, and the other structure contains the 17363N Fab; together, these two structures cover the sequence space of the six antibodies presented above (e.g. Table 11 and Table 12). All 9 residues of the HLA-displayed HPV16E7:11-19 peptide are clearly visible in the electron density maps for both 17670P and 17363N structures. Even at 2.9 Å (the resolution of the 17670P structure), the position and identity of the peptide residues is unambiguous, and residue-residue interactions can be determined accurately. The 17363P structure is 2.6 Å, allowing improved accuracy.

The 17670P and 17363N Fabs bind to the top of the HLA-peptide complex, in a manner very similar to the way that TCR binds. The Fabs are positioned and oriented almost identically to each other; both are aligned fairly parallel to the "rails" bordering the peptide binding groove, and both are centered on the bound peptide, with the heavy chain CDRs contacting the N terminal half of the bound peptide, and the light chain CDRs contacting the peptide's C terminal half. Other published antibody complex structures (e.g. PDB codes 1W72 and 4WUU) reveal that the antibody does not have to cover the entire HLA-displayed peptide. However, these antibodies with only partial peptide coverage have poor specificity, tolerating extensive changes in the part of the peptide that is not contacted with little loss in binding affinity.

The structures show that the 17670P and 17363N Fab heavy chains contact residues 11, 14, 15 in the HPV16E7 peptide, while the Fab light chains contact residues 15, 17, 18. No Fab contacts are made with side chains of residues 12, 13, 16, or 19 as they point toward the HLA molecule. The bound peptide is numbered according to the residue positions in the original HPV16 E7 protein, as follows:

```
                                          (SEQ ID NO: 358)
        Y   M   L   D   L   Q   P   E   T
        11  12  13  14  15  16  17  18  19
```

The majority of Fab contacts are made with the peptide side chains, not the backbone.

Peptide contacts made by 17670P are concentrated almost exclusively in CDRs LCDR1 and HCDR3, particularly HCDR3. In particular, Fab heavy chain residues 100, 101, 102, 105, 109, 110 of SEQ ID NO: 34 and light chain residues 30, 31, 32, 50 of SEQ ID NO: 42 make contact with the bound peptide, while Fab heavy chain residues 28, 31, 32, 100, 102, 104, 109, 110, 113 of SEQ ID NO: 34 and light chain residues 31, 50, 52, 53, 54, 55, 92 of SEQ ID NO: 42 contact the HLA. "Contact" here can involve direct or water-mediated hydrogen bonds, charge-charge interactions, or hydrophobic/van der Waals interactions. For 17363N, Fab heavy chain residues 102, 103, 108, 111, 112 of SEQ ID NO: 506 and light chain residues 28, 30, 32, 50, 68 of SEQ ID NO: 514 contact the bound peptide, while Fab heavy chain residues 28, 32, 100, 102, 103, 107, 112 of SEQ ID NO: 506 and light chain residues 31, 49, 50, 51, 52, 53, 55, 92 of SEQ ID NO: 514 contact the HLA molecule.

Of the six anti-HLA-A2:HPV16E7:11-19 antibodies, 17675P is the most similar to 17670P in the CDR sequences that determine peptide binding, with 21064P and 17930N2 also sharing a high degree of similarity in the peptide-binding CDR regions. The key contacts between 17670P and the HLA-peptide complex are mostly conserved in 17675P, 21064P, and 17930N2, thus the binding mode of these antibodies is likely to be the same as that of 17670P.

In contrast, CDR H3 of 17363N has a very different sequence compared to CDR H3 from 17670P, and this sequence difference translates into a structural difference of CDR H3, altering contacts with the HLA-peptide complex in this region. For example, heavy chain Tyr 100 in 17670P contacts Tyr 11 of the bound peptide. The equivalent residue in 17363N is Tyr 102 (this antibody's CDR H3 is two residues longer) and this residue does not contact peptide Tyr 11. Instead, Tyr 102 has reoriented to make contacts with the HLA molecule nearby.

The lead antibody 17364N has a very similar sequence to 17363N, and is identical in all residues contacting the HLA-peptide complex. This antibody should have a binding mode very similar to that of 17363N, and thus different from 17670P, 17675P, 17930N2, and 21064P.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating a subject having an HPV16E7-associated disease or disorder, comprising administering to the subject a therapeutically effective amount of an isolated antigen-binding protein that binds specifically to a conformational epitope of an HLA-A2 presented human papillomavirus (HPV) 16 E7 peptide (HPV16E7 peptide), wherein the conformational epitope comprises one or more amino acids of SEQ ID NO: 537 selected from the group consisting of Y11, D14, L15, P17 and E18, wherein the antigen-binding protein comprises three heavy chain complementarity determining regions (CDRs) (HCDR1, HCDR2 and HCDR3); and three light chain CDRs (LCDR1, LCDR2 and LCDR3), wherein (a) the HCDR1 domain comprises an amino acid sequence having at least 90% amino acid sequence identity to the entire amino acid sequence of an amino acid sequence selected from the group consisting of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524;

(b) the HCDR2 domain comprises an amino acid sequence having at least 90% amino acid sequence identity to the entire amino acid sequence of an amino acid sequence selected from the group consisting of SEQ ID NOs: 6, 22, 38, 54, 70, 86, 102, 118, 134, 150, 166, 182, 198, 214, 222, 238, 254, 270, 286, 302, 318, 334, 350, 366, 382, 414, 430, 446, 462, 478, 494, 510, and 526;

(c) the HCDR3 domain comprises an amino acid sequence having at least 90% amino acid sequence identity to the entire amino acid sequence of an amino acid sequence selected from the group consisting of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528;

(d) the LCDR1 domain comprises an amino acid sequence having at least 90% amino acid sequence identity to the entire amino acid sequence of an amino acid sequence selected from the group consisting of SEQ ID NOs: 12, 28, 44, 60, 76, 92, 108, 124, 140, 156, 172, 188, 204, 204, 228, 244, 260, 276, 292, 308, 324, 340, 356, 372, 388, 404, 420, 436, 452, 468, 484, 500, 516, and 532;

(e) the LCDR2 domain comprises an amino acid sequence having at least 90% amino acid sequence identity to the entire amino acid sequence of an amino acid sequence selected from the group consisting of SEQ ID NOs: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534; and (f) the LCDR3 domain comprises an amino acid sequence having at least 90% amino acid sequence identity to the entire amino acid sequence of an amino acid sequence selected from the group consisting of SEQ ID NOs: 16, 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536, thereby treating the subject.

2. The method of claim 1, wherein the HPV16E7-associated disease or disorder is HPV-associated cancer.

3. The method of claim 2, wherein the HPV-associated cancer is squamous cell carcinoma.

4. The method of claim 3, wherein the HPV-associated cancer is cervical cancer, anogenital cancer, head and neck cancer, or oropharyngeal cancer.

5. The method of claim 1, wherein the antigen-binding protein is administered to the subject in combination with a second therapeutic agent.

6. The method of claim 5, wherein the second therapeutic agent is selected from the group consisting of a PD-1 inhibitor, a CTLA-4 inhibitor, an antibody to a tumor specific antigen, an antibody to a virally-infected-cell antigen, a PD-L1 inhibitor, a CD20 inhibitor, a bispecific antibody against CD20 and CD3, a dietary supplement such as an antioxidant, a VEGF antagonist, a chemotherapeutic agent, a cytotoxic agent, surgery, radiation, a NSAID, a corticosteroid, an anti-HPV vaccine, and any other therapy useful for ameliorating at least one symptom associated with the disease or disorder.

7. The method of claim 1, wherein the antigen-binding protein is administered subcutaneously, intravenously, intradermally, intraperitoneally, orally, intramuscularly or intracranially.

8. The method of claim 1, wherein the antigen-binding protein is administered at a dose of about 0.1 mg/kg of body weight to about 100 mg/kg of body weight of the subject.

9. The method of claim 1, wherein the antigen-binding protein has a property selected from the group consisting of:

(a) binds monomeric HLA-A2:HPV16E7 11-19 (SEQ ID NO:538) peptide with a binding dissociation equilibrium constant ($K_D$) of less than about 20 nM as measured in a surface plasmon resonance assay at 25° C.;

(b) binds monomeric HLA-A2:HPV16E7 82-90 (SEQ ID NO:539) peptide with a binding dissociation equilibrium constant ($K_D$) of less than about 25 nM as measured in a surface plasmon resonance assay at 25° C.;

(c) binds to HLA-A2:HPV16E7 11-19 (SEQ ID NO:538) peptide expressing cells with an $EC_{50}$ less than about 6 nM and do not bind to cells expressing predicted off-target peptides as determined by luminescence assay;

(d) binds to HLA-A2:HPV16E7 82-90 (SEQ ID NO:539) peptide expressing cells with an EC50 less than about 1 nM and do not substantially bind to cells expressing predicted off-target peptides as determined by luminescence assay;

(e) binds to HLA-A2:HPV16E7 11-19 (SEQ ID NO:538) peptide expressing cells with an $EC_{50}$ less than about 30 nM as determined by flow cytometry assay; and (f) binds to HLA-A2:HPV16E7 82-90 (SEQ ID NO:539) peptide expressing cells with an $EC_{50}$ less than about 75 nM as determined by flow cytometry assay.

10. The method of claim 1, wherein the HPV16E7 peptide comprises the amino acid sequence of YMLDLQPET (SEQ ID NO: 538).

11. The method of claim 1, wherein (a) the HCDR1 domain comprises an amino acid sequence having at least 95% amino acid sequence identity to the entire amino acid sequence of an amino acid sequence selected from the group consisting of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524;

(b) the HCDR2 domain comprises an amino acid sequence having at least 95% amino acid sequence identity to the entire amino acid sequence of an amino acid sequence selected from the group consisting of SEQ ID NOs: 6, 22, 38, 54, 70, 86, 102, 118, 134, 150, 166, 182, 198, 214, 222, 238, 254, 270, 286, 302, 318, 334, 350, 366, 382, 414, 430, 446, 462, 478, 494, 510, and 526;

(c) the HCDR3 domain comprises an amino acid sequence having at least 95% amino acid sequence identity to the entire amino acid sequence of an amino acid sequence selected from the group consisting of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528;

(d) the LCDR1 domain comprises an amino acid sequence having at least 95% amino acid sequence identity to the entire amino acid sequence of an amino acid sequence selected from the group consisting of SEQ ID NOs: 12, 28, 44, 60, 76, 92, 108, 124, 140, 156, 172, 188, 204, 204, 228, 244, 260, 276, 292, 308, 324, 340, 356, 372, 388, 404, 420, 436, 452, 468, 484, 500, 516, and 532;

(e) the LCDR2 domain comprises an amino acid sequence having at least 95% amino acid sequence identity to the entire amino acid sequence of an amino acid sequence selected from the group consisting of SEQ ID NOs: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534; and (f) the LCDR3 domain comprises an amino acid sequence having at least 95% amino acid sequence identity to the entire amino acid sequence of an amino acid sequence selected from the group consisting of SEQ ID NOs: 16, 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536.

12. The method of claim 11, wherein
(a) the HCDR1 domain comprises an amino acid sequence having at least 98% amino acid sequence identity to the entire amino acid sequence of an amino acid sequence selected from the group consisting of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524;
(b) the HCDR2 domain comprises an amino acid sequence having at least 98% amino acid sequence identity to the entire amino acid sequence of an amino acid sequence selected from the group consisting of SEQ ID NOs: 6, 22, 38, 54, 70, 86, 102, 118, 134, 150, 166, 182, 198, 214, 222, 238, 254, 270, 286, 302, 318, 334, 350, 366, 382, 414, 430, 446, 462, 478, 494, 510, and 526;
(c) the HCDR3 domain comprises an amino acid sequence having at least 98% amino acid sequence identity to the entire amino acid sequence of an amino acid sequence selected from the group consisting of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528;
(d) the LCDR1 domain comprises an amino acid sequence having at least 98% amino acid sequence identity to the entire amino acid sequence of an amino acid sequence selected from the group consisting of SEQ ID NOs: 12, 28, 44, 60, 76, 92, 108, 124, 140, 156, 172, 188, 204, 204, 228, 244, 260, 276, 292, 308, 324, 340, 356, 372, 388, 404, 420, 436, 452, 468, 484, 500, 516, and 532;
(e) the LCDR2 domain comprises an amino acid sequence having at least 98% amino acid sequence identity to the entire amino acid sequence of an amino acid sequence selected from the group consisting of SEQ ID NOs: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534; and
(f) the LCDR3 domain comprises an amino acid sequence having at least 98% amino acid sequence identity to the entire amino acid sequence of an amino acid sequence selected from the group consisting of SEQ ID NOs: 16, 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536.

13. The method of claim 12, wherein
(a) the HCDR1 domain comprises an amino acid sequence selected from the group consisting of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524;
(b) the HCDR2 domain comprises an amino acid sequence selected from the group consisting of SEQ ID NOs: 6, 22, 38, 54, 70, 86, 102, 118, 134, 150, 166, 182, 198, 214, 222, 238, 254, 270, 286, 302, 318, 334, 350, 366, 382, 414, 430, 446, 462, 478, 494, 510, and 526;
(c) the HCDR3 domain comprises an amino acid sequence selected from the group consisting of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528;
(d) the LCDR1 domain comprises an amino acid sequence selected from the group consisting of SEQ ID NOs: 12, 28, 44, 60, 76, 92, 108, 124, 140, 156, 172, 188, 204, 204, 228, 244, 260, 276, 292, 308, 324, 340, 356, 372, 388, 404, 420, 436, 452, 468, 484, 500, 516, and 532;
(e) the LCDR2 domain comprises an amino acid sequence selected from the group consisting of SEQ ID NOs: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534; and
(f) the LCDR3 domain comprises an amino acid sequence selected from the group consisting of SEQ ID NOs: 16, 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536.

14. The method of claim 13, wherein the HCDR1, HCDR2 HCDR3, LCDR1, LCDR2 and LCDR3 comprise an amino acid sequence set selected from the group consisting of SEQ ID NOs: 4, 6, 8, 12, 14, and 16; 36, 38, 40, 44, 46, and 48; 84, 86, 88, 92, 94, and 96; 196, 198, 200, 204, 206, and 208; 284, 286, 288, 292, 294, and 296; and 508, 510, 512, 516, 518, and 520.

15. The method of claim 13, comprising a heavy chain variable region (HCVR)/light chain variable region (LCVR) (HCVR/LCVR) amino acid sequence pair, wherein the amino acid sequence of the HCVR and the amino acid sequence of the LCVR of each HCVR/LCVR pair are each independently at least 90% identical to the amino acid sequences of an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530.

16. The method of claim 15, wherein the amino acid sequence of the HCVR and the amino acid sequence of the LCVR of each HCVR/LCVR pair are each independently at least 95% identical to the amino acid sequence of an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530.

17. The method of claim 15, wherein the amino acid sequence of the HCVR and the amino acid sequence of the LCVR of each HCVR/LCVR pair are selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530.

18. The method of claim 17, comprising an HCVR/LCVR amino acid sequence pair selected from the group consisting of SEQ ID NOs: 2/10, 34/42, 82/90, 194/202, 282/290, and 506/514.

19. The method of claim 1, wherein the antigen-binding protein is a full-length antibody, a Fab, a Fab', a (Fab')2, an Fv, a single chain Fv (scFv), a T-body construct, or a CAR.

20. The method of claim 19, wherein the antigen-binding protein is a single chain Fv (scFv).

21. The method of claim 1, wherein the antigen-binding protein is a human monoclonal antibody, or antigen-binding fragment thereof.

22. The method of claim 1, wherein the isolated antigen-binding protein that binds to HLA-A2:HPV16E7 is present in a pharmaceutical composition comprising a pharmaceutically acceptable carrier or diluent.

23. A method of treating a subject having an HPV16E7-associated disease or disorder, comprising administering to the subject a therapeutically effective amount of an isolated antigen-binding protein that binds specifically to a conformational epitope of an HLA-A2 presented human papillomavirus (HPV) 16 E7 peptide (HPV16E7 peptide), wherein the isolated antigen-binding protein binds to the same epitope as an antigen-binding protein comprising a heavy chain variable region (HCVR)/light chain variable region (LCVR) (HCVR/LCVR) amino acid sequence pair, wherein the amino acid sequence of the HCVR and the amino acid sequence of the LCVR of each HCVR/LCVR pair are each independently at least 90% identical to the amino acid sequences of an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530, thereby treating the subject.

\* \* \* \* \*

SEQUENCE LISTING

<160> NUMBER OF SEQ ID NOS: 593

<210> SEQ ID NO 1
<211> LENGTH: 381
<212> TYPE: DNA
<213> ORGANISM: Artificial Sequence
<220> FEATURE:
<223> OTHER INFORMATION: synthetic

<400> SEQUENCE: 1

```
gaggtgcagt tgttggagtc tgggggaggc ttggtacagc ctgggggtc cctgagactc      60 tcctgtgcag cctctggatt cacctttagc agttatgcca tgacctgggt ccgccaggct    120
ccagggaagg gactggagtg gtctcagtt attagtggta gtggtagtga aacatactac    180
gcagactccg tgaagggccg gttcaccatc tccagagaca attccaaaaa cacgctgtat    240
ctgcaaatga acagcctgag agccgaagac acggccgtat attactgtgt gaaagattct    300
tcgtatagga gctcgtcgag ggcctactac tactacggaa tggacgtctg gggcctaggg    360
accacggtca ccgtctcctc a                                              381
```

<210> SEQ ID NO 2
<211> LENGTH: 127
<212> TYPE: PRT
<213> ORGANISM: Artificial Sequence
<220> FEATURE:
<223> OTHER INFORMATION: synthetic

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Ser Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Ser Ser Tyr Arg Ser Ser Ser Arg Ala Tyr Tyr Tyr Tyr
            100                 105                 110

Gly Met Asp Val Trp Gly Leu Gly Thr Thr Val Thr Val Ser Ser
        115                 120                 125
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcacct ttagcagtta tgcc                                            24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Tyr Ala
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
attagtggta gtggtagtga aaca                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Gly Ser Gly Ser Glu Thr
1               5

<210> SEQ ID NO 7
<211> LENGTH: 60
<212> TYPE: DNA
<213> ORGANISM: Artificial Sequence
<220> FEATURE:
<223> OTHER INFORMATION: synthetic

<400> SEQUENCE: 7
gtgaaagatt cttcgtatag gagctcgtcg agggcctact actactacgg aatggacgtc   60

<210> SEQ ID NO 8
<211> LENGTH: 20
<212> TYPE: PRT
<213> ORGANISM: Artificial Sequence
<220> FEATURE:
<223> OTHER INFORMATION: synthetic

<400> SEQUENCE: 8

Val Lys Asp Ser Ser Tyr Arg Ser Ser Ser Arg Ala Tyr Tyr Tyr Tyr
1               5                   10                  15

Gly Met Asp Val
            20

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc   60
atcacttgcc gggcaagtca gagcattagc agctatttaa attggtatca acagaaacca  120
gggaaagccc ctaagctcct gatctatgct gtttccattt tgcaaagtgg ggtcccatca  180
aggttcagtg gcagtggatc tgggacagat ttcactctca ccatcagctc tctgcaacct  240
gaagattttg caacttactc ctgtcaacag acttacagta ccectccgat caccttcggc  300 caagggacac gactggagat taaa 324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Thr Tyr Ser Thr Pro Pro
                85                  90                  95

Ile Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat                                              18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgtttcc                                                         9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Val Ser
1

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
caacagactt acagtacccc tccgatcacc                                    30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Thr Tyr Ser Thr Pro Pro Ile Thr
1               5                   10

<210> SEQ ID NO 17
<211> LENGTH: 381
<212> TYPE: DNA
<213> ORGANISM: Artificial Sequence
<220> FEATURE:
<223> OTHER INFORMATION: synthetic

<400> SEQUENCE: 17
gaggtgcagc tattggagtc agggggaggc ttggtacagc cggggggtc cctgagactc     60 tcctgtgcag cctctggatt cacctttagt ggctatgccg tgagctgggt ccgccaggct  120
ccagggaagg gctggagtg gtctcaact attagtggaa gtggtactat cacacattac    180
gtagactccg tgaagggccg gttcaccatc tcccgagaca attccaagaa cacgctgtat  240
ctgcaaatga gcagcctgag agccgaggac acggccatat attactgtgc gagagacccg  300
tattacgatg tttttgactgg ttattataag gaggactact tgactactg gggccaggga  360 accctggtca ccgtctcctc a                                           381

<210> SEQ ID NO 18
<211> LENGTH: 127
<212> TYPE: PRT
<213> ORGANISM: Artificial Sequence
<220> FEATURE:
<223> OTHER INFORMATION: synthetic

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Val Ser Trp Val Arg Gln Ala Pro Gly Lys Gly Leu Glu Trp Val
        35                  40                  45

Ser Thr Ile Ser Gly Ser Gly Thr Ile Thr His Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Ile Tyr Tyr Cys

```
                85                  90                  95
Ala Arg Asp Pro Tyr Tyr Asp Val Leu Thr Gly Tyr Tyr Lys Glu Asp
            100                 105                 110

Tyr Phe Asp Tyr Trp Gly Gln Gly Thr Leu Val Thr Val Ser Ser
        115                 120                 125

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttagtggcta tgcc                                           24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Gly Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagtggaa gtggtactat caca                                           24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Gly Ser Gly Thr Ile Thr
1               5

<210> SEQ ID NO 23
<211> LENGTH: 60
<212> TYPE: DNA
<213> ORGANISM: Artificial Sequence
<220> FEATURE:
<223> OTHER INFORMATION: synthetic

<400> SEQUENCE: 23
gcgagagacc cgtattacga tgttttgact ggttattata aggaggacta ctttgactac   60

<210> SEQ ID NO 24
<211> LENGTH: 20
<212> TYPE: PRT
<213> ORGANISM: Artificial Sequence
<220> FEATURE:
<223> OTHER INFORMATION: synthetic

<400> SEQUENCE: 24
```

Ala Arg Asp Pro Tyr Tyr Asp Val Leu Thr Gly Tyr Tyr Lys Glu Asp
1               5                   10                  15

Tyr Phe Asp Tyr
            20

<210> SEQ ID NO 25
<211> LENGTH: 324
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc      60
atcacttgcc gggcaagtca gagcattagc aactatttaa attggtatca gcagaaacca     120
gggaaagccc ctaagctcct gatctatgct gcattcagct tgcaaactgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Phe Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagcatta gcaactat                                                    18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Ile Ser Asn Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcattc                                                                 9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Phe
1

<210> SEQ ID NO 31
<211> LENGTH: 30
<212> TYPE: DNA
<213> ORGANISM: Artificial Sequence
<220> FEATURE:
<223> OTHER INFORMATION: synthetic

<400> SEQUENCE: 31
caacagagtt acagtaccccc tccgatcacc                                        30

<210> SEQ ID NO 32
<211> LENGTH: 10
<212> TYPE: PRT
<213> ORGANISM: Artificial Sequence
<220> FEATURE:
<223> OTHER INFORMATION: synthetic

<400> SEQUENCE: 32

Gln Gln Ser Tyr Ser Thr Pro Pro Ile Thr
1               5                   10

<210> SEQ ID NO 33
<211> LENGTH: 375
<212> TYPE: DNA
<213> ORGANISM: Artificial Sequence
<220> FEATURE:
<223> OTHER INFORMATION: synthetic

<400> SEQUENCE: 33
gaggtgcagc tggtggagtc tgggggagat tggtccagc ctgggacgtc cctgagactc        60
tcctgtgaag cctctggatt caccttaagt ttctacgcta tgtactgggt ccgccaggct      120
cctgggaagg aactggaact tgtttcaggt attagtggta atgggaaag catgttttat       180 ggaaactctg tgaagggcag attctccatc tccagagaca attccaagaa cacgctgtat      240
cttcaaatgg gcagtgtgag agctgaggac atggctgtgt attactgtgc gagagcctac      300
gctagtggaa actcctactt cttttactac ggtatggacg tctggggcca agggaccacg      360
gtcaccgtct cctca                                                        375

```
<210> SEQ ID NO 34
<211> LENGTH: 125
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Asp Leu Val Gln Pro Gly Thr
1               5                   10                  15

Ser Leu Arg Leu Ser Cys Glu Ala Ser Gly Phe Thr Leu Ser Phe Tyr
            20                  25                  30

Ala Met Tyr Trp Val Arg Gln Ala Pro Gly Lys Glu Leu Glu Leu Val
        35                  40                  45

Ser Gly Ile Ser Gly Asn Gly Glu Ser Met Phe Tyr Gly Asn Ser Val
    50                  55                  60

Lys Gly Arg Phe Ser Ile Ser Arg Asp Asn Ser Lys Asn Thr Leu Tyr
65                  70                  75                  80

Leu Gln Met Gly Ser Val Arg Ala Glu Asp Met Ala Val Tyr Tyr Cys
                85                  90                  95

Ala Arg Ala Tyr Ala Ser Gly Asn Ser Tyr Phe Phe Tyr Tyr Gly Met
            100                 105                 110

Asp Val Trp Gly Gln Gly Thr Thr Val Thr Val Ser Ser
        115                 120                 125

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct taagtttcta cgct                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Leu Ser Phe Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attagtggta atggggaaag catg                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic
```

<400> SEQUENCE: 38

Ile Ser Gly Asn Gly Glu Ser Met
1               5

<210> SEQ ID NO 39
<211> LENGTH: 54
<212> TYPE: DNA
<213> ORGANISM: Artificial Sequence
<220> FEATURE:
<223> OTHER INFORMATION: synthetic

<400> SEQUENCE: 39
gcgagagcct acgctagtgg aaactcctac ttcttttact acggtatgga cgtc        54

<210> SEQ ID NO 40
<211> LENGTH: 18
<212> TYPE: PRT
<213> ORGANISM: Artificial Sequence
<220> FEATURE:
<223> OTHER INFORMATION: synthetic

<400> SEQUENCE: 40

Ala Arg Ala Tyr Ala Ser Gly Asn Ser Tyr Phe Phe Tyr Tyr Gly Met
1               5                   10                  15

Asp Val

<210> SEQ ID NO 41
<211> LENGTH: 324
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccaatt tgcaaagtgg ggtcccatca   180
aggttcagtg gcagtggatc tgggacagat ttcactctca ccatcagcag tctgcaacct   240
gaagattttg caacttacta ctgtcaacag agttacagtg cccccccgat caccttcggc   300
caagggacac gactggagat taaa                                          324

<210> SEQ ID NO 42
<211> LENGTH: 108
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Gly Pro Pro
            85                  90                  95

Ile Thr Phe Gly Gln Gly Thr Arg Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagcatta gcagctat                                                 18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Ser Ile Ser Ser Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcatcc                                                            9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 30
<212> TYPE: DNA
<213> ORGANISM: Artificial Sequence
<220> FEATURE:
<223> OTHER INFORMATION: synthetic

<400> SEQUENCE: 47
caacagagtt acagtggccc cccgatcacc                                    30

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Gln Gln Ser Tyr Ser Gly Pro Pro Ile Thr
1               5                   10

<210> SEQ ID NO 49
<211> LENGTH: 375
<212> TYPE: DNA
<213> ORGANISM: Artificial Sequence
<220> FEATURE:
<223> OTHER INFORMATION: synthetic

<400> SEQUENCE: 49
gaggtgcagc tggtggagtc tgggggaggc ttggtccagc ctggggcgtc cctgagactc    60
tcctgtgaag cctctggatt caccttaagt ttctattcta tgcactgggt ccgccaggct   120
ccagggaggg aattggaata tgtttcaggt attagtggta atggaaataa catatattat   180
agagactctg taaagggcag attcaccatt tctagagaca attccaagaa cacgctgaat   240
cttcaaatgg gcagtgtgag agctgaggat atgggtgttt attactgtgc gagatcctac   300
tctagtggga attcctacaa ctactactac ggaatggacg tctggggcca agggaccacg   360
gtcaccgtct cctca                                                   375

<210> SEQ ID NO 50
<211> LENGTH: 125
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Gly Leu Val Gln Pro Gly Ala
1               5                   10                  15

Ser Leu Arg Leu Ser Cys Glu Ala Ser Gly Phe Thr Leu Ser Phe Tyr
            20                  25                  30

Ser Met His Trp Val Arg Gln Ala Pro Gly Arg Glu Leu Glu Tyr Val
        35                  40                  45

Ser Gly Ile Ser Gly Asn Gly Asn Asn Ile Tyr Tyr Arg Asp Ser Val
    50                  55                  60

Lys Gly Arg Phe Thr Ile Ser Arg Asp Asn Ser Lys Asn Thr Leu Asn
65                  70                  75                  80

Leu Gln Met Gly Ser Val Arg Ala Glu Asp Met Gly Val Tyr Tyr Cys
                85                  90                  95

Ala Arg Ser Tyr Ser Ser Gly Asn Ser Tyr Asn Tyr Tyr Tyr Gly Met
            100                 105                 110

Asp Val Trp Gly Gln Gly Thr Thr Val Thr Val Ser Ser
        115                 120                 125

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct taagtttcta ttct                                          24

<210> SEQ ID NO 52
<211> LENGTH: 8
<212> TYPE: PRT
<213> ORGANISM: Artificial Sequence
<220> FEATURE:

```
<223> OTHER INFORMATION: synthetic

<400> SEQUENCE: 52

Gly Phe Thr Leu Ser Phe Tyr Ser
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagtggta atggaaataa cata                                         24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Gly Asn Gly Asn Asn Ile
1               5

<210> SEQ ID NO 55
<211> LENGTH: 54
<212> TYPE: DNA
<213> ORGANISM: Artificial Sequence
<220> FEATURE:
<223> OTHER INFORMATION: synthetic

<400> SEQUENCE: 55
gcgagatcct actctagtgg gaattcctac aactactact acggaatgga cgtc        54

<210> SEQ ID NO 56
<211> LENGTH: 18
<212> TYPE: PRT
<213> ORGANISM: Artificial Sequence
<220> FEATURE:
<223> OTHER INFORMATION: synthetic

<400> SEQUENCE: 56

Ala Arg Ser Tyr Ser Ser Gly Asn Ser Tyr Asn Tyr Tyr Tyr Gly Met
1               5                   10                  15

Asp Val

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgcat ctgttggaga cagagtcacc    60
atcacttgcc gggcaagtca gaccattagt agctatttaa attggtatca gcagaaacca   120
gggaaagccc ctaagctcct catctatgct gtatccaatt tacaaagtgg ggtcccatca   180
aggttcagtg gcagtggatc tgggacagat ttcactctca ccatcagcag tctgcaacct   240
gaagattttg caacttacta ctgtcaacag agttacagta ccccctcgat caccttcggc   300
```
caagggacac gactggagat taaa                                              324

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagaccatta gtagctat                                                     18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Thr Ile Ser Ser Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgtatcc                                                                9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Val Ser
1

<210> SEQ ID NO 63
<211> LENGTH: 30
<212> TYPE: DNA
<213> ORGANISM: Artificial Sequence
<220> FEATURE:
<223> OTHER INFORMATION: synthetic

<400> SEQUENCE: 63
caacagagtt acagtacccc tccgatcacc                                    30

<210> SEQ ID NO 64
<211> LENGTH: 10
<212> TYPE: PRT
<213> ORGANISM: Artificial Sequence
<220> FEATURE:
<223> OTHER INFORMATION: synthetic

<400> SEQUENCE: 64

Gln Gln Ser Tyr Ser Thr Pro Pro Ile Thr
1               5                   10

<210> SEQ ID NO 65
<211> LENGTH: 381
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttagaacaac cggggggtc cctgagactc      60 tcctgtgcag cctctggatt caccttagc agttatgcca tgacctgggt ccgccaggct    120
ccagggaggg gctggagtg gtctcagtt attagtggtc gtggtgatac tacatactac    180
gcagactccg tgaagggccg gttcactatc tccagagaca attccaaaaa cacgctatat   240
ctgcaaatga acagcctgag agccgaggac acggccgtat attactgtgc gaaagacagt   300
aattatgtta catctcttgg gaattactac tactacggta tagacgtctg gggccaaggg   360
accacggtca ccgtctcctc a                                             381

<210> SEQ ID NO 66
<211> LENGTH: 127
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Glu Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Arg Gly Leu Glu Trp Val
        35                  40                  45

Ser Val Ile Ser Gly Arg Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                      85                  90                  95
Ala Lys Asp Ser Asn Tyr Val Thr Ser Leu Gly Asn Tyr Tyr Tyr Tyr
                 100                 105                 110

Gly Ile Asp Val Trp Gly Gln Gly Thr Thr Val Thr Val Ser Ser
             115                 120                 125
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct ttagcagtta tgcc                                       24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Ser Tyr Ala
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
attagtggtc gtggtgatac taca                                       24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Ser Gly Arg Gly Asp Thr Thr
1               5

<210> SEQ ID NO 71
<211> LENGTH: 60
<212> TYPE: DNA
<213> ORGANISM: Artificial Sequence
<220> FEATURE:
<223> OTHER INFORMATION: synthetic

<400> SEQUENCE: 71
gcgaaagaca gtaattatgt tacatctctt gggaattact actactacgg tatagacgtc    60

<210> SEQ ID NO 72
<211> LENGTH: 20
<212> TYPE: PRT
<213> ORGANISM: Artificial Sequence
<220> FEATURE:
<223> OTHER INFORMATION: synthetic

<400> SEQUENCE: 72

```
Ala Lys Asp Ser Asn Tyr Val Thr Ser Leu Gly Asn Tyr Tyr Tyr
1               5                   10                  15

Gly Ile Asp Val
            20
```

<210> SEQ ID NO 73
<211> LENGTH: 324
<212> TYPE: DNA
<213> ORGANISM: Artificial Sequence
<220> FEATURE:
<223> OTHER INFORMATION: synthetic

<400> SEQUENCE: 73

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75

```
cagagcatta gcagctat                                                  18
```

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Ser Ile Ser Ser Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                            9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
1

<210> SEQ ID NO 79
<211> LENGTH: 30
<212> TYPE: DNA
<213> ORGANISM: Artificial Sequence
<220> FEATURE:
<223> OTHER INFORMATION: synthetic

<400> SEQUENCE: 79
caacagagtt acagtacccc tccgatcacc                                    30

<210> SEQ ID NO 80
<211> LENGTH: 10
<212> TYPE: PRT
<213> ORGANISM: Artificial Sequence
<220> FEATURE:
<223> OTHER INFORMATION: synthetic

<400> SEQUENCE: 80

Gln Gln Ser Tyr Ser Thr Pro Pro Ile Thr
1               5                   10

<210> SEQ ID NO 81
<211> LENGTH: 375
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tgggggaggc ttggtccagc ctggggcgtc cctgagactc    60
tcctgtgaag cctctggatt caccttaagt ttctatgcta tgcactgggt ccgccaggct   120
ccagggaagg aactggaata tgtttcaggt attagtggta atgggaatag catatattat   180
agagactctg taaagggcag attcaccatt tctagagaca attccaagaa cacgctgtat   240
cttcaaatgg gcagtgtggg agctgaggat atggctgtgt attactgtgc gagatcctac   300
tctagtggga actcctacta ctactactac ggaatggacg tctggggcca agggaccacg   360
gtcaccgtct cctca                                                   375

<210> SEQ ID NO 82
<211> LENGTH: 125
<212> TYPE: PRT
<213> ORGANISM: Artificial Sequence
<220> FEATURE:
<223> OTHER INFORMATION: synthetic

<400> SEQUENCE: 82

```
Glu Val Gln Leu Val Glu Ser Gly Gly Leu Val Gln Pro Gly Ala
1               5                   10                  15

Ser Leu Arg Leu Ser Cys Glu Ala Ser Gly Phe Thr Leu Ser Phe Tyr
            20                  25                  30

Ala Met His Trp Val Arg Gln Ala Pro Gly Lys Glu Leu Glu Tyr Val
            35                  40                  45

Ser Gly Ile Ser Gly Asn Gly Asn Ser Ile Tyr Tyr Arg Asp Ser Val
        50                  55                  60

Lys Gly Arg Phe Thr Ile Ser Arg Asp Asn Ser Lys Asn Thr Leu Tyr
65                  70                  75                  80

Leu Gln Met Gly Ser Val Gly Ala Glu Asp Met Ala Val Tyr Tyr Cys
                85                  90                  95

Ala Arg Ser Tyr Ser Ser Gly Asn Ser Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
ggattcacct taagtttcta tgct                                    24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

```
Gly Phe Thr Leu Ser Phe Tyr Ala
1               5
```

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
attagtggta atgggaatag cata                                    24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Gly Asn Gly Asn Ser Ile
1               5

<210> SEQ ID NO 87
<211> LENGTH: 54
<212> TYPE: DNA
<213> ORGANISM: Artificial Sequence
<220> FEATURE:
<223> OTHER INFORMATION: synthetic

<400> SEQUENCE: 87
gcgagatcct actctagtgg gaactcctac tactactact acggaatgga cgtc       54

<210> SEQ ID NO 88
<211> LENGTH: 18
<212> TYPE: PRT
<213> ORGANISM: Artificial Sequence
<220> FEATURE:
<223> OTHER INFORMATION: synthetic

<400> SEQUENCE: 88

Ala Arg Ser Tyr Ser Ser Gly Asn Ser Tyr Tyr Tyr Tyr Gly Met
1               5                   10                  15

Asp Val

<210> SEQ ID NO 89
<211> LENGTH: 324
<212> TYPE: DNA
<213> ORGANISM: Artificial Sequence
<220> FEATURE:
<223> OTHER INFORMATION: synthetic

<400> SEQUENCE: 89
gacatccaga tgacccagtc tccatcctcc ctgtctgcat ctgtaggaga cagaattacc       60
atcacttgcc gggcaagtca gagcattagc agctatttaa attggtatca gcagaaacca      120
gggaaagccc ctaacctcct gatctatgct gcatccaatt tacaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                              324

<210> SEQ ID NO 90
<211> LENGTH: 108
<212> TYPE: PRT
<213> ORGANISM: Artificial Sequence
<220> FEATURE:
<223> OTHER INFORMATION: synthetic

<400> SEQUENCE: 90

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Ile Thr Phe Gly Gln Gly Thr Arg Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagagcatta gcagctat                                                    18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Ser Ile Ser Ser Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gctgcatcc                                                               9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Ala Ser
1

<210> SEQ ID NO 95
<211> LENGTH: 30
<212> TYPE: DNA
<213> ORGANISM: Artificial Sequence
<220> FEATURE:
<223> OTHER INFORMATION: synthetic

<400> SEQUENCE: 95
caacagagtt acagtacccc tccgatcacc                                       30

<210> SEQ ID NO 96
<211> LENGTH: 10
<212> TYPE: PRT
<213> ORGANISM: Artificial Sequence
<220> FEATURE:
<223> OTHER INFORMATION: synthetic

<400> SEQUENCE: 96

```
Gln Gln Ser Tyr Ser Thr Pro Pro Ile Thr
1               5                   10
```

<210> SEQ ID NO 97
<211> LENGTH: 378
<212> TYPE: DNA
<213> ORGANISM: Artificial Sequence
<220> FEATURE:
<223> OTHER INFORMATION: synthetic

<400> SEQUENCE: 97

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaggg gactggagtg ggtctcagtt attagtggca gtgatggtaa cacaaactac   180
gcagactccg tgaagggccg gttcaccatc tccagagaca attccaagaa cacactgttt   240
ctgcaaatga acagcctgag agccgaggac acggccgtat attactgtgc gaaagatgcc   300
cgctacggtg gtaactccca ctactactac tacggtatag acgtctgggg ccaagggacc   360
acggtcaccg tctcctca                                                378
```

<210> SEQ ID NO 98
<211> LENGTH: 126
<212> TYPE: PRT
<213> ORGANISM: Artificial Sequence
<220> FEATURE:
<223> OTHER INFORMATION: synthetic

<400> SEQUENCE: 98

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Val Ile Ser Gly Ser Asp Gly Asn Thr Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Ala Arg Tyr Gly Gly Asn Ser His Tyr Tyr Tyr Tyr Gly
            100                 105                 110

Ile Asp Val Trp Gly Gln Gly Thr Thr Val Thr Val Ser Ser
        115                 120                 125
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggattcacct ttagcagcta tgcc                                          24
```

<210> SEQ ID NO 100
<211> LENGTH: 8
<212> TYPE: PRT
<213> ORGANISM: Artificial Sequence
<220> FEATURE:

<223> OTHER INFORMATION: synthetic

<400> SEQUENCE: 100

Gly Phe Thr Phe Ser Ser Tyr Ala
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
attagtggca gtgatggtaa caca                                              24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Gly Ser Asp Gly Asn Thr
1               5

<210> SEQ ID NO 103
<211> LENGTH: 57
<212> TYPE: DNA
<213> ORGANISM: Artificial Sequence
<220> FEATURE:
<223> OTHER INFORMATION: synthetic

<400> SEQUENCE: 103
gcgaaagatg cccgctacgg tggtaactcc cactactact actacggtat agacgtc          57

<210> SEQ ID NO 104
<211> LENGTH: 19
<212> TYPE: PRT
<213> ORGANISM: Artificial Sequence
<220> FEATURE:
<223> OTHER INFORMATION: synthetic

<400> SEQUENCE: 104

Ala Lys Asp Ala Arg Tyr Gly Gly Asn Ser His Tyr Tyr Tyr Tyr Gly
1               5                   10                  15

Ile Asp Val

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagcacct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                              324

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys His Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagcatta gcagctat                                                     18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Ser Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gctgcatcc                                                               9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ala Ala Ser
1

<210> SEQ ID NO 111
<211> LENGTH: 30
<212> TYPE: DNA
<213> ORGANISM: Artificial Sequence
<220> FEATURE:
<223> OTHER INFORMATION: synthetic

<400> SEQUENCE: 111
caacagagtt acagtacccc tccgatcacc          30

<210> SEQ ID NO 112
<211> LENGTH: 10
<212> TYPE: PRT
<213> ORGANISM: Artificial Sequence
<220> FEATURE:
<223> OTHER INFORMATION: synthetic

<400> SEQUENCE: 112

Gln Gln Ser Tyr Ser Thr Pro Pro Ile Thr
1               5                   10

<210> SEQ ID NO 113
<211> LENGTH: 360
<212> TYPE: DNA
<213> ORGANISM: Artificial Sequence
<220> FEATURE:
<223> OTHER INFORMATION: synthetic

<400> SEQUENCE: 113
caggtgcagc tggtggagtc tgggggaggc ttggtcaagc ctggagggtc cctgagactc     60
tcctgtgcag cctctggatt caccctcagt gactactaca tgagctggat ccgccaggct    120
ccagggaagg gctggagtg gtttcatac attagtagta gtggtattac catatactac      180
gcagactctg tgaagggccg attcaccatc tccagggaca acgccaagaa ctcactgtat    240
ctgcaaatga acagcctgag agccgaggac acggccgtgt attactgtgc gagagatagg    300
tatagtagca gctggtactt tgactactgg ggccaggaa cctggtcac cgtctcctca      360

<210> SEQ ID NO 114
<211> LENGTH: 120
<212> TYPE: PRT
<213> ORGANISM: Artificial Sequence
<220> FEATURE:
<223> OTHER INFORMATION: synthetic

<400> SEQUENCE: 114

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Leu Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ile Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Ser Ser Trp Tyr Phe Asp Tyr Trp Gly Gln
            100                 105                 110

Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggattcaccc tcagtgacta ctac                                          24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Phe Thr Leu Ser Asp Tyr Tyr
1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
attagtagta gtggtattac cata                                          24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Ser Ser Ser Gly Ile Thr Ile
1               5

<210> SEQ ID NO 119
<211> LENGTH: 39
<212> TYPE: DNA
<213> ORGANISM: Artificial Sequence
<220> FEATURE:
<223> OTHER INFORMATION: synthetic

<400> SEQUENCE: 119
gcgagagata ggtatagtag cagctggtac tttgactac                          39

<210> SEQ ID NO 120
<211> LENGTH: 13
<212> TYPE: PRT
<213> ORGANISM: Artificial Sequence
<220> FEATURE:
<223> OTHER INFORMATION: synthetic

<400> SEQUENCE: 120

Ala Arg Asp Arg Tyr Ser Ser Ser Trp Tyr Phe Asp Tyr

<210> SEQ ID NO 121
<211> LENGTH: 321
<212> TYPE: DNA
<213> ORGANISM: Artificial Sequence
<220> FEATURE:
<223> OTHER INFORMATION: synthetic

<400> SEQUENCE: 121

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgtacac ttttggccag   300
gggaccaagc tggagatcaa a                                             321
```

<210> SEQ ID NO 122
<211> LENGTH: 107
<212> TYPE: PRT
<213> ORGANISM: Artificial Sequence
<220> FEATURE:
<223> OTHER INFORMATION: synthetic

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123
cagagcatta gcagctat                                                  18

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

Gln Ser Ile Ser Ser Tyr
1               5

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 gctgcatcc                                                                   9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: synthetic

<400> SEQUENCE: 127
caacagagtt acagtacccc gtacact                                              27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Gln Gln Ser Tyr Ser Thr Pro Tyr Thr
1               5

<210> SEQ ID NO 129
<211> LENGTH: 357
<212> TYPE: DNA
<213> ORGANISM: Artificial Sequence
<220> FEATURE:
<223> OTHER INFORMATION: synthetic

<400> SEQUENCE: 129
gaggtgcagc tggtggagtc tgggggaggc ttggtacagc cggggggtc cctgagactc            60 tcctgtgcag cctctggatt cactttagc agttatggta tgacctgggt ccgccaggct          120
ccagggaagg ggctggagtg gtctcagct attagtgtta gtggtggtac cacatactac          180
gcagactccg tgaagggccg gttcaccatc tccagagaca attccaagaa aatgctgaat         240
ctgcaaatga acagcctgag agccgaggac acggccatat attactgtgc gaaagatgag         300
ggctggaacg actactttga ctactggggc cagggaaccc tggtcaccgt ctcctca            357

<210> SEQ ID NO 130
<211> LENGTH: 119
<212> TYPE: PRT
<213> ORGANISM: Artificial Sequence
<220> FEATURE:

-continued

<223> OTHER INFORMATION: synthetic

<400> SEQUENCE: 130

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Gly Met Thr Trp Val Arg Gln Ala Pro Gly Lys Gly Leu Glu Trp Val
        35                  40                  45
Ser Ala Ile Ser Val Ser Gly Gly Thr Thr Tyr Tyr Ala Asp Ser Val
    50                  55                  60
Lys Gly Arg Phe Thr Ile Ser Arg Asp Asn Ser Lys Lys Met Leu Asn
65                  70                  75                  80
Leu Gln Met Asn Ser Leu Arg Ala Glu Asp Thr Ala Ile Tyr Tyr Cys
                85                  90                  95
Ala Lys Asp Glu Gly Trp Asn Asp Tyr Phe Asp Tyr Trp Gly Gln Gly
            100                 105                 110
Thr Leu Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggattcactt ttagcagtta tggt                                      24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Phe Thr Phe Ser Ser Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
attagtgtta gtggtggtac caca                                      24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Ser Val Ser Gly Gly Thr Thr
1               5

```
<210> SEQ ID NO 135
<211> LENGTH: 36
<212> TYPE: DNA
<213> ORGANISM: Artificial Sequence
<220> FEATURE:
<223> OTHER INFORMATION: synthetic

<400> SEQUENCE: 135
gcgaaagatg agggctggaa cgactacttt gactac                            36

<210> SEQ ID NO 136
<211> LENGTH: 12
<212> TYPE: PRT
<213> ORGANISM: Artificial Sequence
<220> FEATURE:
<223> OTHER INFORMATION: synthetic

<400> SEQUENCE: 136

Ala Lys Asp Glu Gly Trp Asn Asp Tyr Phe Asp Tyr
1               5                   10

<210> SEQ ID NO 137
<211> LENGTH: 324
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                         324

<210> SEQ ID NO 138
<211> LENGTH: 108
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 139
```

```
<211> LENGTH: 18
<212> TYPE: DNA
<213> ORGANISM: Artificial Sequence
<220> FEATURE:
<223> OTHER INFORMATION: synthetic

<400> SEQUENCE: 139
cagagcatta gcagctat                                                 18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Ser Ile Ser Ser Tyr
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gctgcatcc                                                            9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Ala Ala Ser
1

<210> SEQ ID NO 143
<211> LENGTH: 30
<212> TYPE: DNA
<213> ORGANISM: Artificial Sequence
<220> FEATURE:
<223> OTHER INFORMATION: synthetic

<400> SEQUENCE: 143
caacagagtt acagtacccc tccgatcacc                                    30

<210> SEQ ID NO 144
<211> LENGTH: 10
<212> TYPE: PRT
<213> ORGANISM: Artificial Sequence
<220> FEATURE:
<223> OTHER INFORMATION: synthetic

<400> SEQUENCE: 144

Gln Gln Ser Tyr Ser Thr Pro Pro Ile Thr
1               5                   10

<210> SEQ ID NO 145
<211> LENGTH: 378
<212> TYPE: DNA
<213> ORGANISM: Artificial Sequence
<220> FEATURE:
```

<223> OTHER INFORMATION: synthetic

<400> SEQUENCE: 145

```
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
attgattatg cactatctgt gaaaagtcga ataaccatca acccagacac atccaagaac     240
cagttctccc tgcagctgaa ctctgtgact cccgaggaca cggctgtgta ttactgtgca     300
ggaggtatag agtattactg gaactacctt gatgcttttg atatctgggg ccaagggaca     360
atggtcaccg tctcttca                                                   378
```

<210> SEQ ID NO 146
<211> LENGTH: 126
<212> TYPE: PRT
<213> ORGANISM: Artificial Sequence
<220> FEATURE:
<223> OTHER INFORMATION: synthetic

<400> SEQUENCE: 146

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ile Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gly Gly Ile Glu Tyr Tyr Trp Asn Tyr Leu Asp Ala
            100                 105                 110

Phe Asp Ile Trp Gly Gln Gly Thr Met Val Thr Val Ser Ser
        115                 120                 125
```

<210> SEQ ID NO 147
<211> LENGTH: 30
<212> TYPE: DNA
<213> ORGANISM: Artificial Sequence
<220> FEATURE:
<223> OTHER INFORMATION: synthetic

<400> SEQUENCE: 147

```
ggggacagtg tctctagcaa cagtgctgct                                       30
```

<210> SEQ ID NO 148
<211> LENGTH: 10
<212> TYPE: PRT
<213> ORGANISM: Artificial Sequence
<220> FEATURE:
<223> OTHER INFORMATION: synthetic

<400> SEQUENCE: 148

```
Gly Asp Ser Val Ser Ser Asn Ser Ala Ala
1               5                   10
```

<210> SEQ ID NO 149

```
<211> LENGTH: 27
<212> TYPE: DNA
<213> ORGANISM: Artificial Sequence
<220> FEATURE:
<223> OTHER INFORMATION: synthetic

<400> SEQUENCE: 149
acatactaca ggtccaagtg gtatatt                                           27

<210> SEQ ID NO 150
<211> LENGTH: 9
<212> TYPE: PRT
<213> ORGANISM: Artificial Sequence
<220> FEATURE:
<223> OTHER INFORMATION: synthetic

<400> SEQUENCE: 150

Thr Tyr Tyr Arg Ser Lys Trp Tyr Ile
1               5

<210> SEQ ID NO 151
<211> LENGTH: 48
<212> TYPE: DNA
<213> ORGANISM: Artificial Sequence
<220> FEATURE:
<223> OTHER INFORMATION: synthetic

<400> SEQUENCE: 151
gcaggaggta tagagtatta ctggaactac cttgatgctt ttgatatc                    48

<210> SEQ ID NO 152
<211> LENGTH: 16
<212> TYPE: PRT
<213> ORGANISM: Artificial Sequence
<220> FEATURE:
<223> OTHER INFORMATION: synthetic

<400> SEQUENCE: 152

Ala Gly Gly Ile Glu Tyr Tyr Trp Asn Tyr Leu Asp Ala Phe Asp Ile
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaaactcct gatctatgct gcatccagtt tgcaaagtgg ggtcccatca       180
aggttcagtg gcagtggatc tgggacagat ttcactctca ccatcagcag tctgcaacct       240
gaagattttg caatttacta ctgtcaacag agttacagta ccccgatcac cttcggccaa       300
gggaccaagc tggagatcaa a                                                321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Ile Tyr Tyr Cys Gln Gln Ser Tyr Ser Thr Pro Ile
                85                  90                  95

Thr Phe Gly Gln Gly Thr Lys Leu Glu Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagagcatta gcagctat        18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Ser Ile Ser Ser Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcatcc        9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacagagtt acagtacccc gatcacc                                      27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Ser Tyr Ser Thr Pro Ile Thr
1               5

<210> SEQ ID NO 161
<211> LENGTH: 348
<212> TYPE: DNA
<213> ORGANISM: Artificial Sequence
<220> FEATURE:
<223> OTHER INFORMATION: synthetic

<400> SEQUENCE: 161
caggtgcagc tggtgcagtc tggagctgag gtgaagaagc ctggggcctc agtgaaggtc    60
tcctgcaaga cttctggtta caccttaacc agctatggta tcagctgggt gcgacaggcc   120
cctggacaag gcttgagtg gatgggatgg agcagcggtc acaatggtaa cacaaactat    180
gcacagaagc tccagggcag agtcaccatg accgcagaca catccacgag cacagcctac   240
atggacctga ggagcctgag atctgacgac acggccgtgt attactgtgc gactttaact   300
ggaacctttg actactgggg ccagggaacc ctggtcaccg tctcctca                348

<210> SEQ ID NO 162
<211> LENGTH: 116
<212> TYPE: PRT
<213> ORGANISM: Artificial Sequence
<220> FEATURE:
<223> OTHER INFORMATION: synthetic

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ser Ser Gly His Asn Gly Asn Thr Asn Tyr Ala Gln Lys Leu
    50                  55                  60

Gln Gly Arg Val Thr Met Thr Ala Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Thr Leu Thr Gly Thr Phe Asp Tyr Trp Gly Gln Gly Thr Leu Val
            100                 105                 110

Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggttacacct taaccagcta tggt                                   24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Tyr Thr Leu Thr Ser Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
agcagcggtc acaatggtaa caca                                   24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ser Ser Gly His Asn Gly Asn Thr
1               5

<210> SEQ ID NO 167
<211> LENGTH: 27
<212> TYPE: DNA
<213> ORGANISM: Artificial Sequence
<220> FEATURE:
<223> OTHER INFORMATION: synthetic

<400> SEQUENCE: 167
gcgactttaa ctggaacctt tgactac                                27

<210> SEQ ID NO 168
<211> LENGTH: 9
<212> TYPE: PRT
<213> ORGANISM: Artificial Sequence
<220> FEATURE:
<223> OTHER INFORMATION: synthetic

<400> SEQUENCE: 168

Ala Thr Leu Thr Gly Thr Phe Asp Tyr
1               5

<210> SEQ ID NO 169
<211> LENGTH: 324
<212> TYPE: DNA
<213> ORGANISM: Artificial Sequence
<220> FEATURE:
<223> OTHER INFORMATION: synthetic

<400> SEQUENCE: 169

```
gaaatagtga tgacgcagtc tccagccacc ctgtctgtgt ctccagggga aagagccacc    60
ctctcctgca gggccagtca gagtgttagc atcaacctag cctggtacca gcagcaccct   120
ggccaggctc ccaggctcct catctatggt gcaaccacca gggccactgg tatcccagcc   180
aggttcagtg gcagtgggtc tgggacagag ttcactctca ccatcagcag cctgcagtct   240
gaagattttg cagtttatta ctgtcaacag tataataact ggcctgcgct cactttcggc   300
ggagggacca aggtggagat caaa                                          324
```

<210> SEQ ID NO 170
<211> LENGTH: 108
<212> TYPE: PRT
<213> ORGANISM: Artificial Sequence
<220> FEATURE:
<223> OTHER INFORMATION: synthetic

<400> SEQUENCE: 170

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ile Asn
            20                  25                  30

Leu Ala Trp Tyr Gln Gln His Pro Gly Gln Ala Pro Arg Leu Leu Ile
        35                  40                  45

Tyr Gly Ala Thr Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ala
                85                  90                  95

Leu Thr Phe Gly Gly Gly Thr Lys Val Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171

```
cagagtgtta gcatcaac                                                  18
```

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

```
Gln Ser Val Ser Ile Asn
1               5
```

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Gly Ala Thr
1

<210> SEQ ID NO 175
<211> LENGTH: 30
<212> TYPE: DNA
<213> ORGANISM: Artificial Sequence
<220> FEATURE:
<223> OTHER INFORMATION: synthetic

<400> SEQUENCE: 175
caacagtata ataactggcc tgcgctcact                              30

<210> SEQ ID NO 176
<211> LENGTH: 10
<212> TYPE: PRT
<213> ORGANISM: Artificial Sequence
<220> FEATURE:
<223> OTHER INFORMATION: synthetic

<400> SEQUENCE: 176

Gln Gln Tyr Asn Asn Trp Pro Ala Leu Thr
1               5                   10

<210> SEQ ID NO 177
<211> LENGTH: 357
<212> TYPE: DNA
<213> ORGANISM: Artificial Sequence
<220> FEATURE:
<223> OTHER INFORMATION: synthetic

<400> SEQUENCE: 177
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac atttggagta ctggtactac catatactac     180
gcagactctg tgaagggccg attcaccatc tccagggaca cgccaagca ctcactttat      240 ctgcaaatga acagcctgag agccgaggac acggccgtgt attactgtgc gagagagggg     300
ataactggaa ctctctttga ctactggggc cagggaaccc tggtcaccgt ctcctca        357

<210> SEQ ID NO 178
<211> LENGTH: 119
<212> TYPE: PRT
<213> ORGANISM: Artificial Sequence
<220> FEATURE:
<223> OTHER INFORMATION: synthetic

<400> SEQUENCE: 178

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val

```
                35                  40                  45
Ser Tyr Ile Trp Ser Thr Gly Thr Thr Ile Tyr Tyr Ala Asp Ser Val
    50                  55                  60

Lys Gly Arg Phe Thr Ile Ser Arg Asp Asn Ala Lys His Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Thr Gly Thr Leu Phe Asp Tyr Trp Gly Gln Gly
            100                 105                 110

Thr Leu Val Thr Val Ser Ser
        115

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggattcacct tcagtgacta ctac                                          24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Ser Asp Tyr Tyr
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
atttggagta ctggtactac cata                                          24

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Trp Ser Thr Gly Thr Thr Ile
1               5

<210> SEQ ID NO 183
<211> LENGTH: 36
<212> TYPE: DNA
<213> ORGANISM: Artificial Sequence
<220> FEATURE:
<223> OTHER INFORMATION: synthetic

<400> SEQUENCE: 183
gcgagagagg ggataactgg aactctcttt gactac                             36
```

<210> SEQ ID NO 184
<211> LENGTH: 12
<212> TYPE: PRT
<213> ORGANISM: Artificial Sequence
<220> FEATURE:
<223> OTHER INFORMATION: synthetic

<400> SEQUENCE: 184

Ala Arg Glu Gly Ile Thr Gly Thr Leu Phe Asp Tyr
1               5                   10

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgtacac ttttggccag     300
gggaccaagc tggagatcaa a                                               321

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
cagggcatta gaaatgat                                                    18

```
<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

Gln Gly Ile Arg Asn Asp
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 gctgcatcc                                                                  9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Ala Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
ctacagcata atagttaccc gtacact                                             27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Leu Gln His Asn Ser Tyr Pro Tyr Thr
1               5

<210> SEQ ID NO 193
<211> LENGTH: 375
<212> TYPE: DNA
<213> ORGANISM: Artificial Sequence
<220> FEATURE:
<223> OTHER INFORMATION: synthetic

<400> SEQUENCE: 193
gaggtgcagc tggtggagtc tgggggaggc ttggtccagc ctggggggtc cctgagactc          60
tcctgtgcag cctctggatt caccttcagt tactatgctt tgcactgggt ccgccaggct         120
ccagggaagg gactggaata tgtttcagct attagtggta atgggggtag cacatattat         180
gcagactctg tgaagggcag attcaccatc tccagagaca atccatgag cacggtgtat          240
```

```
cttcaagtgg gcagcctgag ggctgaggac atggctgttt attactgtgc gagatcctat    300
gccagttcgt ccgattacca ctactactac ggtatggacg tctggggcca agggaccacg    360
gtcaccgtct cctca                                                     375
```

<210> SEQ ID NO 194
<211> LENGTH: 125
<212> TYPE: PRT
<213> ORGANISM: Artificial Sequence
<220> FEATURE:
<223> OTHER INFORMATION: synthetic

<400> SEQUENCE: 194

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Leu His Trp Val Arg Gln Ala Pro Gly Lys Gly Leu Glu Tyr Val
        35                  40                  45

Ser Ala Ile Ser Gly Asn Gly Gly Ser Thr Tyr Tyr Ala Asp Ser Val
    50                  55                  60

Lys Gly Arg Phe Thr Ile Ser Arg Asp Lys Ser Met Ser Thr Val Tyr
65                  70                  75                  80

Leu Gln Val Gly Ser Leu Arg Ala Glu Asp Met Ala Val Tyr Tyr Cys
                85                  90                  95

Ala Arg Ser Tyr Ala Ser Ser Ser Asp Tyr His Tyr Tyr Gly Met
            100                 105                 110

Asp Val Trp Gly Gln Gly Thr Thr Val Thr Val Ser Ser
        115                 120                 125
```

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195

```
ctggattcac cttcagttac tatg                                            24
```

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

```
Leu Asp Ser Pro Ser Val Thr Met
1               5
```

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197

```
agctattagt ggtaatgggg gtag                                            24
```

<210> SEQ ID NO 198
<211> LENGTH: 5
<212> TYPE: PRT
<213> ORGANISM: Artificial Sequence
<220> FEATURE:
<223> OTHER INFORMATION: synthetic

<400> SEQUENCE: 198

Ser Tyr Trp Trp Gly
1               5

<210> SEQ ID NO 199
<211> LENGTH: 50
<212> TYPE: DNA
<213> ORGANISM: Artificial Sequence
<220> FEATURE:
<223> OTHER INFORMATION: synthetic

<400> SEQUENCE: 199
attactgtgc gagatcctat gccagttcgt ccgattacca ctactactac        50

<210> SEQ ID NO 200
<211> LENGTH: 17
<212> TYPE: PRT
<213> ORGANISM: Artificial Sequence
<220> FEATURE:
<223> OTHER INFORMATION: synthetic

<400> SEQUENCE: 200

Ile Thr Val Arg Asp Pro Met Pro Val Arg Pro Ile Thr Thr Thr Thr
1               5                   10                  15

Thr

<210> SEQ ID NO 201
<211> LENGTH: 324
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaa                                              324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagagcatta gcagctat                                                 18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Ser Ile Ser Ser Tyr
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                            9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
1

<210> SEQ ID NO 207
<211> LENGTH: 30
<212> TYPE: DNA
<213> ORGANISM: Artificial Sequence
<220> FEATURE:
<223> OTHER INFORMATION: synthetic

<400> SEQUENCE: 207
caacagagtt acagtacccc tccgatcacc                                    30

<210> SEQ ID NO 208
<211> LENGTH: 10
<212> TYPE: PRT

```
<213> ORGANISM: Artificial Sequence
<220> FEATURE:
<223> OTHER INFORMATION: synthetic

<400> SEQUENCE: 208

Gln Gln Ser Tyr Ser Thr Pro Pro Ile Thr
1               5                   10

<210> SEQ ID NO 209
<211> LENGTH: 375
<212> TYPE: DNA
<213> ORGANISM: Artificial Sequence
<220> FEATURE:
<223> OTHER INFORMATION: synthetic

<400> SEQUENCE: 209
gaggtgcagc tggtggagtc tgggggaggc ttggtccagc ctggggggtc cctgagactc      60
tcctgtgcag cctctggatt caccttcagt tactatgctt tgcactgggt ccgccaggct     120
ccagggaagg gactggaata tgtttcagct attagtggta atgggggtag cacatattat     180
gcagactctg tgaagggcag attcaccatc tccagagaca aatccatgag cacggtgtat     240
cttcaagtgg gcagcctgag ggctgaggac atggctgttt attactgtgc gagatcctat     300
gccagttcgt ccgattacca ctactactac ggtatggacg tctggggcca agggaccacg     360
gtcaccgtct cctca                                                      375

<210> SEQ ID NO 210
<211> LENGTH: 125
<212> TYPE: PRT
<213> ORGANISM: Artificial Sequence
<220> FEATURE:
<223> OTHER INFORMATION: synthetic

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Leu His Trp Val Arg Gln Ala Pro Gly Lys Gly Leu Glu Tyr Val
        35                  40                  45

Ser Ala Ile Ser Gly Asn Gly Gly Ser Thr Tyr Tyr Ala Asp Ser Val
    50                  55                  60

Lys Gly Arg Phe Thr Ile Ser Arg Asp Lys Ser Met Ser Thr Val Tyr
65                  70                  75                  80

Leu Gln Val Gly Ser Leu Arg Ala Glu Asp Met Ala Val Tyr Tyr Cys
                85                  90                  95

Ala Arg Ser Tyr Ala Ser Ser Ser Asp Tyr His Tyr Tyr Tyr Gly Met
            100                 105                 110

Asp Val Trp Gly Gln Gly Thr Thr Val Thr Val Ser Ser
        115                 120                 125

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggattcacct tcagttacta tgct                                             24
```

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gly Phe Thr Phe Ser Tyr Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
attagtggta atgggggtag caca                                              24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

Ile Ser Gly Asn Gly Gly Ser Thr
1               5

<210> SEQ ID NO 215
<211> LENGTH: 54
<212> TYPE: DNA
<213> ORGANISM: Artificial Sequence
<220> FEATURE:
<223> OTHER INFORMATION: synthetic

<400> SEQUENCE: 215
gcgagatcct atgccagttc gtccgattac cactactact acggtatgga cgtc             54

<210> SEQ ID NO 216
<211> LENGTH: 18
<212> TYPE: PRT
<213> ORGANISM: Artificial Sequence
<220> FEATURE:
<223> OTHER INFORMATION: synthetic

<400> SEQUENCE: 216

Ala Arg Ser Tyr Ala Ser Ser Ser Asp Tyr His Tyr Tyr Tyr Gly Met
1               5                   10                  15

Asp Val

<210> SEQ ID NO 217
<211> LENGTH: 357
<212> TYPE: DNA
<213> ORGANISM: Artificial Sequence
<220> FEATURE:
<223> OTHER INFORMATION: synthetic

<400> SEQUENCE: 217
gaggtgcagc tggtggagtc tgggggaggc ttggtacagc ctggggggtc cctgagactc        60
tcctgtgcag cctctggatt cacctttagc acttatgcca tgagttgggt ccgccaggct       120

```
ccagggatgg ggctggagtg ggtctcaact attagtggtt ttggtggtac cacatactac    180
gcagactccg tgaagggccg gttcaccatc tccagagaca attccaagaa ctcgctgtat    240
ctgcaaatga acagcctgag agccgaagac acggccgtat attactgtac gaaagatgag    300
aactgggaat cccactttga ctactggggc cagggaaccc tggtcaccgt ctcctca       357
```

```
<210> SEQ ID NO 218
<211> LENGTH: 119
<212> TYPE: PRT
<213> ORGANISM: Artificial Sequence
<220> FEATURE:
<223> OTHER INFORMATION: synthetic

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Met Gly Leu Glu Trp Val
        35                  40                  45

Ser Thr Ile Ser Gly Phe Gly Gly Thr Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Lys Asp Glu Asn Trp Glu Ser His Phe Asp Tyr Trp Gly Gln Gly
            100                 105                 110

Thr Leu Val Thr Val Ser Ser
        115
```

```
<210> SEQ ID NO 219
<211> LENGTH: 24
<212> TYPE: DNA
<213> ORGANISM: Artificial Sequence
<220> FEATURE:
<223> OTHER INFORMATION: synthetic

<400> SEQUENCE: 219
ggattcacct ttagcactta tgcc                                            24
```

```
<210> SEQ ID NO 220
<211> LENGTH: 8
<212> TYPE: PRT
<213> ORGANISM: Artificial Sequence
<220> FEATURE:
<223> OTHER INFORMATION: synthetic

<400> SEQUENCE: 220

Gly Phe Thr Phe Ser Thr Tyr Ala
1               5
```

```
<210> SEQ ID NO 221
<211> LENGTH: 24
<212> TYPE: DNA
<213> ORGANISM: Artificial Sequence
<220> FEATURE:
<223> OTHER INFORMATION: synthetic

<400> SEQUENCE: 221
attagtggtt ttggtggtac caca                                            24
```

<210> SEQ ID NO 222
<211> LENGTH: 8
<212> TYPE: PRT
<213> ORGANISM: Artificial Sequence
<220> FEATURE:
<223> OTHER INFORMATION: synthetic

<400> SEQUENCE: 222

Ile Ser Gly Phe Gly Gly Thr Thr
1               5

<210> SEQ ID NO 223
<211> LENGTH: 36
<212> TYPE: DNA
<213> ORGANISM: Artificial Sequence
<220> FEATURE:
<223> OTHER INFORMATION: synthetic

<400> SEQUENCE: 223
acgaaagatg agaactggga atcccacttt gactac                                 36

<210> SEQ ID NO 224
<211> LENGTH: 12
<212> TYPE: PRT
<213> ORGANISM: Artificial Sequence
<220> FEATURE:
<223> OTHER INFORMATION: synthetic

<400> SEQUENCE: 224

Thr Lys Asp Glu Asn Trp Glu Ser His Phe Asp Tyr
1               5                   10

<210> SEQ ID NO 225
<211> LENGTH: 324
<212> TYPE: DNA
<213> ORGANISM: Artificial Sequence
<220> FEATURE:
<223> OTHER INFORMATION: synthetic

<400> SEQUENCE: 225
gacatccaga tgacccagtc tccatcctcc ctgtctgcat ctgtaggaga cagagtcacc        60
atcacttgcc gggcaagtca gaccattagc agctatttaa attggtatca gcagaaacca       120
gggaaagccc ctaagctcct gatctatgct acatccagtt tacaaagtgg ggtcccatca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaa                                              324

<210> SEQ ID NO 226
<211> LENGTH: 108
<212> TYPE: PRT
<213> ORGANISM: Artificial Sequence
<220> FEATURE:
<223> OTHER INFORMATION: synthetic

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Thr Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105
```

<210> SEQ ID NO 227
<211> LENGTH: 18
<212> TYPE: DNA
<213> ORGANISM: Artificial Sequence
<220> FEATURE:
<223> OTHER INFORMATION: synthetic

<400> SEQUENCE: 227
cagaccatta gcagctat                                              18

<210> SEQ ID NO 228
<211> LENGTH: 6
<212> TYPE: PRT
<213> ORGANISM: Artificial Sequence
<220> FEATURE:
<223> OTHER INFORMATION: synthetic

<400> SEQUENCE: 228

```
Gln Thr Ile Ser Ser Tyr
 1               5
```

<210> SEQ ID NO 229
<211> LENGTH: 9
<212> TYPE: DNA
<213> ORGANISM: Artificial Sequence
<220> FEATURE:
<223> OTHER INFORMATION: synthetic

<400> SEQUENCE: 229 gctacatcc                                                         9

<210> SEQ ID NO 230
<211> LENGTH: 3
<212> TYPE: PRT
<213> ORGANISM: Artificial Sequence
<220> FEATURE:
<223> OTHER INFORMATION: synthetic

<400> SEQUENCE: 230

```
Ala Thr Ser
 1
```

<210> SEQ ID NO 231
<211> LENGTH: 30
<212> TYPE: DNA
<213> ORGANISM: Artificial Sequence
<220> FEATURE:
<223> OTHER INFORMATION: synthetic

<400> SEQUENCE: 231
caacagagtt acagtacccc tccgatcacc                                 30

<210> SEQ ID NO 232
<211> LENGTH: 10
<212> TYPE: PRT
<213> ORGANISM: Artificial Sequence
<220> FEATURE:
<223> OTHER INFORMATION: synthetic

<400> SEQUENCE: 232

Gln Gln Ser Tyr Ser Thr Pro Pro Ile Thr
1               5                   10

<210> SEQ ID NO 233
<211> LENGTH: 357
<212> TYPE: DNA
<213> ORGANISM: Artificial Sequence
<220> FEATURE:
<223> OTHER INFORMATION: synthetic

<400> SEQUENCE: 233
gaggtgcagc tggtggagtc tgggggaggc ttggtacagc ctgggggtc cctgagactc      60 tcctgtgcag cctctggatt cacctttaac acctatgcca tgacctgggt ccgccaggct     120
ccagggaagg gctggagtg gtctcagaa attagtggtt atggtggtac cacatactac       180
gcagactccg tgaagggccg gttcaccatc tccagagaca attccaagaa cacgctgtat     240
ttgcaaatga acagcctgag agccgaagac acggccgtat attactgtgc gaaagacgaa     300
aactggaact cacactttga ctactggggc cagggaaccc tggtcaccgt ctcctca        357

<210> SEQ ID NO 234
<211> LENGTH: 119
<212> TYPE: PRT
<213> ORGANISM: Artificial Sequence
<220> FEATURE:
<223> OTHER INFORMATION: synthetic

<400> SEQUENCE: 234

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Thr Trp Val Arg Gln Ala Pro Gly Lys Gly Leu Glu Trp Val
        35                  40                  45

Ser Glu Ile Ser Gly Tyr Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Asn Trp Asn Ser His Phe Asp Tyr Trp Gly Gln Gly
            100                 105                 110

Thr Leu Val Thr Val Ser Ser
        115

<210> SEQ ID NO 235
<211> LENGTH: 24
<212> TYPE: DNA
<213> ORGANISM: Artificial Sequence
<220> FEATURE:
<223> OTHER INFORMATION: synthetic

<400> SEQUENCE: 235
ggattcacct ttaacaccta tgcc                                            24

<210> SEQ ID NO 236
<211> LENGTH: 8

```
<212> TYPE: PRT
<213> ORGANISM: Artificial Sequence
<220> FEATURE:
<223> OTHER INFORMATION: synthetic

<400> SEQUENCE: 236

Gly Phe Thr Phe Asn Thr Tyr Ala
1               5

<210> SEQ ID NO 237
<211> LENGTH: 24
<212> TYPE: DNA
<213> ORGANISM: Artificial Sequence
<220> FEATURE:
<223> OTHER INFORMATION: synthetic

<400> SEQUENCE: 237
attagtggtt atggtggtac caca                                          24

<210> SEQ ID NO 238
<211> LENGTH: 8
<212> TYPE: PRT
<213> ORGANISM: Artificial Sequence
<220> FEATURE:
<223> OTHER INFORMATION: synthetic

<400> SEQUENCE: 238

Ile Ser Gly Tyr Gly Gly Thr Thr
1               5

<210> SEQ ID NO 239
<211> LENGTH: 36
<212> TYPE: DNA
<213> ORGANISM: Artificial Sequence
<220> FEATURE:
<223> OTHER INFORMATION: synthetic

<400> SEQUENCE: 239
gcgaaagacg aaaactggaa ctcacacttt gactac                             36

<210> SEQ ID NO 240
<211> LENGTH: 12
<212> TYPE: PRT
<213> ORGANISM: Artificial Sequence
<220> FEATURE:
<223> OTHER INFORMATION: synthetic

<400> SEQUENCE: 240

Ala Lys Asp Glu Asn Trp Asn Ser His Phe Asp Tyr
1               5                   10

<210> SEQ ID NO 241
<211> LENGTH: 327
<212> TYPE: DNA
<213> ORGANISM: Artificial Sequence
<220> FEATURE:
<223> OTHER INFORMATION: synthetic

<400> SEQUENCE: 241
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
```

```
caagggacac gactggagat taaacga                                              327
```

<210> SEQ ID NO 242
<211> LENGTH: 109
<212> TYPE: PRT
<213> ORGANISM: Artificial Sequence
<220> FEATURE:
<223> OTHER INFORMATION: synthetic

<400> SEQUENCE: 242

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg
            100                 105
```

<210> SEQ ID NO 243
<211> LENGTH: 18
<212> TYPE: DNA
<213> ORGANISM: Artificial Sequence
<220> FEATURE:
<223> OTHER INFORMATION: synthetic

<400> SEQUENCE: 243

```
cagagcatta gcagctat                                                         18
```

<210> SEQ ID NO 244
<211> LENGTH: 6
<212> TYPE: PRT
<213> ORGANISM: Artificial Sequence
<220> FEATURE:
<223> OTHER INFORMATION: synthetic

<400> SEQUENCE: 244

```
Gln Ser Ile Ser Ser Tyr
1               5
```

<210> SEQ ID NO 245
<211> LENGTH: 9
<212> TYPE: DNA
<213> ORGANISM: Artificial Sequence
<220> FEATURE:
<223> OTHER INFORMATION: synthetic

<400> SEQUENCE: 245

```
gctgcatcc                                                                    9
```

<210> SEQ ID NO 246
<211> LENGTH: 3
<212> TYPE: PRT
<213> ORGANISM: Artificial Sequence
<220> FEATURE:
<223> OTHER INFORMATION: synthetic

<400> SEQUENCE: 246

Ala Ala Ser
1

<210> SEQ ID NO 247
<211> LENGTH: 30
<212> TYPE: DNA
<213> ORGANISM: Artificial Sequence
<220> FEATURE:
<223> OTHER INFORMATION: synthetic

<400> SEQUENCE: 247
caacagagtt acagtacccc tccgatcacc                                    30

<210> SEQ ID NO 248
<211> LENGTH: 10
<212> TYPE: PRT
<213> ORGANISM: Artificial Sequence
<220> FEATURE:
<223> OTHER INFORMATION: synthetic

<400> SEQUENCE: 248

Gln Gln Ser Tyr Ser Thr Pro Pro Ile Thr
1               5                   10

<210> SEQ ID NO 249
<211> LENGTH: 360
<212> TYPE: DNA
<213> ORGANISM: Artificial Sequence
<220> FEATURE:
<223> OTHER INFORMATION: synthetic

<400> SEQUENCE: 249
caggtgcagc tggtggagtc tgggggaggc ttggtcaagc ctggagggtc cctgagactc     60
tcctgtgcag cctctggatt caccttcagt gacaactaca tgagctggat ccgccaggct    120
ccagggaagg ggctggagtg ggtttcatat attagtagta gtggtagtat catatactac    180
gcagactctg tgaagggccg attcaccatc tccagggaca acgccaagaa ctcactgtat    240
ctgcaaatga acagcctgag agccgaggac acggccatat attactgtgc gagaggcgga    300
tggggatggg actggtactt cgatctctgg ggccgtggca ccctggtcac tgtctcctca    360

<210> SEQ ID NO 250
<211> LENGTH: 120
<212> TYPE: PRT
<213> ORGANISM: Artificial Sequence
<220> FEATURE:
<223> OTHER INFORMATION: synthetic

<400> SEQUENCE: 250

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Trp Gly Trp Asp Trp Tyr Phe Asp Leu Trp Gly Arg
            100                 105                 110

Gly Thr Leu Val Thr Val Ser Ser
        115                 120

<210> SEQ ID NO 251
<211> LENGTH: 24
<212> TYPE: DNA
<213> ORGANISM: Artificial Sequence
<220> FEATURE:
<223> OTHER INFORMATION: synthetic

<400> SEQUENCE: 251
ggattcacct tcagtgacaa ctac                                      24

<210> SEQ ID NO 252
<211> LENGTH: 8
<212> TYPE: PRT
<213> ORGANISM: Artificial Sequence
<220> FEATURE:
<223> OTHER INFORMATION: synthetic

<400> SEQUENCE: 252

Gly Phe Thr Phe Ser Asp Asn Tyr
1               5

<210> SEQ ID NO 253
<211> LENGTH: 24
<212> TYPE: DNA
<213> ORGANISM: Artificial Sequence
<220> FEATURE:
<223> OTHER INFORMATION: synthetic

<400> SEQUENCE: 253
attagtagta gtggtagtat cata                                      24

<210> SEQ ID NO 254
<211> LENGTH: 8
<212> TYPE: PRT
<213> ORGANISM: Artificial Sequence
<220> FEATURE:
<223> OTHER INFORMATION: synthetic

<400> SEQUENCE: 254

Ile Ser Ser Ser Gly Ser Ile Ile
1               5

<210> SEQ ID NO 255
<211> LENGTH: 39
<212> TYPE: DNA
<213> ORGANISM: Artificial Sequence
<220> FEATURE:
<223> OTHER INFORMATION: synthetic

<400> SEQUENCE: 255
gcgagaggcg gatggggatg ggactggtac ttcgatctc                      39

<210> SEQ ID NO 256
<211> LENGTH: 13
<212> TYPE: PRT
<213> ORGANISM: Artificial Sequence
<220> FEATURE:
<223> OTHER INFORMATION: synthetic

<400> SEQUENCE: 256

Ala Arg Gly Gly Trp Gly Trp Asp Trp Tyr Phe Asp Leu
1               5                   10

<210> SEQ ID NO 257
<211> LENGTH: 324
<212> TYPE: DNA
<213> ORGANISM: Artificial Sequence
<220> FEATURE:
<223> OTHER INFORMATION: synthetic

<400> SEQUENCE: 257
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacca agctggagat caaa                                            324

<210> SEQ ID NO 258
<211> LENGTH: 108
<212> TYPE: PRT
<213> ORGANISM: Artificial Sequence
<220> FEATURE:
<223> OTHER INFORMATION: synthetic

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Leu Glu Ile Lys
            100                 105

<210> SEQ ID NO 259
<211> LENGTH: 18
<212> TYPE: DNA
<213> ORGANISM: Artificial Sequence
<220> FEATURE:
<223> OTHER INFORMATION: synthetic

<400> SEQUENCE: 259
cagagcatta gcagctat                                                    18

<210> SEQ ID NO 260
<211> LENGTH: 6
<212> TYPE: PRT
<213> ORGANISM: Artificial Sequence
<220> FEATURE:
<223> OTHER INFORMATION: synthetic

<400> SEQUENCE: 260

Gln Ser Ile Ser Ser Tyr

<210> SEQ ID NO 261
<211> LENGTH: 9
<212> TYPE: DNA
<213> ORGANISM: Artificial Sequence
<220> FEATURE:
<223> OTHER INFORMATION: synthetic

<400> SEQUENCE: 261 gctgcatcc                                                                 9

<210> SEQ ID NO 262
<211> LENGTH: 3
<212> TYPE: PRT
<213> ORGANISM: Artificial Sequence
<220> FEATURE:
<223> OTHER INFORMATION: synthetic

<400> SEQUENCE: 262

Ala Ala Ser
1

<210> SEQ ID NO 263
<211> LENGTH: 30
<212> TYPE: DNA
<213> ORGANISM: Artificial Sequence
<220> FEATURE:
<223> OTHER INFORMATION: synthetic

<400> SEQUENCE: 263
caacagagtt acagtacccc tccgatcacc                                         30

<210> SEQ ID NO 264
<211> LENGTH: 10
<212> TYPE: PRT
<213> ORGANISM: Artificial Sequence
<220> FEATURE:
<223> OTHER INFORMATION: synthetic

<400> SEQUENCE: 264

Gln Gln Ser Tyr Ser Thr Pro Pro Ile Thr
1               5                   10

<210> SEQ ID NO 265
<211> LENGTH: 372
<212> TYPE: DNA
<213> ORGANISM: Artificial Sequence
<220> FEATURE:
<223> OTHER INFORMATION: synthetic

<400> SEQUENCE: 265
gaggtgcagc tggtggagtc tgggggaaat gtggtacggc ctgggggtc cctgagactc         60 tcctgtgcag cctctggatt cacctttgat gattatggca tgagctgggt ccgccaagct       120
ccagggaagg ggctggagtg ggtctctggt attaattgga tggtgatag cacaaattat       180 gcagactctg tgaagggccg attcaccatc tccagagaca acgccaagaa ctccctgtat       240
ctgcaaatga acagtctgag agccgaggac acggccttgt atcactgtgc gagagcgggg       300
attgtagtag actggaatta cgcgggctgg ttcgacccct ggggccaggg aaccctggtc       360
accgtctcct ca                                                           372

<210> SEQ ID NO 266
<211> LENGTH: 124

```
<212> TYPE: PRT
<213> ORGANISM: Artificial Sequence
<220> FEATURE:
<223> OTHER INFORMATION: synthetic

<400> SEQUENCE: 266

Glu Val Gln Leu Val Glu Ser Gly Gly Asn Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Asp Ser Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Ala Gly Ile Val Val Asp Trp Asn Tyr Ala Gly Trp Phe Asp
            100                 105                 110

Pro Trp Gly Gln Gly Thr Leu Val Thr Val Ser Ser
        115                 120

<210> SEQ ID NO 267
<211> LENGTH: 24
<212> TYPE: DNA
<213> ORGANISM: Artificial Sequence
<220> FEATURE:
<223> OTHER INFORMATION: synthetic

<400> SEQUENCE: 267
ggattcacct ttgatgatta tggc                                          24

<210> SEQ ID NO 268
<211> LENGTH: 8
<212> TYPE: PRT
<213> ORGANISM: Artificial Sequence
<220> FEATURE:
<223> OTHER INFORMATION: synthetic

<400> SEQUENCE: 268

Gly Phe Thr Phe Asp Asp Tyr Gly
1               5

<210> SEQ ID NO 269
<211> LENGTH: 24
<212> TYPE: DNA
<213> ORGANISM: Artificial Sequence
<220> FEATURE:
<223> OTHER INFORMATION: synthetic

<400> SEQUENCE: 269
attaattgga atggtgatag caca                                          24

<210> SEQ ID NO 270
<211> LENGTH: 8
<212> TYPE: PRT
<213> ORGANISM: Artificial Sequence
<220> FEATURE:
<223> OTHER INFORMATION: synthetic

<400> SEQUENCE: 270

Ile Asn Trp Asn Gly Asp Ser Thr
```

<210> SEQ ID NO 271
<211> LENGTH: 51
<212> TYPE: DNA
<213> ORGANISM: Artificial Sequence
<220> FEATURE:
<223> OTHER INFORMATION: synthetic

<400> SEQUENCE: 271
gcgagagcgg ggattgtagt agactggaat tacgcgggct ggttcgaccc c        51

<210> SEQ ID NO 272
<211> LENGTH: 17
<212> TYPE: PRT
<213> ORGANISM: Artificial Sequence
<220> FEATURE:
<223> OTHER INFORMATION: synthetic

<400> SEQUENCE: 272

Ala Arg Ala Gly Ile Val Val Asp Trp Asn Tyr Ala Gly Trp Phe Asp
1               5                   10                  15

Pro

<210> SEQ ID NO 273
<211> LENGTH: 324
<212> TYPE: DNA
<213> ORGANISM: Artificial Sequence
<220> FEATURE:
<223> OTHER INFORMATION: synthetic

<400> SEQUENCE: 273
gacatccaga tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacca gctggagat caaa                                           324

<210> SEQ ID NO 274
<211> LENGTH: 108
<212> TYPE: PRT
<213> ORGANISM: Artificial Sequence
<220> FEATURE:
<223> OTHER INFORMATION: synthetic

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Leu Glu Ile Lys
            100                 105

<210> SEQ ID NO 275
<211> LENGTH: 18
<212> TYPE: DNA
<213> ORGANISM: Artificial Sequence
<220> FEATURE:
<223> OTHER INFORMATION: synthetic

<400> SEQUENCE: 275
cagagcatta gcagctat                                              18

<210> SEQ ID NO 276
<211> LENGTH: 6
<212> TYPE: PRT
<213> ORGANISM: Artificial Sequence
<220> FEATURE:
<223> OTHER INFORMATION: synthetic

<400> SEQUENCE: 276

Gln Ser Ile Ser Ser Tyr
1               5

<210> SEQ ID NO 277
<211> LENGTH: 9
<212> TYPE: DNA
<213> ORGANISM: Artificial Sequence
<220> FEATURE:
<223> OTHER INFORMATION: synthetic

<400> SEQUENCE: 277 gctgcatcc                                                        9

<210> SEQ ID NO 278
<211> LENGTH: 3
<212> TYPE: PRT
<213> ORGANISM: Artificial Sequence
<220> FEATURE:
<223> OTHER INFORMATION: synthetic

<400> SEQUENCE: 278

Ala Ala Ser
1

<210> SEQ ID NO 279
<211> LENGTH: 30
<212> TYPE: DNA
<213> ORGANISM: Artificial Sequence
<220> FEATURE:
<223> OTHER INFORMATION: synthetic

<400> SEQUENCE: 279
caacagagtt acagtaccccc tccgatcacc                                30

<210> SEQ ID NO 280
<211> LENGTH: 10
<212> TYPE: PRT
<213> ORGANISM: Artificial Sequence
<220> FEATURE:
<223> OTHER INFORMATION: synthetic

<400> SEQUENCE: 280

Gln Gln Ser Tyr Ser Thr Pro Pro Ile Thr
1               5                   10

<210> SEQ ID NO 281
<211> LENGTH: 375
<212> TYPE: DNA
<213> ORGANISM: Artificial Sequence
<220> FEATURE:
<223> OTHER INFORMATION: synthetic

<400> SEQUENCE: 281

```
gaggtgcagc tggtggagtc tgggggaggc ttggtccagc ctgggggtc  cctgagactc    60 tcctgtgcag cctctggatt caccttcact ttctatgcta tgcactgggt ccgccaggct   120
ccagggaagg gactggaata tgtttcaggt attagcagta atgggggaag cacaaaatat   180
gcagactctg tgaagggcag attcaccatt tccagagaca attccaagaa cacgctgtat   240
cttcaaatgg gcagcctgag agctgaggac ttggctgtgt attactgtgc gagatcgtat   300
gccagctcgt cggattacca ctactactac ggtatggacg tctggggcca agggaccacg   360
gtcaccgtct cctca                                                    375
```

<210> SEQ ID NO 282
<211> LENGTH: 125
<212> TYPE: PRT
<213> ORGANISM: Artificial Sequence
<220> FEATURE:
<223> OTHER INFORMATION: synthetic

<400> SEQUENCE: 282

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Phe Tyr
            20                  25                  30

Ala Met His Trp Val Arg Gln Ala Pro Gly Lys Gly Leu Glu Tyr Val
        35                  40                  45

Ser Gly Ile Ser Ser Asn Gly Gly Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Leu Ala Val Tyr Tyr Cys
                85                  90                  95

Ala Arg Ser Tyr Ala Ser Ser Ser Asp Tyr His Tyr Tyr Tyr Gly Met
            100                 105                 110

Asp Val Trp Gly Gln Gly Thr Thr Val Thr Val Ser Ser
        115                 120                 125

<210> SEQ ID NO 283
<211> LENGTH: 24
<212> TYPE: DNA
<213> ORGANISM: Artificial Sequence
<220> FEATURE:
<223> OTHER INFORMATION: synthetic

<400> SEQUENCE: 283

```
ggattcacct tcactttcta tgct                                            24
```

<210> SEQ ID NO 284
<211> LENGTH: 8
<212> TYPE: PRT
<213> ORGANISM: Artificial Sequence
<220> FEATURE:
<223> OTHER INFORMATION: synthetic

<400> SEQUENCE: 284

-continued

Gly Phe Thr Phe Thr Phe Tyr Ala
1               5

<210> SEQ ID NO 285
<211> LENGTH: 24
<212> TYPE: DNA
<213> ORGANISM: Artificial Sequence
<220> FEATURE:
<223> OTHER INFORMATION: synthetic

<400> SEQUENCE: 285
attagcagta atgggggaag caca                                          24

<210> SEQ ID NO 286
<211> LENGTH: 8
<212> TYPE: PRT
<213> ORGANISM: Artificial Sequence
<220> FEATURE:
<223> OTHER INFORMATION: synthetic

<400> SEQUENCE: 286

Ile Ser Ser Asn Gly Gly Ser Thr
1               5

<210> SEQ ID NO 287
<211> LENGTH: 54
<212> TYPE: DNA
<213> ORGANISM: Artificial Sequence
<220> FEATURE:
<223> OTHER INFORMATION: synthetic

<400> SEQUENCE: 287
gcgagatcgt atgccagctc gtcggattac cactactact acggtatgga cgtc         54

<210> SEQ ID NO 288
<211> LENGTH: 18
<212> TYPE: PRT
<213> ORGANISM: Artificial Sequence
<220> FEATURE:
<223> OTHER INFORMATION: synthetic

<400> SEQUENCE: 288

Ala Arg Ser Tyr Ala Ser Ser Ser Asp Tyr His Tyr Tyr Tyr Gly Met
1               5                   10                  15

Asp Val

<210> SEQ ID NO 289
<211> LENGTH: 324
<212> TYPE: DNA
<213> ORGANISM: Artificial Sequence
<220> FEATURE:
<223> OTHER INFORMATION: synthetic

<400> SEQUENCE: 289
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 290

```
<211> LENGTH: 108
<212> TYPE: PRT
<213> ORGANISM: Artificial Sequence
<220> FEATURE:
<223> OTHER INFORMATION: synthetic

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 291
<211> LENGTH: 18
<212> TYPE: DNA
<213> ORGANISM: Artificial Sequence
<220> FEATURE:
<223> OTHER INFORMATION: synthetic

<400> SEQUENCE: 291
cagagcatta gcagctat                                                    18

<210> SEQ ID NO 292
<211> LENGTH: 6
<212> TYPE: PRT
<213> ORGANISM: Artificial Sequence
<220> FEATURE:
<223> OTHER INFORMATION: synthetic

<400> SEQUENCE: 292

Gln Ser Ile Ser Ser Tyr
1               5

<210> SEQ ID NO 293
<211> LENGTH: 9
<212> TYPE: DNA
<213> ORGANISM: Artificial Sequence
<220> FEATURE:
<223> OTHER INFORMATION: synthetic

<400> SEQUENCE: 293 gctgcatcc                                                              9

<210> SEQ ID NO 294
<211> LENGTH: 3
<212> TYPE: PRT
<213> ORGANISM: Artificial Sequence
<220> FEATURE:
<223> OTHER INFORMATION: synthetic

<400> SEQUENCE: 294

Ala Ala Ser
1
```

<210> SEQ ID NO 295
<211> LENGTH: 30
<212> TYPE: DNA
<213> ORGANISM: Artificial Sequence
<220> FEATURE:
<223> OTHER INFORMATION: synthetic

<400> SEQUENCE: 295
caacagagtt acagtacccc tccgatcacc                               30

<210> SEQ ID NO 296
<211> LENGTH: 10
<212> TYPE: PRT
<213> ORGANISM: Artificial Sequence
<220> FEATURE:
<223> OTHER INFORMATION: synthetic

<400> SEQUENCE: 296

Gln Gln Ser Tyr Ser Thr Pro Pro Ile Thr
1               5                   10

<210> SEQ ID NO 297
<211> LENGTH: 357
<212> TYPE: DNA
<213> ORGANISM: Artificial Sequence
<220> FEATURE:
<223> OTHER INFORMATION: synthetic

<400> SEQUENCE: 297
gaagtgcagc tggtggagtc tgggggaggc gtggtacagc ctgggggtc cctgagactc    60 tcctgtgcag cctctggact cacctttgat gattatgtca tgcactgggt ccgccaagct   120
ccagggaagg gtctggagtg ggtctctctt ataagtggga tggaggtaa cacagactat    180 gtagactctg tgaagggccg attcaccatc tccagagaca acagcaaaaa ctccctgtat   240
ctgcaaatga acagtctgag aactgaggac accgccttgt attactgtgc aaaagatatc   300
ggctgggctg atgctttttga tatctggggc caagggacaa tggtcaccgt ctcttca     357

<210> SEQ ID NO 298
<211> LENGTH: 119
<212> TYPE: PRT
<213> ORGANISM: Artificial Sequence
<220> FEATURE:
<223> OTHER INFORMATION: synthetic

<400> SEQUENCE: 298

Glu Val Gln Leu Val Glu Ser Gly Gly Gly Val Val Gln Pro Gly Gly
1               5                   10                  15

Ser Leu Arg Leu Ser Cys Ala Ala Ser Gly Leu Thr Phe Asp Asp Tyr
            20                  25                  30

Val Met His Trp Val Arg Gln Ala Pro Gly Lys Gly Leu Glu Trp Val
        35                  40                  45

Ser Leu Ile Ser Gly Asn Gly Gly Asn Thr Asp Tyr Val Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Ile Gly Trp Ala Asp Ala Phe Asp Ile Trp Gly Gln Gly
            100                 105                 110

Thr Met Val Thr Val Ser Ser
        115

```
                      115

<210> SEQ ID NO 299
<211> LENGTH: 24
<212> TYPE: DNA
<213> ORGANISM: Artificial Sequence
<220> FEATURE:
<223> OTHER INFORMATION: synthetic

<400> SEQUENCE: 299
ggactcacct ttgatgatta tgtc                                            24

<210> SEQ ID NO 300
<211> LENGTH: 8
<212> TYPE: PRT
<213> ORGANISM: Artificial Sequence
<220> FEATURE:
<223> OTHER INFORMATION: synthetic

<400> SEQUENCE: 300

Gly Leu Thr Phe Asp Asp Tyr Val
1               5

<210> SEQ ID NO 301
<211> LENGTH: 24
<212> TYPE: DNA
<213> ORGANISM: Artificial Sequence
<220> FEATURE:
<223> OTHER INFORMATION: synthetic

<400> SEQUENCE: 301
ataagtggga atggaggtaa caca                                            24

<210> SEQ ID NO 302
<211> LENGTH: 8
<212> TYPE: PRT
<213> ORGANISM: Artificial Sequence
<220> FEATURE:
<223> OTHER INFORMATION: synthetic

<400> SEQUENCE: 302

Ile Ser Gly Asn Gly Gly Asn Thr
1               5

<210> SEQ ID NO 303
<211> LENGTH: 36
<212> TYPE: DNA
<213> ORGANISM: Artificial Sequence
<220> FEATURE:
<223> OTHER INFORMATION: synthetic

<400> SEQUENCE: 303
gcaaaagata tcggctgggc tgatgctttt gatatc                               36

<210> SEQ ID NO 304
<211> LENGTH: 12
<212> TYPE: PRT
<213> ORGANISM: Artificial Sequence
<220> FEATURE:
<223> OTHER INFORMATION: synthetic

<400> SEQUENCE: 304

Ala Lys Asp Ile Gly Trp Ala Asp Ala Phe Asp Ile
1               5                   10

<210> SEQ ID NO 305
```

<211> LENGTH: 321
<212> TYPE: DNA
<213> ORGANISM: Artificial Sequence
<220> FEATURE:
<223> OTHER INFORMATION: synthetic

<400> SEQUENCE: 305

```
gacatccaga tgacccagtc tccatcctcc ctgtctgcat ctgtaggaga cagagtcacc      60
atcacttgcc gggcaagtca gagcgttagc ccctatttaa attggtatca gcagaaccca     120
gggaaagccc ctaagttcct gatctttgct gcatccaatt tgcaaagtgg ggtcccatca     180
aggttcagtg gcagtggatc tgggacagat ttcactctca ccatcagctc tctgcaacct     240
gaagattttg caacttacta ctgtcaacag agttacacca ccccgtacac ttttggccag     300
gggaccaagc tggagatcaa a                                               321
```

<210> SEQ ID NO 306
<211> LENGTH: 107
<212> TYPE: PRT
<213> ORGANISM: Artificial Sequence
<220> FEATURE:
<223> OTHER INFORMATION: synthetic

<400> SEQUENCE: 306

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Val Ser Pro Tyr
            20                  25                  30
Leu Asn Trp Tyr Gln Gln Asn Pro Gly Lys Ala Pro Lys Phe Leu Ile
        35                  40                  45
Phe Ala Ala Ser Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Thr Thr Pro Tyr
                85                  90                  95
Thr Phe Gly Gln Gly Thr Lys Leu Glu Ile Lys
            100                 105
```

<210> SEQ ID NO 307
<211> LENGTH: 18
<212> TYPE: DNA
<213> ORGANISM: Artificial Sequence
<220> FEATURE:
<223> OTHER INFORMATION: synthetic

<400> SEQUENCE: 307

```
cagagcgtta gcccctat                                                    18
```

<210> SEQ ID NO 308
<211> LENGTH: 6
<212> TYPE: PRT
<213> ORGANISM: Artificial Sequence
<220> FEATURE:
<223> OTHER INFORMATION: synthetic

<400> SEQUENCE: 308

```
Gln Ser Val Ser Pro Tyr
1               5
```

<210> SEQ ID NO 309
<211> LENGTH: 9

<210> SEQ ID NO 310
<211> LENGTH: 3
<212> TYPE: PRT
<213> ORGANISM: Artificial Sequence
<220> FEATURE:
<223> OTHER INFORMATION: synthetic

<400> SEQUENCE: 309 gctgcatcc                                                                 9

<210> SEQ ID NO 310
<211> LENGTH: 3
<212> TYPE: PRT
<213> ORGANISM: Artificial Sequence
<220> FEATURE:
<223> OTHER INFORMATION: synthetic

<400> SEQUENCE: 310

Ala Ala Ser
1

<210> SEQ ID NO 311
<211> LENGTH: 27
<212> TYPE: DNA
<213> ORGANISM: Artificial Sequence
<220> FEATURE:
<223> OTHER INFORMATION: synthetic

<400> SEQUENCE: 311
caacagagtt acaccacccc gtacact                                            27

<210> SEQ ID NO 312
<211> LENGTH: 9
<212> TYPE: PRT
<213> ORGANISM: Artificial Sequence
<220> FEATURE:
<223> OTHER INFORMATION: synthetic

<400> SEQUENCE: 312

Gln Gln Ser Tyr Thr Thr Pro Tyr Thr
1               5

<210> SEQ ID NO 313
<211> LENGTH: 360
<212> TYPE: DNA
<213> ORGANISM: Artificial Sequence
<220> FEATURE:
<223> OTHER INFORMATION: synthetic

<400> SEQUENCE: 313
gaggtgcagc tggtggagtc tgggggaggc gtggtacagc ctggggggtc cctgagactc        60
tcctgtgcag cctctggatt cacctttagt aactatggca tgcactgggt ccgccaggct       120
ccagggaagg ggctggagtg ggtctcagtt attagtggta tggtggtaa cacaaactat        180 gtagactccg tggagggccg attcaccatc tccagagaca attccaagaa ctccctgtat       240
ctgcaaatga acagcctgag agccgaggac acggccgtgt attactgtgc gaaaggtatt      300
agtggctggg ctgatgcttt tgatatctgg ggccaaggga caatggtcac cgtctcttca     360

<210> SEQ ID NO 314
<211> LENGTH: 120
<212> TYPE: PRT
<213> ORGANISM: Artificial Sequence
<220> FEATURE:
<223> OTHER INFORMATION: synthetic

<400> SEQUENCE: 314

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Val Ile Ser Gly Asn Gly Gly Asn Thr Asn Tyr Val Asp Ser Val
    50                  55                  60

Glu Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Ser Gly Trp Ala Asp Ala Phe Asp Ile Trp Gly Gln
            100                 105                 110

Gly Thr Met Val Thr Val Ser Ser
        115                 120

<210> SEQ ID NO 315
<211> LENGTH: 24
<212> TYPE: DNA
<213> ORGANISM: Artificial Sequence
<220> FEATURE:
<223> OTHER INFORMATION: synthetic

<400> SEQUENCE: 315
ggattcacct ttagtaacta tggc                                      24

<210> SEQ ID NO 316
<211> LENGTH: 8
<212> TYPE: PRT
<213> ORGANISM: Artificial Sequence
<220> FEATURE:
<223> OTHER INFORMATION: synthetic

<400> SEQUENCE: 316

Gly Phe Thr Phe Ser Asn Tyr Gly
1               5

<210> SEQ ID NO 317
<211> LENGTH: 24
<212> TYPE: DNA
<213> ORGANISM: Artificial Sequence
<220> FEATURE:
<223> OTHER INFORMATION: synthetic

<400> SEQUENCE: 317
attagtggta atggtggtaa caca                                      24

<210> SEQ ID NO 318
<211> LENGTH: 8
<212> TYPE: PRT
<213> ORGANISM: Artificial Sequence
<220> FEATURE:
<223> OTHER INFORMATION: synthetic

<400> SEQUENCE: 318

Ile Ser Gly Asn Gly Gly Asn Thr
1               5

<210> SEQ ID NO 319
<211> LENGTH: 39
<212> TYPE: DNA
<213> ORGANISM: Artificial Sequence
```

<220> FEATURE:
<223> OTHER INFORMATION: synthetic

<400> SEQUENCE: 319
gcgaaaggta ttagtggctg ggctgatgct tttgatatc                      39

<210> SEQ ID NO 320
<211> LENGTH: 13
<212> TYPE: PRT
<213> ORGANISM: Artificial Sequence
<220> FEATURE:
<223> OTHER INFORMATION: synthetic

<400> SEQUENCE: 320

Ala Lys Gly Ile Ser Gly Trp Ala Asp Ala Phe Asp Ile
1               5                   10

<210> SEQ ID NO 321
<211> LENGTH: 321
<212> TYPE: DNA
<213> ORGANISM: Artificial Sequence
<220> FEATURE:
<223> OTHER INFORMATION: synthetic

<400> SEQUENCE: 321
gacatccaga tgacccagtc tccatcctcc ctgtctgcat ctgtaggaga cagagtcacc      60
atcacttgcc gggcaagtca gagcgttagc ccctatttaa attggtatca gcagaaacca     120
gggaaagccc ctaaattcct gatctttgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgtacac ttttggccag     300
gggaccaagc tggagatcaa a                                              321

<210> SEQ ID NO 322
<211> LENGTH: 107
<212> TYPE: PRT
<213> ORGANISM: Artificial Sequence
<220> FEATURE:
<223> OTHER INFORMATION: synthetic

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Asn Trp Tyr Gln Gln Lys Pro Gly Lys Ala Pro Lys Phe Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 323
<211> LENGTH: 18
<212> TYPE: DNA
<213> ORGANISM: Artificial Sequence
<220> FEATURE:

<223> OTHER INFORMATION: synthetic

<400> SEQUENCE: 323
cagagcgtta gcccctat                                                        18

<210> SEQ ID NO 324
<211> LENGTH: 6
<212> TYPE: PRT
<213> ORGANISM: Artificial Sequence
<220> FEATURE:
<223> OTHER INFORMATION: synthetic

<400> SEQUENCE: 324

Gln Ser Val Ser Pro Tyr
1               5

<210> SEQ ID NO 325
<211> LENGTH: 9
<212> TYPE: DNA
<213> ORGANISM: Artificial Sequence
<220> FEATURE:
<223> OTHER INFORMATION: synthetic

<400> SEQUENCE: 325 gctgcatcc                                                                   9

<210> SEQ ID NO 326
<211> LENGTH: 3
<212> TYPE: PRT
<213> ORGANISM: Artificial Sequence
<220> FEATURE:
<223> OTHER INFORMATION: synthetic

<400> SEQUENCE: 326

Ala Ala Ser
1

<210> SEQ ID NO 327
<211> LENGTH: 27
<212> TYPE: DNA
<213> ORGANISM: Artificial Sequence
<220> FEATURE:
<223> OTHER INFORMATION: synthetic

<400> SEQUENCE: 327
caacagagtt acagtacccc gtacact                                              27

<210> SEQ ID NO 328
<211> LENGTH: 9
<212> TYPE: PRT
<213> ORGANISM: Artificial Sequence
<220> FEATURE:
<223> OTHER INFORMATION: synthetic

<400> SEQUENCE: 328

Gln Gln Ser Tyr Ser Thr Pro Tyr Thr
1               5

<210> SEQ ID NO 329
<211> LENGTH: 363
<212> TYPE: DNA
<213> ORGANISM: Artificial Sequence
<220> FEATURE:
<223> OTHER INFORMATION: synthetic

<400> SEQUENCE: 329

```
gaggtgcagc tggtggagtc tgggggaggc ttggtaaagc ctggggggtc ccttagactc      60
tcctgtgcag cctctggatt cactttcagt aacgcctgga tgagctgggt ccgccaggct     120
ccagggaagg ggctggaatg ggttggccgt attaaaacca gagctgatgg tgggacaaca     180
gactacgctg cacccgtgaa aggcagattc accatctcaa gagatgattc aaaaaacacg     240
ctgtatctgc aactgaacag cctgaaaacc gaggacacag ccgtgtatta ctgtacctct     300
cataactgga actacgaaga ctttgactac tggggccagg aaccctggt cactgtctcc     360 tca                                                                  363
```

```
<210> SEQ ID NO 330
<211> LENGTH: 121
<212> TYPE: PRT
<213> ORGANISM: Artificial Sequence
<220> FEATURE:
<223> OTHER INFORMATION: synthetic

<400> SEQUENCE: 330
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Thr Arg Ala Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Leu Asn Ser Leu Lys Thr Glu Asp Thr Ala Val Tyr
                85                  90                  95

Tyr Cys Thr Ser His Asn Trp Asn Tyr Glu Asp Phe Asp Tyr Trp Gly
            100                 105                 110

Gln Gly Thr Leu Val Thr Val Ser Ser
        115                 120

```
<210> SEQ ID NO 331
<211> LENGTH: 24
<212> TYPE: DNA
<213> ORGANISM: Artificial Sequence
<220> FEATURE:
<223> OTHER INFORMATION: synthetic

<400> SEQUENCE: 331
ggattcactt tcagtaacgc ctgg                                            24

<210> SEQ ID NO 332
<211> LENGTH: 8
<212> TYPE: PRT
<213> ORGANISM: Artificial Sequence
<220> FEATURE:
<223> OTHER INFORMATION: synthetic

<400> SEQUENCE: 332
```

Gly Phe Thr Phe Ser Asn Ala Trp
1               5

```
<210> SEQ ID NO 333
<211> LENGTH: 30
<212> TYPE: DNA
<213> ORGANISM: Artificial Sequence
<220> FEATURE:
```

<223> OTHER INFORMATION: synthetic

<400> SEQUENCE: 333
attaaaacca gagctgatgg tgggacaaca                                              30

<210> SEQ ID NO 334
<211> LENGTH: 10
<212> TYPE: PRT
<213> ORGANISM: Artificial Sequence
<220> FEATURE:
<223> OTHER INFORMATION: synthetic

<400> SEQUENCE: 334

Ile Lys Thr Arg Ala Asp Gly Gly Thr Thr
1               5                  10

<210> SEQ ID NO 335
<211> LENGTH: 36
<212> TYPE: DNA
<213> ORGANISM: Artificial Sequence
<220> FEATURE:
<223> OTHER INFORMATION: synthetic

<400> SEQUENCE: 335
acctctcata actggaacta cgaagacttt gactac                                      36

<210> SEQ ID NO 336
<211> LENGTH: 12
<212> TYPE: PRT
<213> ORGANISM: Artificial Sequence
<220> FEATURE:
<223> OTHER INFORMATION: synthetic

<400> SEQUENCE: 336

Thr Ser His Asn Trp Asn Tyr Glu Asp Phe Asp Tyr
1               5                  10

<210> SEQ ID NO 337
<211> LENGTH: 321
<212> TYPE: DNA
<213> ORGANISM: Artificial Sequence
<220> FEATURE:
<223> OTHER INFORMATION: synthetic

<400> SEQUENCE: 337
gacatccaga tgacccagtc tccatcctcc ctgtctgcat ctgtaggaga cagagtcacc            60
atcacttgcc gggcaagtca gagcattagc aactatttaa attggtatca gcagaaacca           120
gggaaagccc ctaaactcct gatctatgct gcatccagtt tgcaaagtgg ggtcccatca           180
aggttcagtg gcagtggatc tgggacagac ttcactctca ccatcagcag tctgcaacct           240
gaagagtttg caacttacta ctgtcaacag agttacagta tcccgtacac ttttggccag           300
gggaccaagc tggagatcaa a                                                     321

<210> SEQ ID NO 338
<211> LENGTH: 107
<212> TYPE: PRT
<213> ORGANISM: Artificial Sequence
<220> FEATURE:
<223> OTHER INFORMATION: synthetic

<400> SEQUENCE: 338

Asp Ile Gln Met Thr Gln Ser Pro Ser Ser Leu Ser Ala Ser Val Gly
1               5                  10                  15

-continued

```
Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Glu Phe Ala Thr Tyr Tyr Cys Gln Gln Ser Tyr Ser Ile Pro Tyr
                85                  90                  95

Thr Phe Gly Gln Gly Thr Lys Leu Glu Ile Lys
            100                 105
```

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
gcaagtcaga gcattagcaa ctat                                          24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

Ala Ser Gln Ser Ile Ser Asn Tyr
1               5

<210> SEQ ID NO 341
<211> LENGTH: 30
<212> TYPE: DNA
<213> ORGANISM: Artificial Sequence
<220> FEATURE:
<223> OTHER INFORMATION: synthetic

<400> SEQUENCE: 341
gctgcatcca gtttgcaaag tggggtccca                                    30

<210> SEQ ID NO 342
<211> LENGTH: 10
<212> TYPE: PRT
<213> ORGANISM: Artificial Sequence
<220> FEATURE:
<223> OTHER INFORMATION: synthetic

<400> SEQUENCE: 342

Ala Ala Ser Ser Leu Gln Ser Gly Val Pro
1               5                   10

<210> SEQ ID NO 343
<211> LENGTH: 12
<212> TYPE: DNA
<213> ORGANISM: Artificial Sequence
<220> FEATURE:
<223> OTHER INFORMATION: synthetic

<400> SEQUENCE: 343
atcccgtaca ct                                                       12

<210> SEQ ID NO 344
<211> LENGTH: 4
<212> TYPE: PRT
<213> ORGANISM: Artificial Sequence
<220> FEATURE:
<223> OTHER INFORMATION: synthetic

<400> SEQUENCE: 344

Ile Pro Tyr Thr
1

<210> SEQ ID NO 345
<211> LENGTH: 369
<212> TYPE: DNA
<213> ORGANISM: Artificial Sequence
<220> FEATURE:
<223> OTHER INFORMATION: synthetic

<400> SEQUENCE: 345

```
gaggtgcagc tggtggagtc tgggggaggc ttggtacagc ctgggggtc cctgagactc     60 tcctgtgcag cctctggatt cacctttagc agctatgcca tgagctgggt ccgccaggct    120
ccagggaagg ggctggagtg ggtctcaggt attagtggta gtggtggtac aacatacgac    180
gcagactccg tgaagggccg gttcaccatc tccagagaca attccaagaa cacgctgtat    240
ctgcaaatgc acagtctgag agccgaggac acggccgcat attactgtgc gaaagactgg    300
aactacgggc cctattacta cttcggtatg gacgtctggg gccaagggac cacggtcacc    360
gtctcctca                                                            369
```

<210> SEQ ID NO 346
<211> LENGTH: 123
<212> TYPE: PRT
<213> ORGANISM: Artificial Sequence
<220> FEATURE:
<223> OTHER INFORMATION: synthetic

<400> SEQUENCE: 346

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Thr Thr Tyr Asp Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Ala Tyr Tyr Cys
                85                  90                  95

Ala Lys Asp Trp Asn Tyr Gly Pro Tyr Tyr Phe Gly Met Asp Val
            100                 105                 110

Trp Gly Gln Gly Thr Thr Val Thr Val Ser Ser
        115                 120

<210> SEQ ID NO 347
<211> LENGTH: 24
<212> TYPE: DNA
<213> ORGANISM: Artificial Sequence
<220> FEATURE:
<223> OTHER INFORMATION: synthetic

<400> SEQUENCE: 347 ggattcaccct ttagcagcta tgcc                                              24

<210> SEQ ID NO 348
<211> LENGTH: 8
<212> TYPE: PRT
<213> ORGANISM: Artificial Sequence
<220> FEATURE:
<223> OTHER INFORMATION: synthetic

<400> SEQUENCE: 348

Gly Phe Thr Phe Ser Ser Tyr Ala
1               5

<210> SEQ ID NO 349
<211> LENGTH: 24
<212> TYPE: DNA
<213> ORGANISM: Artificial Sequence
<220> FEATURE:
<223> OTHER INFORMATION: synthetic

<400> SEQUENCE: 349
attagtggta gtggtggtac aaca                                               24

<210> SEQ ID NO 350
<211> LENGTH: 8
<212> TYPE: PRT
<213> ORGANISM: Artificial Sequence
<220> FEATURE:
<223> OTHER INFORMATION: synthetic

<400> SEQUENCE: 350

Ile Ser Gly Ser Gly Gly Thr Thr
1               5

<210> SEQ ID NO 351
<211> LENGTH: 48
<212> TYPE: DNA
<213> ORGANISM: Artificial Sequence
<220> FEATURE:
<223> OTHER INFORMATION: synthetic

<400> SEQUENCE: 351
gcgaaagact ggaactacgg gccctattac tacttcggta tggacgtc                     48

<210> SEQ ID NO 352
<211> LENGTH: 16
<212> TYPE: PRT
<213> ORGANISM: Artificial Sequence
<220> FEATURE:
<223> OTHER INFORMATION: synthetic

<400> SEQUENCE: 352

Ala Lys Asp Trp Asn Tyr Gly Pro Tyr Tyr Tyr Phe Gly Met Asp Val
1               5                   10                  15

<210> SEQ ID NO 353
<211> LENGTH: 336
<212> TYPE: DNA
<213> ORGANISM: Artificial Sequence
<220> FEATURE:
<223> OTHER INFORMATION: synthetic

<400> SEQUENCE: 353
gatattgtga tgactcagtc tccactctcc ctgcccgtca cccctggaga gccggcctcc        60

```
atctcctgca ggtctagtca gagcctcctg catagtaatg aatacaacta tttggattgg    120
tacctgcaga agccagggca gtctccacag ctcctgatct atttgggttc taatcgggcc    180
tccggggtcc ctgacaggtt cagtggcagt ggatcaggca cagattttac attgaaaatc    240
agcagagtgg aggctgagga tgttggggtt tattactgca tgcaagctct acaaactcct    300
ccgacgttcg gccaagggac caaggtggaa atcaaa                              336
```

<210> SEQ ID NO 354
<211> LENGTH: 112
<212> TYPE: PRT
<213> ORGANISM: Artificial Sequence
<220> FEATURE:
<223> OTHER INFORMATION: synthetic

<400> SEQUENCE: 354

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gln Gly Thr Lys Val Glu Ile Lys
            100                 105                 110

<210> SEQ ID NO 355
<211> LENGTH: 33
<212> TYPE: DNA
<213> ORGANISM: Artificial Sequence
<220> FEATURE:
<223> OTHER INFORMATION: synthetic

<400> SEQUENCE: 355

```
cagagcctcc tgcatagtaa tgaatacaac tat                                 33
```

<210> SEQ ID NO 356
<211> LENGTH: 11
<212> TYPE: PRT
<213> ORGANISM: Artificial Sequence
<220> FEATURE:
<223> OTHER INFORMATION: synthetic

<400> SEQUENCE: 356

Gln Ser Leu Leu His Ser Asn Glu Tyr Asn Tyr
1               5                   10

<210> SEQ ID NO 357
<211> LENGTH: 9
<212> TYPE: DNA
<213> ORGANISM: Artificial Sequence
<220> FEATURE:
<223> OTHER INFORMATION: synthetic

<400> SEQUENCE: 357

```
ttgggttct                                                             9
```

<210> SEQ ID NO 358
<211> LENGTH: 3
<212> TYPE: PRT
<213> ORGANISM: Artificial Sequence
<220> FEATURE:
<223> OTHER INFORMATION: synthetic

<400> SEQUENCE: 358

Leu Gly Ser
1

<210> SEQ ID NO 359
<211> LENGTH: 27
<212> TYPE: DNA
<213> ORGANISM: Artificial Sequence
<220> FEATURE:
<223> OTHER INFORMATION: synthetic

<400> SEQUENCE: 359
atgcaagctc tacaaactcc tccgacg                                        27

<210> SEQ ID NO 360
<211> LENGTH: 9
<212> TYPE: PRT
<213> ORGANISM: Artificial Sequence
<220> FEATURE:
<223> OTHER INFORMATION: synthetic

<400> SEQUENCE: 360

Met Gln Ala Leu Gln Thr Pro Pro Thr
1               5

<210> SEQ ID NO 361
<211> LENGTH: 366
<212> TYPE: DNA
<213> ORGANISM: Artificial Sequence
<220> FEATURE:
<223> OTHER INFORMATION: synthetic

<400> SEQUENCE: 361
gaggtgcagc tggtggagtc tgggggaggc ttggtacagc ctggggggtc cctgagactc     60
tcctgtgcag cctctggatt cacctttagc agctatgcca tgagctgggt ccgccaggct    120
ccagggcagg ggctggaatg ggtctcagct attagtggta gcggtgatgg cacatactac    180
gcagactccg tgaagggccg gttcaccatc tccagagaca tttccaagaa cacgctgtat    240
ctgcaaatga acagcctgaa aaccgaggac acggccgtat attactgtgc gagagatgcc    300
tataactgga actactactg gtatttcgat ctctggggcc gtggcaccct ggtcaccgtc    360
tcctca                                                              366

<210> SEQ ID NO 362
<211> LENGTH: 122
<212> TYPE: PRT
<213> ORGANISM: Artificial Sequence
<220> FEATURE:
<223> OTHER INFORMATION: synthetic

<400> SEQUENCE: 362

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Gln Gly Leu Glu Trp Val

```
                  35                  40                  45
Ser Ala Ile Ser Gly Ser Gly Asp Gly Thr Tyr Tyr Ala Asp Ser Val
        50                  55                  60

Lys Gly Arg Phe Thr Ile Ser Arg Asp Ile Ser Lys Asn Thr Leu Tyr
 65                  70                  75                  80

Leu Gln Met Asn Ser Leu Lys Thr Glu Asp Thr Ala Val Tyr Tyr Cys
                85                  90                  95

Ala Arg Asp Ala Tyr Asn Trp Asn Tyr Tyr Trp Tyr Phe Asp Leu Trp
            100                 105                 110

Gly Arg Gly Thr Leu Val Thr Val Ser Ser
        115                 120
```

<210> SEQ ID NO 363
<211> LENGTH: 24
<212> TYPE: DNA
<213> ORGANISM: Artificial Sequence
<220> FEATURE:
<223> OTHER INFORMATION: synthetic

<400> SEQUENCE: 363
ggattcacct ttagcagcta tgcc                                    24

<210> SEQ ID NO 364
<211> LENGTH: 8
<212> TYPE: PRT
<213> ORGANISM: Artificial Sequence
<220> FEATURE:
<223> OTHER INFORMATION: synthetic

<400> SEQUENCE: 364

```
Gly Phe Thr Phe Ser Ser Tyr Ala
 1               5
```

<210> SEQ ID NO 365
<211> LENGTH: 24
<212> TYPE: DNA
<213> ORGANISM: Artificial Sequence
<220> FEATURE:
<223> OTHER INFORMATION: synthetic

<400> SEQUENCE: 365
attagtggta gcggtgatgg caca                                    24

<210> SEQ ID NO 366
<211> LENGTH: 8
<212> TYPE: PRT
<213> ORGANISM: Artificial Sequence
<220> FEATURE:
<223> OTHER INFORMATION: synthetic

<400> SEQUENCE: 366

```
Ile Ser Gly Ser Gly Asp Gly Thr
 1               5
```

<210> SEQ ID NO 367
<211> LENGTH: 45
<212> TYPE: DNA
<213> ORGANISM: Artificial Sequence
<220> FEATURE:
<223> OTHER INFORMATION: synthetic

<400> SEQUENCE: 367
gcgagagatg cctataactg gaactactac tggtatttcg atctc              45

<210> SEQ ID NO 368
<211> LENGTH: 15
<212> TYPE: PRT
<213> ORGANISM: Artificial Sequence
<220> FEATURE:
<223> OTHER INFORMATION: synthetic

<400> SEQUENCE: 368

Ala Arg Asp Ala Tyr Asn Trp Asn Tyr Tyr Trp Tyr Phe Asp Leu
1               5                   10                  15

<210> SEQ ID NO 369
<211> LENGTH: 321
<212> TYPE: DNA
<213> ORGANISM: Artificial Sequence
<220> FEATURE:
<223> OTHER INFORMATION: synthetic

<400> SEQUENCE: 369
gaaatagtga tgacgcagtc tccagccacc ctgtctgtgt ctccaggaga cagagccacc    60
ctctcctgta gggccagtca gactgttagt agcagcttag tttggtacca gcagaaacct   120
ggccaggctc ccaggctcct catctatggt gcatccacca gggccactgg tatcccagcc   180
aggttcagtg gcagtgggtc tgggactgag ttcactctca ccatcagcag cctgcagtct   240
gaagattttg cagtttatta ctgtcagcag tttaataatt ggccgatcac cttcggccaa   300
gggacacgac tggagattaa a                                             321

<210> SEQ ID NO 370
<211> LENGTH: 107
<212> TYPE: PRT
<213> ORGANISM: Artificial Sequence
<220> FEATURE:
<223> OTHER INFORMATION: synthetic

<400> SEQUENCE: 370

Glu Ile Val Met Thr Gln Ser Pro Ala Thr Leu Ser Val Ser Pro Gly
1               5                   10                  15

Asp Arg Ala Thr Leu Ser Cys Arg Ala Ser Gln Thr Val Ser Ser Ser
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asn Trp Pro Ile
                85                  90                  95

Thr Phe Gly Gln Gly Thr Arg Leu Glu Ile Lys
            100                 105

<210> SEQ ID NO 371
<211> LENGTH: 18
<212> TYPE: DNA
<213> ORGANISM: Artificial Sequence
<220> FEATURE:
<223> OTHER INFORMATION: synthetic

<400> SEQUENCE: 371
cagactgtta gtagcagc                                                  18

```
<210> SEQ ID NO 372
<211> LENGTH: 6
<212> TYPE: PRT
<213> ORGANISM: Artificial Sequence
<220> FEATURE:
<223> OTHER INFORMATION: synthetic

<400> SEQUENCE: 372

Gln Thr Val Ser Ser Ser
1               5

<210> SEQ ID NO 373
<211> LENGTH: 9
<212> TYPE: DNA
<213> ORGANISM: Artificial Sequence
<220> FEATURE:
<223> OTHER INFORMATION: synthetic

<400> SEQUENCE: 373 ggtgcatcc                                                                 9

<210> SEQ ID NO 374
<211> LENGTH: 3
<212> TYPE: PRT
<213> ORGANISM: Artificial Sequence
<220> FEATURE:
<223> OTHER INFORMATION: synthetic

<400> SEQUENCE: 374

Gly Ala Ser
1

<210> SEQ ID NO 375
<211> LENGTH: 27
<212> TYPE: DNA
<213> ORGANISM: Artificial Sequence
<220> FEATURE:
<223> OTHER INFORMATION: synthetic

<400> SEQUENCE: 375
cagcagttta ataattggcc gatcacc                                            27

<210> SEQ ID NO 376
<211> LENGTH: 9
<212> TYPE: PRT
<213> ORGANISM: Artificial Sequence
<220> FEATURE:
<223> OTHER INFORMATION: synthetic

<400> SEQUENCE: 376

Gln Gln Phe Asn Asn Trp Pro Ile Thr
1               5

<210> SEQ ID NO 377
<211> LENGTH: 378
<212> TYPE: DNA
<213> ORGANISM: Artificial Sequence
<220> FEATURE:
<223> OTHER INFORMATION: synthetic

<400> SEQUENCE: 377
caggtgcagc tggtggagtc tgggggaggc gtggtccagc cagggaggtc cctgagactc        60
tcctgtgcaa cgtctggatt cacctttagt aactatggca tgcactgggt ccgccaggct       120
caaggcaagg gactggagtg ggtggcagtt atatggtttg atggaagtga taaatactat       180
gcagactccg tgaagggccg attcaccatc tccagagaca attccaagaa cacgctgtat       240
```

```
ctgcaaatga acagcctgag agccgaggac acggctgtgt attactgtgc gagagaggct    300
attgtggagg tgattactac ccagggctac tacggtatgg acgtctgggg ccaagggacc    360
acggtcaccg tctcctca                                                  378
```

<210> SEQ ID NO 378
<211> LENGTH: 126
<212> TYPE: PRT
<213> ORGANISM: Artificial Sequence
<220> FEATURE:
<223> OTHER INFORMATION: synthetic

<400> SEQUENCE: 378

```
Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Asn Tyr
            20                  25                  30

Gly Met His Trp Val Arg Gln Ala Gln Gly Lys Gly Leu Glu Trp Val
        35                  40                  45

Ala Val Ile Trp Phe Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Ile Val Glu Val Ile Thr Thr Gln Gly Tyr Tyr Gly
            100                 105                 110

Met Asp Val Trp Gly Gln Gly Thr Thr Val Thr Val Ser Ser
        115                 120                 125
```

<210> SEQ ID NO 379
<211> LENGTH: 24
<212> TYPE: DNA
<213> ORGANISM: Artificial Sequence
<220> FEATURE:
<223> OTHER INFORMATION: synthetic

<400> SEQUENCE: 379

```
ggattcacct ttagtaacta tggc                                            24
```

<210> SEQ ID NO 380
<211> LENGTH: 8
<212> TYPE: PRT
<213> ORGANISM: Artificial Sequence
<220> FEATURE:
<223> OTHER INFORMATION: synthetic

<400> SEQUENCE: 380

```
Gly Phe Thr Phe Ser Asn Tyr Gly
1               5
```

<210> SEQ ID NO 381
<211> LENGTH: 24
<212> TYPE: DNA
<213> ORGANISM: Artificial Sequence
<220> FEATURE:
<223> OTHER INFORMATION: synthetic

<400> SEQUENCE: 381

```
atatggtttg atggaagtga taaa                                            24
```

<210> SEQ ID NO 382
<211> LENGTH: 8
<212> TYPE: PRT
<213> ORGANISM: Artificial Sequence
<220> FEATURE:
<223> OTHER INFORMATION: synthetic

<400> SEQUENCE: 382

Ile Trp Phe Asp Gly Ser Asp Lys
1               5

<210> SEQ ID NO 383
<211> LENGTH: 57
<212> TYPE: DNA
<213> ORGANISM: Artificial Sequence
<220> FEATURE:
<223> OTHER INFORMATION: synthetic

<400> SEQUENCE: 383
gcgagagagg ctattgtgga ggtgattact acccagggct actacggtat ggacgtc        57

<210> SEQ ID NO 384
<211> LENGTH: 19
<212> TYPE: PRT
<213> ORGANISM: Artificial Sequence
<220> FEATURE:
<223> OTHER INFORMATION: synthetic

<400> SEQUENCE: 384

Ala Arg Glu Ala Ile Val Glu Val Ile Thr Thr Gln Gly Tyr Tyr Gly
1               5                   10                  15

Met Asp Val

<210> SEQ ID NO 385
<211> LENGTH: 339
<212> TYPE: DNA
<213> ORGANISM: Artificial Sequence
<220> FEATURE:
<223> OTHER INFORMATION: synthetic

<400> SEQUENCE: 385
gacatcgtga tgacccagtc tccagactcc ctggctgtgt ctctgggcga gagggccacc       60
atcaactgca gtccagcca gactatttta tacagctcca acaataagaa ctacttagct      120
tggtaccagc agaaaccagg acagcctcct aagctgctca tttactggtc atcttcccgg      180
gaatccgggg tccctgaccg attcagtggc agcgggtctg ggacagattt cactctcacc      240
atcagcagcc tgcaggctga agatgtggca gtttattact gtcaacaata ttatactact      300
ccgatcacct tcggccaggg gacacgactg gagattaaa                             339

<210> SEQ ID NO 386
<211> LENGTH: 113
<212> TYPE: PRT
<213> ORGANISM: Artificial Sequence
<220> FEATURE:
<223> OTHER INFORMATION: synthetic

<400> SEQUENCE: 386

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Ile Leu Tyr Ser
                20                  25                  30

Ser Asn Asn Lys Asn Tyr Leu Ala Trp Tyr Gln Gln Lys Pro Gly Gln
            35                  40                  45

```
Pro Pro Lys Leu Leu Ile Tyr Trp Ser Ser Arg Glu Ser Gly Val
    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Ile Thr Phe Gly Gln Gly Thr Arg Leu Glu Ile
            100                 105                 110

Lys

<210> SEQ ID NO 387
<211> LENGTH: 36
<212> TYPE: DNA
<213> ORGANISM: Artificial Sequence
<220> FEATURE:
<223> OTHER INFORMATION: synthetic

<400> SEQUENCE: 387
cagactattt tatacagctc caacaataag aactac                              36

<210> SEQ ID NO 388
<211> LENGTH: 12
<212> TYPE: PRT
<213> ORGANISM: Artificial Sequence
<220> FEATURE:
<223> OTHER INFORMATION: synthetic

<400> SEQUENCE: 388

Gln Thr Ile Leu Tyr Ser Ser Asn Asn Lys Asn Tyr
 1               5                  10

<210> SEQ ID NO 389
<211> LENGTH: 9
<212> TYPE: DNA
<213> ORGANISM: Artificial Sequence
<220> FEATURE:
<223> OTHER INFORMATION: synthetic

<400> SEQUENCE: 389 tggtcatct                                                             9

<210> SEQ ID NO 390
<211> LENGTH: 3
<212> TYPE: PRT
<213> ORGANISM: Artificial Sequence
<220> FEATURE:
<223> OTHER INFORMATION: synthetic

<400> SEQUENCE: 390

Trp Ser Ser
 1

<210> SEQ ID NO 391
<211> LENGTH: 27
<212> TYPE: DNA
<213> ORGANISM: Artificial Sequence
<220> FEATURE:
<223> OTHER INFORMATION: synthetic

<400> SEQUENCE: 391
caacaatatt atactactcc gatcacc                                        27

<210> SEQ ID NO 392
```

<211> LENGTH: 9
<212> TYPE: PRT
<213> ORGANISM: Artificial Sequence
<220> FEATURE:
<223> OTHER INFORMATION: synthetic

<400> SEQUENCE: 392

Gln Gln Tyr Tyr Thr Thr Pro Ile Thr
1               5

<210> SEQ ID NO 393
<211> LENGTH: 366
<212> TYPE: DNA
<213> ORGANISM: Artificial Sequence
<220> FEATURE:
<223> OTHER INFORMATION: synthetic

<400> SEQUENCE: 393
gaggtgcagc tggtggagtc tgggggaggc ttggtacagc ctggggggtc cctgagactc      60
tcctgtgcag cctccggact catatttagc aactatgtca tgagctgggt ccgccaggct     120
ccagggaagg ggctggagtg ggtctcaggt atcagtggtg atggtgataa cacatactac     180
gcagattccg tgaagggccg gttcaccatt tccagagaca attccaagaa cactctgtat     240
ctgcaaatga acagcctgag agccgagggc acggccatat attactgtgc gaaagatcac     300
cataactgga atcccgtccc ttattttgac tactggggcc agggaaccct ggtcaccgtc     360
tcctca                                                                366

<210> SEQ ID NO 394
<211> LENGTH: 122
<212> TYPE: PRT
<213> ORGANISM: Artificial Sequence
<220> FEATURE:
<223> OTHER INFORMATION: synthetic

<400> SEQUENCE: 394

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Ser Asn Tyr
            20                  25                  30

Val Met Ser Trp Val Arg Gln Ala Pro Gly Lys Gly Leu Glu Trp Val
        35                  40                  45

Ser Gly Ile Ser Gly Asp Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Gly Thr Ala Ile Tyr Tyr Cys
                85                  90                  95

Ala Lys Asp His His Asn Trp Asn Pro Val Pro Tyr Phe Asp Tyr Trp
            100                 105                 110

Gly Gln Gly Thr Leu Val Thr Val Ser Ser
        115                 120

<210> SEQ ID NO 395
<211> LENGTH: 24
<212> TYPE: DNA
<213> ORGANISM: Artificial Sequence
<220> FEATURE:
<223> OTHER INFORMATION: synthetic

<400> SEQUENCE: 395
ggactcatat ttagcaacta tgtc                                              24

<210> SEQ ID NO 396
<211> LENGTH: 8
<212> TYPE: PRT
<213> ORGANISM: Artificial Sequence
<220> FEATURE:
<223> OTHER INFORMATION: synthetic

<400> SEQUENCE: 396

Gly Leu Ile Phe Ser Asn Tyr Val
1               5

<210> SEQ ID NO 397
<211> LENGTH: 24
<212> TYPE: DNA
<213> ORGANISM: Artificial Sequence
<220> FEATURE:
<223> OTHER INFORMATION: synthetic

<400> SEQUENCE: 397
atcagtggtg atggtgataa caca                                              24

<210> SEQ ID NO 398
<211> LENGTH: 8
<212> TYPE: PRT
<213> ORGANISM: Artificial Sequence
<220> FEATURE:
<223> OTHER INFORMATION: synthetic

<400> SEQUENCE: 398

Ile Ser Gly Asp Gly Asp Asn Thr
1               5

<210> SEQ ID NO 399
<211> LENGTH: 45
<212> TYPE: DNA
<213> ORGANISM: Artificial Sequence
<220> FEATURE:
<223> OTHER INFORMATION: synthetic

<400> SEQUENCE: 399
gcgaaagatc accataactg gaatcccgtc ccttattttg actac               45

<210> SEQ ID NO 400
<211> LENGTH: 15
<212> TYPE: PRT
<213> ORGANISM: Artificial Sequence
<220> FEATURE:
<223> OTHER INFORMATION: synthetic

<400> SEQUENCE: 400

Ala Lys Asp His His Asn Trp Asn Pro Val Pro Tyr Phe Asp Tyr
1               5                   10                  15

<210> SEQ ID NO 401
<211> LENGTH: 321
<212> TYPE: DNA
<213> ORGANISM: Artificial Sequence
<220> FEATURE:
<223> OTHER INFORMATION: synthetic

<400> SEQUENCE: 401
gaaattgtga tgacgcagtc tccagccacc ctgtctgtgt ctctagggga aagagacacc       60
ctctcctgta gggccagtca gagtgttagc agcaacttag cctggtacca gcagaaacct      120

```
ggccaggctc ccaggctcct catctatggt gtatccacca gggccactgg tatcccagcc    180
aggttcagtg gcagtgggtc tgggacagag ttcagtctca ccatcagtag cctgcagtct    240
gaagattttg cagtttatta ctgtcagcag tataataact ggccgctcac tttcggcgga    300
gggaccaagg tggagatcaa a                                               321
```

```
<210> SEQ ID NO 402
<211> LENGTH: 107
<212> TYPE: PRT
<213> ORGANISM: Artificial Sequence
<220> FEATURE:
<223> OTHER INFORMATION: synthetic

<400> SEQUENCE: 402

Glu Ile Val Met Thr Gln Ser Pro Ala Thr Leu Ser Val Ser Leu Gly
1               5                   10                  15

Glu Arg Asp Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Val Ser Thr Arg Ala Thr Gly Ile Pro Ala Arg Phe Ser Gly
        50                  55                  60

Ser Gly Ser Gly Thr Glu Phe Ser Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105
```

```
<210> SEQ ID NO 403
<211> LENGTH: 18
<212> TYPE: DNA
<213> ORGANISM: Artificial Sequence
<220> FEATURE:
<223> OTHER INFORMATION: synthetic

<400> SEQUENCE: 403
cagagtgtta gcagcaac                                                    18
```

```
<210> SEQ ID NO 404
<211> LENGTH: 6
<212> TYPE: PRT
<213> ORGANISM: Artificial Sequence
<220> FEATURE:
<223> OTHER INFORMATION: synthetic

<400> SEQUENCE: 404

Gln Ser Val Ser Ser Asn
1               5
```

```
<210> SEQ ID NO 405
<211> LENGTH: 9
<212> TYPE: DNA
<213> ORGANISM: Artificial Sequence
<220> FEATURE:
<223> OTHER INFORMATION: synthetic

<400> SEQUENCE: 405 ggtgtatcc                                                               9
```

```
<210> SEQ ID NO 406
<211> LENGTH: 3
```

```
<212> TYPE: PRT
<213> ORGANISM: Artificial Sequence
<220> FEATURE:
<223> OTHER INFORMATION: synthetic

<400> SEQUENCE: 406

Gly Val Ser
1

<210> SEQ ID NO 407
<211> LENGTH: 27
<212> TYPE: DNA
<213> ORGANISM: Artificial Sequence
<220> FEATURE:
<223> OTHER INFORMATION: synthetic

<400> SEQUENCE: 407
cagcagtata ataactggcc gctcact                                        27

<210> SEQ ID NO 408
<211> LENGTH: 9
<212> TYPE: PRT
<213> ORGANISM: Artificial Sequence
<220> FEATURE:
<223> OTHER INFORMATION: synthetic

<400> SEQUENCE: 408

Gln Gln Tyr Asn Asn Trp Pro Leu Thr
1               5

<210> SEQ ID NO 409
<211> LENGTH: 375
<212> TYPE: DNA
<213> ORGANISM: Artificial Sequence
<220> FEATURE:
<223> OTHER INFORMATION: synthetic

<400> SEQUENCE: 409
gaggtgcagc tggtggagtc tgggggaggc ttggtaaagc cggggggtc ccttagactt      60 tcctgtgcag cctctggatt cactttcact aacgcctgga tgacctgggt ccgccaggct    120
ccagggaagg ggctggagtg ggttggccgt attaaaagta aaactgatgg tgggacaaca    180
gactacgcag cacccgtgaa aggcagattc accatctcaa gagatgattc aaaaaccacg    240
ctgtatctac aaatgaacag cctgagaacc gaggacacag ccgtgtatta ctgttccata    300
gatccgttta gcagtgtctg gtacttctac gctttggacg tctggggcca agggaccacg    360
gtcaccgtct cctca                                                    375

<210> SEQ ID NO 410
<211> LENGTH: 125
<212> TYPE: PRT
<213> ORGANISM: Artificial Sequence
<220> FEATURE:
<223> OTHER INFORMATION: synthetic

<400> SEQUENCE: 410

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Thr Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
```

```
                50                  55                  60
Pro Val Lys Gly Arg Phe Thr Ile Ser Arg Asp Asp Ser Lys Thr Thr
 65                  70                  75                  80

Leu Tyr Leu Gln Met Asn Ser Leu Arg Thr Glu Asp Thr Ala Val Tyr
                 85                  90                  95

Tyr Cys Ser Ile Asp Pro Phe Ser Ser Val Trp Tyr Phe Tyr Ala Leu
                100                 105                 110

Asp Val Trp Gly Gln Gly Thr Thr Val Thr Val Ser Ser
            115                 120                 125
```

<210> SEQ ID NO 411
<211> LENGTH: 24
<212> TYPE: DNA
<213> ORGANISM: Artificial Sequence
<220> FEATURE:
<223> OTHER INFORMATION: synthetic

<400> SEQUENCE: 411
ggattcactt tcactaacgc ctgg                                          24

<210> SEQ ID NO 412
<211> LENGTH: 8
<212> TYPE: PRT
<213> ORGANISM: Artificial Sequence
<220> FEATURE:
<223> OTHER INFORMATION: synthetic

<400> SEQUENCE: 412

```
Gly Phe Thr Phe Thr Asn Ala Trp
 1               5
```

<210> SEQ ID NO 413
<211> LENGTH: 30
<212> TYPE: DNA
<213> ORGANISM: Artificial Sequence
<220> FEATURE:
<223> OTHER INFORMATION: synthetic

<400> SEQUENCE: 413
attaaaagta aaactgatgg tgggacaaca                                    30

<210> SEQ ID NO 414
<211> LENGTH: 10
<212> TYPE: PRT
<213> ORGANISM: Artificial Sequence
<220> FEATURE:
<223> OTHER INFORMATION: synthetic

<400> SEQUENCE: 414

```
Ile Lys Ser Lys Thr Asp Gly Gly Thr Thr
 1               5                  10
```

<210> SEQ ID NO 415
<211> LENGTH: 48
<212> TYPE: DNA
<213> ORGANISM: Artificial Sequence
<220> FEATURE:
<223> OTHER INFORMATION: synthetic

<400> SEQUENCE: 415
tccatagatc cgtttagcag tgtctggtac ttctacgctt tggacgtc                48

<210> SEQ ID NO 416
<211> LENGTH: 16

```
<212> TYPE: PRT
<213> ORGANISM: Artificial Sequence
<220> FEATURE:
<223> OTHER INFORMATION: synthetic

<400> SEQUENCE: 416

Ser Ile Asp Pro Phe Ser Ser Val Trp Tyr Phe Tyr Ala Leu Asp Val
1               5                   10                  15

<210> SEQ ID NO 417
<211> LENGTH: 321
<212> TYPE: DNA
<213> ORGANISM: Artificial Sequence
<220> FEATURE:
<223> OTHER INFORMATION: synthetic

<400> SEQUENCE: 417
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag catgatagtt ccctcccac tttcggcgga    300 gggaccaagg tggagatcaa a                                              321

<210> SEQ ID NO 418
<211> LENGTH: 107
<212> TYPE: PRT
<213> ORGANISM: Artificial Sequence
<220> FEATURE:
<223> OTHER INFORMATION: synthetic

<400> SEQUENCE: 418

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ser Ser Phe Pro Pro
                85                  90                  95

Thr Phe Gly Gly Gly Thr Lys Val Glu Ile Lys
        100                 105

<210> SEQ ID NO 419
<211> LENGTH: 18
<212> TYPE: DNA
<213> ORGANISM: Artificial Sequence
<220> FEATURE:
<223> OTHER INFORMATION: synthetic

<400> SEQUENCE: 419
cagggcatta gaaatgat                                                   18

<210> SEQ ID NO 420
<211> LENGTH: 6
<212> TYPE: PRT
```

<210> SEQ ID NO 421
<211> LENGTH: 9
<212> TYPE: DNA
<213> ORGANISM: Artificial Sequence
<220> FEATURE:
<223> OTHER INFORMATION: synthetic

<400> SEQUENCE: 420

Gln Gly Ile Arg Asn Asp
1               5

<210> SEQ ID NO 421
<211> LENGTH: 9
<212> TYPE: DNA
<213> ORGANISM: Artificial Sequence
<220> FEATURE:
<223> OTHER INFORMATION: synthetic

<400> SEQUENCE: 421 gctgcatcc                                                                9

<210> SEQ ID NO 422
<211> LENGTH: 3
<212> TYPE: PRT
<213> ORGANISM: Artificial Sequence
<220> FEATURE:
<223> OTHER INFORMATION: synthetic

<400> SEQUENCE: 422

Ala Ala Ser
1

<210> SEQ ID NO 423
<211> LENGTH: 27
<212> TYPE: DNA
<213> ORGANISM: Artificial Sequence
<220> FEATURE:
<223> OTHER INFORMATION: synthetic

<400> SEQUENCE: 423
ctacagcatg atagtttccc tcccact                                           27

<210> SEQ ID NO 424
<211> LENGTH: 9
<212> TYPE: PRT
<213> ORGANISM: Artificial Sequence
<220> FEATURE:
<223> OTHER INFORMATION: synthetic

<400> SEQUENCE: 424

Leu Gln His Asp Ser Phe Pro Pro Thr
1               5

<210> SEQ ID NO 425
<211> LENGTH: 375
<212> TYPE: DNA
<213> ORGANISM: Artificial Sequence
<220> FEATURE:
<223> OTHER INFORMATION: synthetic

<400> SEQUENCE: 425
caggtgcagc tggtggagtc tggggggaggc gtggtccagc ctgggaggtc cctgaaactc      60
tcttgtgcag cgtctggatt caccttcagt aactatggca tgcactgggt ccgccaggct     120
ccaggcaagg ggctggagtg ggtgtcagtt atattatttg atggaagtga taaatactat     180
gcagactccg tgaagggccg attcaccatc tccagagaca attccaagaa cacgctgtat     240
ctgcaaatga acagcctgag agccgaggac acggctgtgt attactgtgc gagagatacc     300

```
ggcgggcgat ttttggagtg gttatccgat gcttttgata tctggggcca agggacaatg      360
gtcaccgtct cttca                                                       375
```

<210> SEQ ID NO 426
<211> LENGTH: 125
<212> TYPE: PRT
<213> ORGANISM: Artificial Sequence
<220> FEATURE:
<223> OTHER INFORMATION: synthetic

<400> SEQUENCE: 426

```
Gln Val Gln Leu Val Glu Ser Gly Gly Gly Val Val Gln Pro Gly Arg
1               5                   10                  15

Ser Leu Lys Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Val Ile Leu Phe Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Gly Arg Phe Leu Glu Trp Leu Ser Asp Ala Phe
            100                 105                 110

Asp Ile Trp Gly Gln Gly Thr Met Val Thr Val Ser Ser
        115                 120                 125
```

<210> SEQ ID NO 427
<211> LENGTH: 24
<212> TYPE: DNA
<213> ORGANISM: Artificial Sequence
<220> FEATURE:
<223> OTHER INFORMATION: synthetic

<400> SEQUENCE: 427

```
ggattcacct tcagtaacta tggc                                             24
```

<210> SEQ ID NO 428
<211> LENGTH: 8
<212> TYPE: PRT
<213> ORGANISM: Artificial Sequence
<220> FEATURE:
<223> OTHER INFORMATION: synthetic

<400> SEQUENCE: 428

```
Gly Phe Thr Phe Ser Asn Tyr Gly
1               5
```

<210> SEQ ID NO 429
<211> LENGTH: 24
<212> TYPE: DNA
<213> ORGANISM: Artificial Sequence
<220> FEATURE:
<223> OTHER INFORMATION: synthetic

<400> SEQUENCE: 429

```
atattatttg atggaagtga taaa                                             24
```

<210> SEQ ID NO 430
<211> LENGTH: 8
<212> TYPE: PRT

<210> SEQ ID NO 430
<211> LENGTH: 8
<212> TYPE: PRT
<213> ORGANISM: Artificial Sequence
<220> FEATURE:
<223> OTHER INFORMATION: synthetic

<400> SEQUENCE: 430

Ile Leu Phe Asp Gly Ser Asp Lys
1               5

<210> SEQ ID NO 431
<211> LENGTH: 54
<212> TYPE: DNA
<213> ORGANISM: Artificial Sequence
<220> FEATURE:
<223> OTHER INFORMATION: synthetic

<400> SEQUENCE: 431
gcgagagata ccggcgggcg atttttggag tggttatccg atgctttga tatc          54

<210> SEQ ID NO 432
<211> LENGTH: 18
<212> TYPE: PRT
<213> ORGANISM: Artificial Sequence
<220> FEATURE:
<223> OTHER INFORMATION: synthetic

<400> SEQUENCE: 432

Ala Arg Asp Thr Gly Gly Arg Phe Leu Glu Trp Leu Ser Asp Ala Phe
1               5                   10                  15

Asp Ile

<210> SEQ ID NO 433
<211> LENGTH: 321
<212> TYPE: DNA
<213> ORGANISM: Artificial Sequence
<220> FEATURE:
<223> OTHER INFORMATION: synthetic

<400> SEQUENCE: 433
gccatccaga tgacccagtc tccatcctcc ctgtctacat ctgtaggaga cagagtcacc    60
atcacttgcc gggcgagtca ggacattaga aatgatttag ctggtatca gcagaaacca   120
gggaaagccc ctaagctcct gatctatgct gcatccaatt tacaaagtgg ggtcccatca   180
agtttcagcg gcagtggatc tggcacagat ttcactctca ccatcagcag cctgcagcct   240
gaagattttg caacttatta ctgtctgcaa aattacaatt acccgtacac ttttggccag   300
gggaccaagc tggagatcaa a                                             321

<210> SEQ ID NO 434
<211> LENGTH: 107
<212> TYPE: PRT
<213> ORGANISM: Artificial Sequence
<220> FEATURE:
<223> OTHER INFORMATION: synthetic

<400> SEQUENCE: 434

Ala Ile Gln Met Thr Gln Ser Pro Ser Ser Leu Ser Thr Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Tyr Asn Tyr Pro Tyr
                85                  90                  95

Thr Phe Gly Gln Gly Thr Lys Leu Glu Ile Lys
            100                 105

<210> SEQ ID NO 435
<211> LENGTH: 18
<212> TYPE: DNA
<213> ORGANISM: Artificial Sequence
<220> FEATURE:
<223> OTHER INFORMATION: synthetic

<400> SEQUENCE: 435
caggacatta gaaatgat                                                 18

<210> SEQ ID NO 436
<211> LENGTH: 6
<212> TYPE: PRT
<213> ORGANISM: Artificial Sequence
<220> FEATURE:
<223> OTHER INFORMATION: synthetic

<400> SEQUENCE: 436

Gln Asp Ile Arg Asn Asp
1               5

<210> SEQ ID NO 437
<211> LENGTH: 9
<212> TYPE: DNA
<213> ORGANISM: Artificial Sequence
<220> FEATURE:
<223> OTHER INFORMATION: synthetic

<400> SEQUENCE: 437 gctgcatcc                                                            9

<210> SEQ ID NO 438
<211> LENGTH: 3
<212> TYPE: PRT
<213> ORGANISM: Artificial Sequence
<220> FEATURE:
<223> OTHER INFORMATION: synthetic

<400> SEQUENCE: 438

Ala Ala Ser
1

<210> SEQ ID NO 439
<211> LENGTH: 27
<212> TYPE: DNA
<213> ORGANISM: Artificial Sequence
<220> FEATURE:
<223> OTHER INFORMATION: synthetic

<400> SEQUENCE: 439
ctgcaaaatt acaattaccc gtacact                                       27

<210> SEQ ID NO 440
<211> LENGTH: 9
<212> TYPE: PRT
<213> ORGANISM: Artificial Sequence
<220> FEATURE:
<223> OTHER INFORMATION: synthetic

<400> SEQUENCE: 440

Leu Gln Asn Tyr Asn Tyr Pro Tyr Thr
1               5

<210> SEQ ID NO 441
<211> LENGTH: 381
<212> TYPE: DNA
<213> ORGANISM: Artificial Sequence
<220> FEATURE:
<223> OTHER INFORMATION: synthetic

<400> SEQUENCE: 441

```
gaagtgcagc tggtggagtc tggcggaggc ttggtgcagc ctggcaggtc cctgagactc    60
tcctgtgcag cctctggatt cacctttgat gcttttacca tgcactgggt ccggcacgtt   120
ccagggaagg gcctggagtg ggtctcaggt attagttgga atagtgatag tatagcctat   180
gcggactctg tgaagggccg attcaccatg tccagagaca acgccaagaa ctccctgtat   240
ctgcaaatga acagtctgag aggtgaggac acggccttct attactgtgc aaaagatctg   300
acgtatgtct ggaaccggga ctaccactac tatttcggta tggacgtctg gggccaaggg   360
accacggtca ccgtctcctc a                                             381
```

<210> SEQ ID NO 442
<211> LENGTH: 127
<212> TYPE: PRT
<213> ORGANISM: Artificial Sequence
<220> FEATURE:
<223> OTHER INFORMATION: synthetic

<400> SEQUENCE: 442

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Phe
            20                  25                  30

Thr Met His Trp Val Arg His Val Pro Gly Lys Gly Leu Glu Trp Val
        35                  40                  45

Ser Gly Ile Ser Trp Asn Ser Asp Ser Ile Ala Tyr Ala Asp Ser Val
    50                  55                  60

Lys Gly Arg Phe Thr Met Ser Arg Asp Asn Ala Lys Asn Ser Leu Tyr
65                  70                  75                  80

Leu Gln Met Asn Ser Leu Arg Gly Glu Asp Thr Ala Phe Tyr Tyr Cys
                85                  90                  95

Ala Lys Asp Leu Thr Tyr Val Trp Asn Arg Asp Tyr His Tyr Tyr Phe
            100                 105                 110

Gly Met Asp Val Trp Gly Gln Gly Thr Thr Val Thr Val Ser Ser
        115                 120                 125

<210> SEQ ID NO 443
<211> LENGTH: 24
<212> TYPE: DNA
<213> ORGANISM: Artificial Sequence
<220> FEATURE:
<223> OTHER INFORMATION: synthetic

<400> SEQUENCE: 443

```
ggattcacct ttgatgcttt tacc                                           24
```

<210> SEQ ID NO 444
<211> LENGTH: 8

```
<212> TYPE: PRT
<213> ORGANISM: Artificial Sequence
<220> FEATURE:
<223> OTHER INFORMATION: synthetic

<400> SEQUENCE: 444

Gly Phe Thr Phe Asp Ala Phe Thr
1               5

<210> SEQ ID NO 445
<211> LENGTH: 24
<212> TYPE: DNA
<213> ORGANISM: Artificial Sequence
<220> FEATURE:
<223> OTHER INFORMATION: synthetic

<400> SEQUENCE: 445
attagttgga atagtgatag tata                                         24

<210> SEQ ID NO 446
<211> LENGTH: 8
<212> TYPE: PRT
<213> ORGANISM: Artificial Sequence
<220> FEATURE:
<223> OTHER INFORMATION: synthetic

<400> SEQUENCE: 446

Ile Ser Trp Asn Ser Asp Ser Ile
1               5

<210> SEQ ID NO 447
<211> LENGTH: 60
<212> TYPE: DNA
<213> ORGANISM: Artificial Sequence
<220> FEATURE:
<223> OTHER INFORMATION: synthetic

<400> SEQUENCE: 447
gcaaaagatc tgacgtatgt ctggaaccgg gactaccact actatttcgg tatggacgtc   60

<210> SEQ ID NO 448
<211> LENGTH: 20
<212> TYPE: PRT
<213> ORGANISM: Artificial Sequence
<220> FEATURE:
<223> OTHER INFORMATION: synthetic

<400> SEQUENCE: 448

Ala Lys Asp Leu Thr Tyr Val Trp Asn Arg Asp Tyr His Tyr Tyr Phe
1               5                   10                  15

Gly Met Asp Val
            20

<210> SEQ ID NO 449
<211> LENGTH: 321
<212> TYPE: DNA
<213> ORGANISM: Artificial Sequence
<220> FEATURE:
<223> OTHER INFORMATION: synthetic

<400> SEQUENCE: 449
gacatccaga tgacccagtc tccatcctcc ctgtctgcat ctgtaggaga cagagtcacc   60
atcacttgcc ggacaagtca gagcattagt aactatttaa attggtatca gcagaaacca  120
gggaaagccc ctaaactcct gatctatact gcatccagtt tgcaaagtgg ggtcccatca  180
```

```
aggttcagtg gcagtggatc tgggacagat ttcactctca ccatcagcag tctgcaacct    240
gaagattttg caacttacta ctgtcaacag agttacagta ccccgatcac cttcggccaa    300
gggacacgac tggagattaa a                                              321
```

```
<210> SEQ ID NO 450
<211> LENGTH: 107
<212> TYPE: PRT
<213> ORGANISM: Artificial Sequence
<220> FEATURE:
<223> OTHER INFORMATION: synthetic

<400> SEQUENCE: 450

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105
```

```
<210> SEQ ID NO 451
<211> LENGTH: 18
<212> TYPE: DNA
<213> ORGANISM: Artificial Sequence
<220> FEATURE:
<223> OTHER INFORMATION: synthetic

<400> SEQUENCE: 451
cagagcatta gtaactat                                                  18
```

```
<210> SEQ ID NO 452
<211> LENGTH: 6
<212> TYPE: PRT
<213> ORGANISM: Artificial Sequence
<220> FEATURE:
<223> OTHER INFORMATION: synthetic

<400> SEQUENCE: 452

Gln Ser Ile Ser Asn Tyr
1               5
```

```
<210> SEQ ID NO 453
<211> LENGTH: 9
<212> TYPE: DNA
<213> ORGANISM: Artificial Sequence
<220> FEATURE:
<223> OTHER INFORMATION: synthetic

<400> SEQUENCE: 453 actgcatcc                                                            9
```

```
<210> SEQ ID NO 454
<211> LENGTH: 3
<212> TYPE: PRT
<213> ORGANISM: Artificial Sequence
```

<220> FEATURE:
<223> OTHER INFORMATION: synthetic

<400> SEQUENCE: 454

Thr Ala Ser
1

<210> SEQ ID NO 455
<211> LENGTH: 27
<212> TYPE: DNA
<213> ORGANISM: Artificial Sequence
<220> FEATURE:
<223> OTHER INFORMATION: synthetic

<400> SEQUENCE: 455
caacagagtt acagtacccc gatcacc                                          27

<210> SEQ ID NO 456
<211> LENGTH: 9
<212> TYPE: PRT
<213> ORGANISM: Artificial Sequence
<220> FEATURE:
<223> OTHER INFORMATION: synthetic

<400> SEQUENCE: 456

Gln Gln Ser Tyr Ser Thr Pro Ile Thr
1               5

<210> SEQ ID NO 457
<211> LENGTH: 375
<212> TYPE: DNA
<213> ORGANISM: Artificial Sequence
<220> FEATURE:
<223> OTHER INFORMATION: synthetic

<400> SEQUENCE: 457
gaagtgcagc tggtggagtc tgggggaggc ttggtacagc ctggcaggtc cctgagactc        60
tcctgtgtag cctctggatt caccttt gat gattacgcca tgcactgggt ccggcaagtt     120
ccagggaagg gcctggagtg ggtctcaggg attacttgga atagtggtaa gttagactat      180
gcggactctg tgaagggccg attcaccatc tccagagaca cgccaagaa ctccctcttt       240 ctgcaaatga acagtctgag agctgaggac acggccttgt attactgtgc aaaagatatg      300
gagggatggt ataactggaa ctatttttt ggttttcata tatgggggcca agggacaatg      360 gtcaccgtct cttca                                                       375

<210> SEQ ID NO 458
<211> LENGTH: 125
<212> TYPE: PRT
<213> ORGANISM: Artificial Sequence
<220> FEATURE:
<223> OTHER INFORMATION: synthetic

<400> SEQUENCE: 458

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Thr Trp Asn Ser Gly Lys Leu Asp Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Leu Tyr Tyr Cys
                85                  90                  95

Ala Lys Asp Met Glu Gly Trp Tyr Asn Trp Asn Tyr Phe Phe Gly Phe
            100                 105                 110

His Ile Trp Gly Gln Gly Thr Met Val Thr Val Ser Ser
            115                 120                 125

<210> SEQ ID NO 459
<211> LENGTH: 24
<212> TYPE: DNA
<213> ORGANISM: Artificial Sequence
<220> FEATURE:
<223> OTHER INFORMATION: synthetic

<400> SEQUENCE: 459
ggattcacct ttgatgatta cgcc                                           24

<210> SEQ ID NO 460
<211> LENGTH: 8
<212> TYPE: PRT
<213> ORGANISM: Artificial Sequence
<220> FEATURE:
<223> OTHER INFORMATION: synthetic

<400> SEQUENCE: 460

Gly Phe Thr Phe Asp Asp Tyr Ala
1               5

<210> SEQ ID NO 461
<211> LENGTH: 24
<212> TYPE: DNA
<213> ORGANISM: Artificial Sequence
<220> FEATURE:
<223> OTHER INFORMATION: synthetic

<400> SEQUENCE: 461
attacttgga atagtggtaa gtta                                           24

<210> SEQ ID NO 462
<211> LENGTH: 8
<212> TYPE: PRT
<213> ORGANISM: Artificial Sequence
<220> FEATURE:
<223> OTHER INFORMATION: synthetic

<400> SEQUENCE: 462

Ile Thr Trp Asn Ser Gly Lys Leu
1               5

<210> SEQ ID NO 463
<211> LENGTH: 54
<212> TYPE: DNA
<213> ORGANISM: Artificial Sequence
<220> FEATURE:
<223> OTHER INFORMATION: synthetic

<400> SEQUENCE: 463
gcaaaagata tggagggatg gtataactgg aactattttt tggttttca tata           54

<210> SEQ ID NO 464
<211> LENGTH: 18
<212> TYPE: PRT
<213> ORGANISM: Artificial Sequence
<220> FEATURE:
<223> OTHER INFORMATION: synthetic

<400> SEQUENCE: 464

Ala Lys Asp Met Glu Gly Trp Tyr Asn Trp Asn Tyr Phe Phe Gly Phe
1               5                   10                  15

His Ile

<210> SEQ ID NO 465
<211> LENGTH: 324
<212> TYPE: DNA
<213> ORGANISM: Artificial Sequence
<220> FEATURE:
<223> OTHER INFORMATION: synthetic

<400> SEQUENCE: 465
gacatccaga tgacccagtc tccatcctcc ctgtctgcat ctgtaggaga cagagtcacc     60
atcacttgcc gggcaagtcg aacataggc agcttttta attggtatca gcagaaacca    120
gggaaagccc ctaagctcct gatctatgct gcatccagtt tgcaaagtgg ggtcccatca    180
aggttcagtg gcagtggatc tgggacagat tcactctca tcatcagcag tctgcaacct    240
gaagattttg caacttacta ctgtcaacag agttacagta tacctccgat caccttcggc    300
caagggacac gactggagat taaa                                           324

<210> SEQ ID NO 466
<211> LENGTH: 108
<212> TYPE: PRT
<213> ORGANISM: Artificial Sequence
<220> FEATURE:
<223> OTHER INFORMATION: synthetic

<400> SEQUENCE: 466

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asn Ile Gly Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Ile Ile Ser Ser Leu Gln Pro
65                  70                  75                  80

Glu Asp Phe Ala Thr Tyr Tyr Cys Gln Gln Ser Tyr Ser Ile Pro Pro
                85                  90                  95

Ile Thr Phe Gly Gln Gly Thr Arg Leu Glu Ile Lys
            100                 105

<210> SEQ ID NO 467
<211> LENGTH: 18
<212> TYPE: DNA
<213> ORGANISM: Artificial Sequence
<220> FEATURE:
<223> OTHER INFORMATION: synthetic

<400> SEQUENCE: 467
cggaacatag gcagcttt                                                   18

<210> SEQ ID NO 468
<211> LENGTH: 6
<212> TYPE: PRT

```
<213> ORGANISM: Artificial Sequence
<220> FEATURE:
<223> OTHER INFORMATION: synthetic

<400> SEQUENCE: 468

Arg Asn Ile Gly Ser Phe
1               5

<210> SEQ ID NO 469
<211> LENGTH: 9
<212> TYPE: DNA
<213> ORGANISM: Artificial Sequence
<220> FEATURE:
<223> OTHER INFORMATION: synthetic

<400> SEQUENCE: 469 gctgcatcc                                                             9

<210> SEQ ID NO 470
<211> LENGTH: 3
<212> TYPE: PRT
<213> ORGANISM: Artificial Sequence
<220> FEATURE:
<223> OTHER INFORMATION: synthetic

<400> SEQUENCE: 470

Ala Ala Ser
1

<210> SEQ ID NO 471
<211> LENGTH: 30
<212> TYPE: DNA
<213> ORGANISM: Artificial Sequence
<220> FEATURE:
<223> OTHER INFORMATION: synthetic

<400> SEQUENCE: 471
caacagagtt acagtatacc tccgatcacc                                     30

<210> SEQ ID NO 472
<211> LENGTH: 10
<212> TYPE: PRT
<213> ORGANISM: Artificial Sequence
<220> FEATURE:
<223> OTHER INFORMATION: synthetic

<400> SEQUENCE: 472

Gln Gln Ser Tyr Ser Ile Pro Pro Ile Thr
1               5                   10

<210> SEQ ID NO 473
<211> LENGTH: 375
<212> TYPE: DNA
<213> ORGANISM: Artificial Sequence
<220> FEATURE:
<223> OTHER INFORMATION: synthetic

<400> SEQUENCE: 473
gaggtgcagc tggtggagtc tgggggagac ttggtaaagc cggggggtc ccttggactc      60 tcctgtgcag cctctggatt cactttcagt gacgcctgga tgaactgggt ccgccaggct    120
ccagggaagg ggctggagtg ggttggccgt attaaaagca aaactgatga tgggacaaca    180
gacttcgctg cacccgtaaa aggcagattc accatctcaa gagatgattc aaaaaacacg    240
ctgtatctgc aaatgaacag cctgaaaacc gacgacacag ccatgtatta ctgtaccaca    300
```

```
gatttcttcc actataactg ggactactct tttttttgact actggggccg gggaaccctg   360
gtcaccgtct cctca                                                    375
```

<210> SEQ ID NO 474
<211> LENGTH: 125
<212> TYPE: PRT
<213> ORGANISM: Artificial Sequence
<220> FEATURE:
<223> OTHER INFORMATION: synthetic

<400> SEQUENCE: 474

```
Glu Val Gln Leu Val Glu Ser Gly Gly Asp Leu Val Lys Pro Gly Gly
1               5                   10                  15

Ser Leu Gly Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Asp Gly Thr Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Asp Asp Thr Ala Met Tyr
                85                  90                  95

Tyr Cys Thr Thr Asp Phe Phe His Tyr Asn Trp Asp Tyr Ser Phe Phe
            100                 105                 110

Asp Tyr Trp Gly Arg Gly Thr Leu Val Thr Val Ser Ser
        115                 120                 125
```

<210> SEQ ID NO 475
<211> LENGTH: 24
<212> TYPE: DNA
<213> ORGANISM: Artificial Sequence
<220> FEATURE:
<223> OTHER INFORMATION: synthetic

<400> SEQUENCE: 475

```
ggattcactt tcagtgacgc ctgg                                          24
```

<210> SEQ ID NO 476
<211> LENGTH: 8
<212> TYPE: PRT
<213> ORGANISM: Artificial Sequence
<220> FEATURE:
<223> OTHER INFORMATION: synthetic

<400> SEQUENCE: 476

```
Gly Phe Thr Phe Ser Asp Ala Trp
1               5
```

<210> SEQ ID NO 477
<211> LENGTH: 30
<212> TYPE: DNA
<213> ORGANISM: Artificial Sequence
<220> FEATURE:
<223> OTHER INFORMATION: synthetic

<400> SEQUENCE: 477

```
attaaaagca aaactgatga tgggacaaca                                    30
```

<210> SEQ ID NO 478
<211> LENGTH: 10
<212> TYPE: PRT

```
<213> ORGANISM: Artificial Sequence
<220> FEATURE:
<223> OTHER INFORMATION: synthetic

<400> SEQUENCE: 478

Ile Lys Ser Lys Thr Asp Asp Gly Thr Thr
1               5                   10

<210> SEQ ID NO 479
<211> LENGTH: 48
<212> TYPE: DNA
<213> ORGANISM: Artificial Sequence
<220> FEATURE:
<223> OTHER INFORMATION: synthetic

<400> SEQUENCE: 479
accacagatt tcttccacta taactgggac tactctttt ttgactac            48

<210> SEQ ID NO 480
<211> LENGTH: 16
<212> TYPE: PRT
<213> ORGANISM: Artificial Sequence
<220> FEATURE:
<223> OTHER INFORMATION: synthetic

<400> SEQUENCE: 480

Thr Thr Asp Phe Phe His Tyr Asn Trp Asp Tyr Ser Phe Phe Asp Tyr
1               5                   10                  15

<210> SEQ ID NO 481
<211> LENGTH: 324
<212> TYPE: DNA
<213> ORGANISM: Artificial Sequence
<220> FEATURE:
<223> OTHER INFORMATION: synthetic

<400> SEQUENCE: 481
gacatccaga tgacccagtc tccatcctcc ctgtctgcat ctgtaggaga cagagtcacc       60
atcacttgcc gggcaagtca gagcattagc tactatttaa attggtatca gcagaaacca      120
gggaaagccc ctaaactcct gatctatgct gcatccactt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                             324

<210> SEQ ID NO 482
<211> LENGTH: 108
<212> TYPE: PRT
<213> ORGANISM: Artificial Sequence
<220> FEATURE:
<223> OTHER INFORMATION: synthetic

<400> SEQUENCE: 482

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Tyr Tyr
                20                  25                  30

Leu Asn Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Thr Pro Pro
                85                  90                  95
Ile Thr Phe Gly Gln Gly Thr Arg Leu Glu Ile Lys
            100                 105
```

<210> SEQ ID NO 483
<211> LENGTH: 18
<212> TYPE: DNA
<213> ORGANISM: Artificial Sequence
<220> FEATURE:
<223> OTHER INFORMATION: synthetic

<400> SEQUENCE: 483
cagagcatta gctactat                                                     18

<210> SEQ ID NO 484
<211> LENGTH: 6
<212> TYPE: PRT
<213> ORGANISM: Artificial Sequence
<220> FEATURE:
<223> OTHER INFORMATION: synthetic

<400> SEQUENCE: 484

```
Gln Ser Ile Ser Tyr Tyr
1               5
```

<210> SEQ ID NO 485
<211> LENGTH: 9
<212> TYPE: DNA
<213> ORGANISM: Artificial Sequence
<220> FEATURE:
<223> OTHER INFORMATION: synthetic

<400> SEQUENCE: 485 gctgcatcc                                                                9

<210> SEQ ID NO 486
<211> LENGTH: 3
<212> TYPE: PRT
<213> ORGANISM: Artificial Sequence
<220> FEATURE:
<223> OTHER INFORMATION: synthetic

<400> SEQUENCE: 486

```
Ala Ala Ser
1
```

<210> SEQ ID NO 487
<211> LENGTH: 30
<212> TYPE: DNA
<213> ORGANISM: Artificial Sequence
<220> FEATURE:
<223> OTHER INFORMATION: synthetic

<400> SEQUENCE: 487
caacagagtt acagtacccc tccgatcacc                                        30

<210> SEQ ID NO 488
<211> LENGTH: 10
<212> TYPE: PRT
<213> ORGANISM: Artificial Sequence
<220> FEATURE:
<223> OTHER INFORMATION: synthetic

<400> SEQUENCE: 488

Gln Gln Ser Tyr Ser Thr Pro Pro Ile Thr
1               5                   10

<210> SEQ ID NO 489
<211> LENGTH: 378
<212> TYPE: DNA
<213> ORGANISM: Artificial Sequence
<220> FEATURE:
<223> OTHER INFORMATION: synthetic

<400> SEQUENCE: 489
caggtgcagc tggtggagtc tgggggaggc ttggtcaagc ctggagggtc cctgagactc    60
tcctgtacag cctctggatt caccttcagt gactactaca tgagctggat ccgccaggct   120
ccagggaagg gactggagtg ggtttcatac attagtagta gtggaaatac catatactac   180
gcagactctg tgaagggccg attcaccatc tccagggaca acgccaagaa ctcactgtat   240
ctgcaaatga acagcctgag agccgaggac acggccgtgt attactgtgc gagacttggg   300
atattcctat ggttcgggga gttattcctt gatgcttttg atatctgggg ccaagggaca   360
atggtcaccg tctcttca                                                 378

<210> SEQ ID NO 490
<211> LENGTH: 126
<212> TYPE: PRT
<213> ORGANISM: Artificial Sequence
<220> FEATURE:
<223> OTHER INFORMATION: synthetic

<400> SEQUENCE: 490

Gln Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ile Phe Leu Trp Phe Gly Glu Leu Phe Leu Asp Ala
            100                 105                 110

Phe Asp Ile Trp Gly Gln Gly Thr Met Val Thr Val Ser Ser
        115                 120                 125

<210> SEQ ID NO 491
<211> LENGTH: 24
<212> TYPE: DNA
<213> ORGANISM: Artificial Sequence
<220> FEATURE:
<223> OTHER INFORMATION: synthetic

<400> SEQUENCE: 491
ggattcacct tcagtgacta ctac                                           24

<210> SEQ ID NO 492
<211> LENGTH: 8
<212> TYPE: PRT
<213> ORGANISM: Artificial Sequence
<220> FEATURE:
<223> OTHER INFORMATION: synthetic

<400> SEQUENCE: 492

Gly Phe Thr Phe Ser Asp Tyr Tyr
1               5

<210> SEQ ID NO 493
<211> LENGTH: 24
<212> TYPE: DNA
<213> ORGANISM: Artificial Sequence
<220> FEATURE:
<223> OTHER INFORMATION: synthetic

<400> SEQUENCE: 493
attagtagta gtggaaatac cata                                          24

<210> SEQ ID NO 494
<211> LENGTH: 8
<212> TYPE: PRT
<213> ORGANISM: Artificial Sequence
<220> FEATURE:
<223> OTHER INFORMATION: synthetic

<400> SEQUENCE: 494

Ile Ser Ser Ser Gly Asn Thr Ile
1               5

<210> SEQ ID NO 495
<211> LENGTH: 57
<212> TYPE: DNA
<213> ORGANISM: Artificial Sequence
<220> FEATURE:
<223> OTHER INFORMATION: synthetic

<400> SEQUENCE: 495
gcgagacttg ggatattcct atggttcggg gagttattcc ttgatgcttt tgatatc      57

<210> SEQ ID NO 496
<211> LENGTH: 19
<212> TYPE: PRT
<213> ORGANISM: Artificial Sequence
<220> FEATURE:
<223> OTHER INFORMATION: synthetic

<400> SEQUENCE: 496

Ala Arg Leu Gly Ile Phe Leu Trp Phe Gly Glu Leu Phe Leu Asp Ala
1               5                   10                  15

Phe Asp Ile

<210> SEQ ID NO 497
<211> LENGTH: 324
<212> TYPE: DNA
<213> ORGANISM: Artificial Sequence
<220> FEATURE:
<223> OTHER INFORMATION: synthetic

<400> SEQUENCE: 497
gacatccaga tgacccagtc tccatcctcc ctgtctgcat ctgtaggaga cagagtcacc    60
atcacttgcc gggcaagtca gatcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta tccctccgat caccttcggc   300

-continued caagggacac gactggagat taaa                                        324

<210> SEQ ID NO 498
<211> LENGTH: 108
<212> TYPE: PRT
<213> ORGANISM: Artificial Sequence
<220> FEATURE:
<223> OTHER INFORMATION: synthetic

<400> SEQUENCE: 498

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Pro
                85                  90                  95

Ile Thr Phe Gly Gln Gly Thr Arg Leu Glu Ile Lys
            100                 105

<210> SEQ ID NO 499
<211> LENGTH: 18
<212> TYPE: DNA
<213> ORGANISM: Artificial Sequence
<220> FEATURE:
<223> OTHER INFORMATION: synthetic

<400> SEQUENCE: 499
cagatcatta gcagctat                                               18

<210> SEQ ID NO 500
<211> LENGTH: 6
<212> TYPE: PRT
<213> ORGANISM: Artificial Sequence
<220> FEATURE:
<223> OTHER INFORMATION: synthetic

<400> SEQUENCE: 500

Gln Ile Ile Ser Ser Tyr
1               5

<210> SEQ ID NO 501
<211> LENGTH: 9
<212> TYPE: DNA
<213> ORGANISM: Artificial Sequence
<220> FEATURE:
<223> OTHER INFORMATION: synthetic

<400> SEQUENCE: 501 gctgcatcc                                                         9

<210> SEQ ID NO 502
<211> LENGTH: 3
<212> TYPE: PRT
<213> ORGANISM: Artificial Sequence
<220> FEATURE:
<223> OTHER INFORMATION: synthetic

<400> SEQUENCE: 502

Ala Ala Ser
1

<210> SEQ ID NO 503
<211> LENGTH: 30
<212> TYPE: DNA
<213> ORGANISM: Artificial Sequence
<220> FEATURE:
<223> OTHER INFORMATION: synthetic

<400> SEQUENCE: 503
caacagagtt acagtatccc tccgatcacc                                         30

<210> SEQ ID NO 504
<211> LENGTH: 10
<212> TYPE: PRT
<213> ORGANISM: Artificial Sequence
<220> FEATURE:
<223> OTHER INFORMATION: synthetic

<400> SEQUENCE: 504

Gln Gln Ser Tyr Ser Ile Pro Pro Ile Thr
1               5                   10

<210> SEQ ID NO 505
<211> LENGTH: 381
<212> TYPE: DNA
<213> ORGANISM: Artificial Sequence
<220> FEATURE:
<223> OTHER INFORMATION: synthetic

<400> SEQUENCE: 505
gaggtgcagc tgttggagtc tgggggaggc ttggtacaac ctggggggtc cctgagactc        60
tcctgtgcag cctctggatt cacctttagc agttatgcca tgacctgggt ccgccaggct       120
ccagggatgg gactggagtg gtctcagtt attagtggta gtggtagtga aacatactac        180
gcagactccg tgaagggccg gttcaccatc tccagagaca attccaaaaa cacactgtat       240
ctgcaaatga acagcctgag agccgaagac acggccgtat attactgtgt gaaagattct       300
tcgtatagga gctcgtcgag ggcctactac tactacggaa tggacgtctg gggcctaggg       360
accacggtca ccgtctcctc a                                                 381

<210> SEQ ID NO 506
<211> LENGTH: 127
<212> TYPE: PRT
<213> ORGANISM: Artificial Sequence
<220> FEATURE:
<223> OTHER INFORMATION: synthetic

<400> SEQUENCE: 506

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Met Gly Leu Glu Trp Val
        35                  40                  45

Ser Val Ile Ser Gly Ser Gly Ser Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Val Lys Asp Ser Ser Tyr Arg Ser Ser Arg Ala Tyr Tyr Tyr
        100                 105                 110

Gly Met Asp Val Trp Gly Leu Gly Thr Thr Val Thr Val Ser Ser
        115                 120                 125
```

<210> SEQ ID NO 507
<211> LENGTH: 24
<212> TYPE: DNA
<213> ORGANISM: Artificial Sequence
<220> FEATURE:
<223> OTHER INFORMATION: synthetic

<400> SEQUENCE: 507
ggattcacct ttagcagtta tgcc    24

<210> SEQ ID NO 508
<211> LENGTH: 8
<212> TYPE: PRT
<213> ORGANISM: Artificial Sequence
<220> FEATURE:
<223> OTHER INFORMATION: synthetic

<400> SEQUENCE: 508

```
Gly Phe Thr Phe Ser Ser Tyr Ala
1               5
```

<210> SEQ ID NO 509
<211> LENGTH: 24
<212> TYPE: DNA
<213> ORGANISM: Artificial Sequence
<220> FEATURE:
<223> OTHER INFORMATION: synthetic

<400> SEQUENCE: 509
attagtggta gtggtagtga aaca    24

<210> SEQ ID NO 510
<211> LENGTH: 8
<212> TYPE: PRT
<213> ORGANISM: Artificial Sequence
<220> FEATURE:
<223> OTHER INFORMATION: synthetic

<400> SEQUENCE: 510

```
Ile Ser Gly Ser Gly Ser Glu Thr
1               5
```

<210> SEQ ID NO 511
<211> LENGTH: 60
<212> TYPE: DNA
<213> ORGANISM: Artificial Sequence
<220> FEATURE:
<223> OTHER INFORMATION: synthetic

<400> SEQUENCE: 511
gtgaaagatt cttcgtatag gagctcgtcg agggcctact actactacgg aatggacgtc    60

<210> SEQ ID NO 512
<211> LENGTH: 20
<212> TYPE: PRT
<213> ORGANISM: Artificial Sequence
<220> FEATURE:
<223> OTHER INFORMATION: synthetic

<400> SEQUENCE: 512

Val Lys Asp Ser Ser Tyr Arg Ser Ser Arg Ala Tyr Tyr Tyr
1               5                   10                  15

Gly Met Asp Val
            20

<210> SEQ ID NO 513
<211> LENGTH: 324
<212> TYPE: DNA
<213> ORGANISM: Artificial Sequence
<220> FEATURE:
<223> OTHER INFORMATION: synthetic

<400> SEQUENCE: 513
gacatccaga tgacccagtc tccatcctcc ctgtctgcat ctgtaggaga cagagtcacc      60
atcacttgcc gggcaagtca gagcattagc agctatttaa attggtatca acagaaacca     120
gggaaagccc ctaagctcct gatctatgct gtttccattt tgcaaagtgg ggtcccatca     180
aggttcagtg gcagtggatc tgggacagat ttcactctca ccatcaactc tctgcaacct     240
gaagattttg caacttactc ctgtcaacag acttacagta cccctccgat caccttcggc     300
caagggacac gactggagat taaa                                            324

<210> SEQ ID NO 514
<211> LENGTH: 108
<212> TYPE: PRT
<213> ORGANISM: Artificial Sequence
<220> FEATURE:
<223> OTHER INFORMATION: synthetic

<400> SEQUENCE: 514

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Ile Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Ser Cys Gln Gln Thr Tyr Ser Thr Pro Pro
                85                  90                  95

Ile Thr Phe Gly Gln Gly Thr Arg Leu Glu Ile Lys
            100                 105

<210> SEQ ID NO 515
<211> LENGTH: 18
<212> TYPE: DNA
<213> ORGANISM: Artificial Sequence
<220> FEATURE:
<223> OTHER INFORMATION: synthetic

<400> SEQUENCE: 515
cagagcatta gcagctat                                                    18

<210> SEQ ID NO 516
<211> LENGTH: 6
<212> TYPE: PRT
<213> ORGANISM: Artificial Sequence
<220> FEATURE:

<223> OTHER INFORMATION: synthetic

<400> SEQUENCE: 516

Gln Ser Ile Ser Ser Tyr
1               5

<210> SEQ ID NO 517
<211> LENGTH: 9
<212> TYPE: DNA
<213> ORGANISM: Artificial Sequence
<220> FEATURE:
<223> OTHER INFORMATION: synthetic

<400> SEQUENCE: 517 gctgtttcc                                                            9

<210> SEQ ID NO 518
<211> LENGTH: 3
<212> TYPE: PRT
<213> ORGANISM: Artificial Sequence
<220> FEATURE:
<223> OTHER INFORMATION: synthetic

<400> SEQUENCE: 518

Ala Val Ser
1

<210> SEQ ID NO 519
<211> LENGTH: 30
<212> TYPE: DNA
<213> ORGANISM: Artificial Sequence
<220> FEATURE:
<223> OTHER INFORMATION: synthetic

<400> SEQUENCE: 519
caacagactt acagtacccc tccgatcacc                                    30

<210> SEQ ID NO 520
<211> LENGTH: 10
<212> TYPE: PRT
<213> ORGANISM: Artificial Sequence
<220> FEATURE:
<223> OTHER INFORMATION: synthetic

<400> SEQUENCE: 520

Gln Gln Thr Tyr Ser Thr Pro Pro Ile Thr
1               5                   10

<210> SEQ ID NO 521
<211> LENGTH: 381
<212> TYPE: DNA
<213> ORGANISM: Artificial Sequence
<220> FEATURE:
<223> OTHER INFORMATION: synthetic

<400> SEQUENCE: 521
gaggtgcagc tattggagtc agggggaggc ttggtacagc cggggggggtc cctgagactc    60 tcctgtgcag cctctggatt cacctttagt ggctatgccg tgagctgggt ccgccaggct   120
ccagggaagg ggctggagtg ggtctcaact attagtggaa gtggtactat cacacattac   180
gtagactccg tgaagggccg gttcaccatc tcccgagaca attccaagaa cacgctgtat   240
ctgcaaatga gcagcctgag agccgaggac acggccatat attactgtgc gagagacccg   300
tattacgatg tttttgactgg ttattataag gaggactact tgactactg gggccaggga   360 acctctggtca ccgtctcctc a                                    381

<210> SEQ ID NO 522
<211> LENGTH: 127
<212> TYPE: PRT
<213> ORGANISM: Artificial Sequence
<220> FEATURE:
<223> OTHER INFORMATION: synthetic

<400> SEQUENCE: 522

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Val Ser Trp Val Arg Gln Ala Pro Gly Lys Gly Leu Glu Trp Val
        35                  40                  45

Ser Thr Ile Ser Gly Ser Gly Thr Ile Thr His Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Ile Tyr Tyr Cys
                85                  90                  95

Ala Arg Asp Pro Tyr Tyr Asp Val Leu Thr Gly Tyr Tyr Lys Glu Asp
            100                 105                 110

Tyr Phe Asp Tyr Trp Gly Gln Gly Thr Leu Val Thr Val Ser Ser
        115                 120                 125

<210> SEQ ID NO 523
<211> LENGTH: 24
<212> TYPE: DNA
<213> ORGANISM: Artificial Sequence
<220> FEATURE:
<223> OTHER INFORMATION: synthetic

<400> SEQUENCE: 523
ggattcacct ttagtggcta tgcc                                  24

<210> SEQ ID NO 524
<211> LENGTH: 8
<212> TYPE: PRT
<213> ORGANISM: Artificial Sequence
<220> FEATURE:
<223> OTHER INFORMATION: synthetic

<400> SEQUENCE: 524

Gly Phe Thr Phe Ser Gly Tyr Ala
1               5

<210> SEQ ID NO 525
<211> LENGTH: 24
<212> TYPE: DNA
<213> ORGANISM: Artificial Sequence
<220> FEATURE:
<223> OTHER INFORMATION: synthetic

<400> SEQUENCE: 525
attagtggaa gtggtactat caca                                  24

<210> SEQ ID NO 526
<211> LENGTH: 8
<212> TYPE: PRT
<213> ORGANISM: Artificial Sequence
<220> FEATURE:

<223> OTHER INFORMATION: synthetic

<400> SEQUENCE: 526

Ile Ser Gly Ser Gly Thr Ile Thr
1               5

<210> SEQ ID NO 527
<211> LENGTH: 60
<212> TYPE: DNA
<213> ORGANISM: Artificial Sequence
<220> FEATURE:
<223> OTHER INFORMATION: synthetic

<400> SEQUENCE: 527
gcgagagacc cgtattacga tgttttgact ggttattata aggaggacta ctttgactac    60

<210> SEQ ID NO 528
<211> LENGTH: 20
<212> TYPE: PRT
<213> ORGANISM: Artificial Sequence
<220> FEATURE:
<223> OTHER INFORMATION: synthetic

<400> SEQUENCE: 528

Ala Arg Asp Pro Tyr Tyr Asp Val Leu Thr Gly Tyr Tyr Lys Glu Asp
1               5                   10                  15

Tyr Phe Asp Tyr
            20

<210> SEQ ID NO 529
<211> LENGTH: 324
<212> TYPE: DNA
<213> ORGANISM: Artificial Sequence
<220> FEATURE:
<223> OTHER INFORMATION: synthetic

<400> SEQUENCE: 529
gacatccaga tgacccagtc tccatcctcc ctgtctgcat ctgtaggaga cagagtcacc     60
atcacttgcc gggcaagtca gagcattagc aactatttaa attggtatca gcagaaacca    120
gggaaagccc ctaagctcct gatctatgct gcattcagct tgcaaactgg ggtcccatca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 530
<211> LENGTH: 108
<212> TYPE: PRT
<213> ORGANISM: Artificial Sequence
<220> FEATURE:
<223> OTHER INFORMATION: synthetic

<400> SEQUENCE: 530

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Phe Ser Leu Gln Thr Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105
```

<210> SEQ ID NO 531
<211> LENGTH: 18
<212> TYPE: DNA
<213> ORGANISM: Artificial Sequence
<220> FEATURE:
<223> OTHER INFORMATION: synthetic

<400> SEQUENCE: 531
cagagcatta gcaactat                                                  18

<210> SEQ ID NO 532
<211> LENGTH: 6
<212> TYPE: PRT
<213> ORGANISM: Artificial Sequence
<220> FEATURE:
<223> OTHER INFORMATION: synthetic

<400> SEQUENCE: 532

```
Gln Ser Ile Ser Asn Tyr
 1               5
```

<210> SEQ ID NO 533
<211> LENGTH: 9
<212> TYPE: DNA
<213> ORGANISM: Artificial Sequence
<220> FEATURE:
<223> OTHER INFORMATION: synthetic

<400> SEQUENCE: 533 gctgcattc                                                             9

<210> SEQ ID NO 534
<211> LENGTH: 3
<212> TYPE: PRT
<213> ORGANISM: Artificial Sequence
<220> FEATURE:
<223> OTHER INFORMATION: synthetic

<400> SEQUENCE: 534

```
Ala Ala Phe
 1
```

<210> SEQ ID NO 535
<211> LENGTH: 30
<212> TYPE: DNA
<213> ORGANISM: Artificial Sequence
<220> FEATURE:
<223> OTHER INFORMATION: synthetic

<400> SEQUENCE: 535
caacagagtt acagtacccc tccgatcacc                                     30

<210> SEQ ID NO 536
<211> LENGTH: 10
<212> TYPE: PRT
<213> ORGANISM: Artificial Sequence
<220> FEATURE:
<223> OTHER INFORMATION: synthetic

```
<400> SEQUENCE: 536

Gln Gln Ser Tyr Ser Thr Pro Pro Ile Thr
1               5                   10

<210> SEQ ID NO 537
<211> LENGTH: 98
<212> TYPE: PRT
<213> ORGANISM: Artificial Sequence
<220> FEATURE:
<223> OTHER INFORMATION: GenBank Ac. No: NP_041326.1

<400> SEQUENCE: 537

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 538
<211> LENGTH: 9
<212> TYPE: PRT
<213> ORGANISM: Artificial Sequence
<220> FEATURE:
<223> OTHER INFORMATION: HPV16E7:11-19

<400> SEQUENCE: 538

Tyr Met Leu Asp Leu Gln Pro Glu Thr
1               5

<210> SEQ ID NO 539
<211> LENGTH: 9
<212> TYPE: PRT
<213> ORGANISM: Artificial Sequence
<220> FEATURE:
<223> OTHER INFORMATION: HPV16E7:82-90

<400> SEQUENCE: 539

Leu Leu Met Gly Thr Leu Gly Ile Val
1               5

<210> SEQ ID NO 540
<211> LENGTH: 478
<212> TYPE: PRT
<213> ORGANISM: Artificial Sequence
<220> FEATURE:
<223> OTHER INFORMATION: 17364N CAR

<400> SEQUENCE: 540

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45
```

```
Tyr Ala Val Ser Ile Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Ser Cys Gln Gln Thr Tyr Ser Thr Pro Pro
                 85                  90                  95

Ile Thr Phe Gly Gln Gly Thr Arg Leu Glu Ile Lys Gly Gly Gly Gly
                100                 105                 110

Ser Gly Gly Gly Gly Ser Gly Gly Gly Ser Glu Val Gln Leu Leu
                115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Ser Tyr Ala Met Thr Trp Val
145                 150                 155                 160

Arg Gln Ala Pro Gly Lys Gly Leu Glu Trp Val Ser Val Ile Ser Gly
                165                 170                 175

Ser Gly Ser Glu Thr Tyr Tyr Ala Asp Ser Val Lys Gly Arg Phe Thr
                180                 185                 190

Ile Ser Arg Asp Asn Ser Lys Asn Thr Leu Tyr Leu Gln Met Asn Ser
            195                 200                 205

Leu Arg Ala Glu Asp Thr Ala Val Tyr Tyr Cys Val Lys Asp Ser Ser
    210                 215                 220

Tyr Arg Ser Ser Ser Arg Ala Tyr Tyr Tyr Gly Met Asp Val Trp
225                 230                 235                 240

Gly Leu Gly Thr Thr Val Thr Val Ser Ser Gly Gly Gly Ser Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
            275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Lys Arg Gly Arg Lys Lys Leu Leu Tyr Ile Phe Lys
                325                 330                 335

Gln Pro Phe Met Arg Pro Val Gln Thr Thr Gln Glu Glu Asp Gly Cys
                340                 345                 350

Ser Cys Arg Phe Pro Glu Glu Glu Gly Gly Cys Glu Leu Arg Val
                355                 360                 365

Lys Phe Ser Arg Ser Ala Asp Ala Pro Ala Tyr Lys Gln Gly Gln Asn
370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg Arg
                435                 440                 445

Gly Lys Gly His Asp Gly Leu Tyr Gln Gly Leu Ser Thr Ala Thr Lys
450                 455                 460
```

Asp Thr Tyr Asp Ala Leu His Met Gln Ala Leu Pro Pro Arg
465                 470                 475

<210> SEQ ID NO 541
<211> LENGTH: 476
<212> TYPE: PRT
<213> ORGANISM: Artificial Sequence
<220> FEATURE:
<223> OTHER INFORMATION: 17670P CAR

<400> SEQUENCE: 541

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Gly Pro Pro
            85                  90                  95

Ile Thr Phe Gly Gln Gly Thr Arg Leu Glu Ile Lys Gly Gly Gly Gly
        100                 105                 110

Ser Gly Gly Gly Gly Ser Gly Gly Gly Ser Glu Val Gln Leu Val
            115                 120                 125

Glu Ser Gly Gly Asp Leu Val Gln Pro Gly Thr Ser Leu Arg Leu Ser
130                 135                 140

Cys Glu Ala Ser Gly Phe Thr Leu Ser Phe Tyr Ala Met Tyr Trp Val
145                 150                 155                 160

Arg Gln Ala Pro Gly Lys Glu Leu Glu Leu Val Ser Gly Ile Ser Gly
            165                 170                 175

Asn Gly Glu Ser Met Phe Tyr Gly Asn Ser Val Lys Gly Arg Phe Ser
        180                 185                 190

Ile Ser Arg Asp Asn Ser Lys Asn Thr Leu Tyr Leu Gln Met Gly Ser
    195                 200                 205

Val Arg Ala Glu Asp Met Ala Val Tyr Tyr Cys Ala Arg Ala Tyr Ala
210                 215                 220

Ser Gly Asn Ser Tyr Phe Phe Tyr Gly Met Asp Val Trp Gly Gln
225                 230                 235                 240

Gly Thr Thr Val Thr Val Ser Ser Gly Gly Gly Ser Thr Thr Thr
            245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
        275                 280                 285

His Thr Arg Gly Leu Asp Phe Ala Cys Asp Ile Tyr Ile Trp Ala Pro
    290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
            325                 330                 335

Phe Met Arg Pro Val Gln Thr Thr Gln Glu Glu Asp Gly Cys Ser Cys
        340                 345                 350

```
Arg Phe Pro Glu Glu Glu Gly Gly Cys Glu Leu Arg Val Lys Phe
            355                 360                 365

Ser Arg Ser Ala Asp Ala Pro Ala Tyr Lys Gln Gly Gln Asn Gln Leu
370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 542
<211> LENGTH: 476
<212> TYPE: PRT
<213> ORGANISM: Artificial Sequence
<220> FEATURE:
<223> OTHER INFORMATION: 17675P CAR

<400> SEQUENCE: 542

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Ala Ser Leu Arg Leu Ser
130                 135                 140

Cys Glu Ala Ser Gly Phe Thr Leu Ser Phe Tyr Ala Met His Trp Val
145                 150                 155                 160

Arg Gln Ala Pro Gly Lys Glu Leu Glu Tyr Val Ser Gly Ile Ser Gly
                165                 170                 175

Asn Gly Asn Ser Ile Tyr Tyr Arg Asp Ser Val Lys Gly Arg Phe Thr
            180                 185                 190

Ile Ser Arg Asp Asn Ser Lys Asn Thr Leu Tyr Leu Gln Met Gly Ser
        195                 200                 205

Val Gly Ala Glu Asp Met Ala Val Tyr Tyr Cys Ala Arg Ser Tyr Ser
210                 215                 220

Ser Gly Asn Ser Tyr Tyr Tyr Tyr Tyr Gly Met Asp Val Trp Gly Gln
225                 230                 235                 240
```

```
Gly Thr Thr Val Thr Val Ser Ser Gly Gly Gly Ser Thr Thr Thr
                245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
            275                 280                 285

His Thr Arg Gly Leu Asp Phe Ala Cys Asp Ile Tyr Ile Trp Ala Pro
290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Gly Gly Cys Glu Leu Arg Val Lys Phe
            355                 360                 365

Ser Arg Ser Ala Asp Ala Pro Ala Tyr Lys Gln Gly Gln Asn Gln Leu
            370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 543
<211> LENGTH: 476
<212> TYPE: PRT
<213> ORGANISM: Artificial Sequence
<220> FEATURE:
<223> OTHER INFORMATION: 17930N2 CAR

<400> SEQUENCE: 543

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Gly Ser Glu Val Gln Leu Val
        115                 120                 125
```

```
Glu Ser Gly Gly Gly Leu Val Gln Pro Gly Gly Ser Leu Arg Leu Ser
            130                 135                 140

Cys Ala Ala Ser Gly Phe Thr Phe Ser Tyr Tyr Ala Leu His Trp Val
145                 150                 155                 160

Arg Gln Ala Pro Gly Lys Gly Leu Glu Tyr Val Ser Ala Ile Ser Gly
                165                 170                 175

Asn Gly Gly Ser Thr Tyr Tyr Ala Asp Ser Val Lys Gly Arg Phe Thr
                180                 185                 190

Ile Ser Arg Asp Lys Ser Met Ser Thr Val Tyr Leu Gln Val Gly Ser
                195                 200                 205

Leu Arg Ala Glu Asp Met Ala Val Tyr Tyr Cys Ala Arg Ser Tyr Ala
210                 215                 220

Ser Ser Ser Asp Tyr His Tyr Tyr Gly Met Asp Val Trp Gly Gln
225                 230                 235                 240

Gly Thr Thr Val Thr Val Ser Ser Gly Gly Gly Ser Thr Thr Thr
                245                 250                 255

Pro Ala Pro Arg Pro Pro Thr Pro Ala Pro Thr Ile Ala Ser Gln Pro
                260                 265                 270

Leu Ser Leu Arg Pro Glu Ala Cys Arg Pro Ala Ala Gly Gly Ala Val
                275                 280                 285

His Thr Arg Gly Leu Asp Phe Ala Cys Asp Ile Tyr Ile Trp Ala Pro
                290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
                340                 345                 350

Arg Phe Pro Glu Glu Glu Glu Gly Gly Cys Glu Leu Arg Val Lys Phe
                355                 360                 365

Ser Arg Ser Ala Asp Ala Pro Ala Tyr Lys Gln Gly Gln Asn Gln Leu
                370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
                420                 425                 430

Glu Ala Tyr Ser Glu Ile Gly Met Lys Gly Glu Arg Arg Arg Gly Lys
                435                 440                 445

Gly His Asp Gly Leu Tyr Gln Gly Leu Ser Thr Ala Thr Lys Asp Thr
                450                 455                 460

Tyr Asp Ala Leu His Met Gln Ala Leu Pro Pro Arg
465                 470                 475

<210> SEQ ID NO 544
<211> LENGTH: 476
<212> TYPE: PRT
<213> ORGANISM: Artificial Sequence
<220> FEATURE:
<223> OTHER INFORMATION: 21064P CAR

<400> SEQUENCE: 544

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Thr Phe Tyr Ala Met His Trp Val
145                 150                 155                 160

Arg Gln Ala Pro Gly Lys Gly Leu Glu Tyr Val Ser Gly Ile Ser Ser
                165                 170                 175

Asn Gly Gly Ser Thr Lys Tyr Ala Asp Ser Val Lys Gly Arg Phe Thr
            180                 185                 190

Ile Ser Arg Asp Asn Ser Lys Asn Thr Leu Tyr Leu Gln Met Gly Ser
        195                 200                 205

Leu Arg Ala Glu Asp Leu Ala Val Tyr Tyr Cys Ala Arg Ser Tyr Ala
    210                 215                 220

Ser Ser Ser Asp Tyr His Tyr Tyr Tyr Gly Met Asp Val Trp Gly Gln
225                 230                 235                 240

Gly Thr Thr Val Thr Val Ser Ser Gly Gly Gly Ser Thr Thr Thr
                245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
        275                 280                 285

His Thr Arg Gly Leu Asp Phe Ala Cys Asp Ile Tyr Ile Trp Ala Pro
    290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
        355                 360                 365

Ser Arg Ser Ala Asp Ala Pro Ala Tyr Lys Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys

```
                435                 440                 445
Gly His Asp Gly Leu Tyr Gln Gly Leu Ser Thr Ala Thr Lys Asp Thr
450                 455                 460

Tyr Asp Ala Leu His Met Gln Ala Leu Pro Pro Arg
465                 470                 475

<210> SEQ ID NO 545
<211> LENGTH: 478
<212> TYPE: PRT
<213> ORGANISM: Artificial Sequence
<220> FEATURE:
<223> OTHER INFORMATION: 17363N CAR

<400> SEQUENCE: 545

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Ile Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Ser Cys Gln Gln Thr Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Glu Val Gln Leu Leu
        115                 120                 125

Glu Ser Gly Gly Gly Leu Val Gln Pro Gly Gly Ser Leu Arg Leu Ser
130                 135                 140

Cys Ala Ala Ser Gly Phe Thr Phe Ser Ser Tyr Ala Met Thr Trp Val
145                 150                 155                 160

Arg Gln Ala Pro Gly Met Gly Leu Glu Trp Val Ser Val Ile Ser Gly
                165                 170                 175

Ser Gly Ser Glu Thr Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Val Lys Asp Ser Ser
    210                 215                 220

Tyr Arg Ser Ser Arg Ala Tyr Tyr Tyr Gly Met Asp Val Trp
225                 230                 235                 240

Gly Leu Gly Thr Thr Val Thr Val Ser Ser Gly Gly Gly Ser Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Lys Arg Gly Arg Lys Lys Leu Leu Tyr Ile Phe Lys
```

```
                    325                 330                 335
Gln Pro Phe Met Arg Pro Val Gln Thr Thr Gln Glu Glu Asp Gly Cys
            340                 345                 350
Ser Cys Arg Phe Pro Glu Glu Glu Gly Gly Cys Glu Leu Arg Val
            355                 360                 365
Lys Phe Ser Arg Ser Ala Asp Ala Pro Ala Tyr Lys Gln Gly Gln Asn
            370                 375                 380
Gln Leu Tyr Asn Glu Leu Asn Leu Gly Arg Arg Glu Glu Tyr Asp Val
385                 390                 395                 400
Leu Asp Lys Arg Arg Gly Arg Asp Pro Glu Met Gly Gly Lys Pro Arg
                405                 410                 415
Arg Lys Asn Pro Gln Glu Gly Leu Tyr Asn Glu Leu Gln Lys Asp Lys
            420                 425                 430
Met Ala Glu Ala Tyr Ser Glu Ile Gly Met Lys Gly Glu Arg Arg Arg
            435                 440                 445
Gly Lys Gly His Asp Gly Leu Tyr Gln Gly Leu Ser Thr Ala Thr Lys
            450                 455                 460
Asp Thr Tyr Asp Ala Leu His Met Gln Ala Leu Pro Pro Arg
465                 470                 475

<210> SEQ ID NO 546
<211> LENGTH: 9
<212> TYPE: PRT
<213> ORGANISM: Artificial Sequence
<220> FEATURE:
<223> OTHER INFORMATION: SH3GLB1:244-252

<400> SEQUENCE: 546

Tyr Met Leu Asp Leu Gln Lys Gln Leu
1               5

<210> SEQ ID NO 547
<211> LENGTH: 9
<212> TYPE: PRT
<213> ORGANISM: Artificial Sequence
<220> FEATURE:
<223> OTHER INFORMATION: CAMKK1:388-396

<400> SEQUENCE: 547

Lys Met Leu Asp Lys Asn Pro Glu Thr
1               5

<210> SEQ ID NO 548
<211> LENGTH: 9
<212> TYPE: PRT
<213> ORGANISM: Artificial Sequence
<220> FEATURE:
<223> OTHER INFORMATION: USP47:691-699

<400> SEQUENCE: 548

Tyr Met Phe Asp Leu Leu Leu Glu Thr
1               5

<210> SEQ ID NO 549
<211> LENGTH: 9
<212> TYPE: PRT
<213> ORGANISM: Artificial Sequence
<220> FEATURE:
<223> OTHER INFORMATION: CHPF:463:471

<400> SEQUENCE: 549

Tyr Thr Leu Asp Leu Gln Leu Glu Ala
```

```
1               5

<210> SEQ ID NO 550
<211> LENGTH: 9
<212> TYPE: PRT
<213> ORGANISM: Artificial Sequence
<220> FEATURE:
<223> OTHER INFORMATION: PKD1:2694-2702

<400> SEQUENCE: 550

Met Met Leu Ile Leu Gln Ala Glu Thr
1               5

<210> SEQ ID NO 551
<211> LENGTH: 9
<212> TYPE: PRT
<213> ORGANISM: Artificial Sequence
<220> FEATURE:
<223> OTHER INFORMATION: NBR1:357-365

<400> SEQUENCE: 551

Leu Met Leu Pro Leu Gln Pro Cys Thr
1               5

<210> SEQ ID NO 552
<211> LENGTH: 9
<212> TYPE: PRT
<213> ORGANISM: Artificial Sequence
<220> FEATURE:
<223> OTHER INFORMATION: CBL:83-91

<400> SEQUENCE: 552

Tyr Ile Leu Asp Leu Leu Pro Asp Thr
1               5

<210> SEQ ID NO 553
<211> LENGTH: 9
<212> TYPE: PRT
<213> ORGANISM: Artificial Sequence
<220> FEATURE:
<223> OTHER INFORMATION: PPP4R4:20-28

<400> SEQUENCE: 553

Tyr Met Glu Asp Leu Gln Glu Leu Thr
1               5

<210> SEQ ID NO 554
<211> LENGTH: 9
<212> TYPE: PRT
<213> ORGANISM: Artificial Sequence
<220> FEATURE:
<223> OTHER INFORMATION: SBK3:285-293

<400> SEQUENCE: 554

Gly Leu Leu Asp Leu Asp Pro Glu Thr
1               5

<210> SEQ ID NO 555
<211> LENGTH: 9
<212> TYPE: PRT
<213> ORGANISM: Artificial Sequence
<220> FEATURE:
<223> OTHER INFORMATION: FNDC3B:921-929

<400> SEQUENCE: 555

Val Met Lys Asp Leu Leu Pro Glu Thr
1               5
```

<210> SEQ ID NO 556
<211> LENGTH: 9
<212> TYPE: PRT
<213> ORGANISM: Artificial Sequence
<220> FEATURE:
<223> OTHER INFORMATION: VPREB3:9-17

<400> SEQUENCE: 556

Leu Leu Met Gly Thr Phe Leu Ser Val
1               5

<210> SEQ ID NO 557
<211> LENGTH: 9
<212> TYPE: PRT
<213> ORGANISM: Artificial Sequence
<220> FEATURE:
<223> OTHER INFORMATION: B4GALT2:4-12

<400> SEQUENCE: 557

Leu Leu Gly Gly Thr Leu Glu Arg Val
1               5

<210> SEQ ID NO 558
<211> LENGTH: 9
<212> TYPE: PRT
<213> ORGANISM: Artificial Sequence
<220> FEATURE:
<223> OTHER INFORMATION: GCAT:312-320

<400> SEQUENCE: 558

Leu Leu Met Gly Ser Asn Thr Ile Val
1               5

<210> SEQ ID NO 559
<211> LENGTH: 9
<212> TYPE: PRT
<213> ORGANISM: Artificial Sequence
<220> FEATURE:
<223> OTHER INFORMATION: CYP39A1:246-254

<400> SEQUENCE: 559

Leu Leu Gln Ala Thr Leu Asp Ile Val
1               5

<210> SEQ ID NO 560
<211> LENGTH: 9
<212> TYPE: PRT
<213> ORGANISM: Artificial Sequence
<220> FEATURE:
<223> OTHER INFORMATION: ALDH3A2:467-475

<400> SEQUENCE: 560

Leu Leu Leu Thr Phe Leu Gly Ile Val
1               5

<210> SEQ ID NO 561
<211> LENGTH: 9
<212> TYPE: PRT
<213> ORGANISM: Artificial Sequence
<220> FEATURE:
<223> OTHER INFORMATION: CLCN4:79-87

<400> SEQUENCE: 561

Leu Leu Ala Gly Thr Leu Ala Gly Val
1               5

<210> SEQ ID NO 562
<211> LENGTH: 9
<212> TYPE: PRT
<213> ORGANISM: Artificial Sequence
<220> FEATURE:
<223> OTHER INFORMATION: ZHX2:234-242

<400> SEQUENCE: 562

Leu Leu Gln Asp Thr Leu Gly His Val
1               5

<210> SEQ ID NO 563
<211> LENGTH: 9
<212> TYPE: PRT
<213> ORGANISM: Artificial Sequence
<220> FEATURE:
<223> OTHER INFORMATION: GRM6:590-598

<400> SEQUENCE: 563

Leu Leu Leu Ala Val Leu Gly Ile Val
1               5

<210> SEQ ID NO 564
<211> LENGTH: 9
<212> TYPE: PRT
<213> ORGANISM: Artificial Sequence
<220> FEATURE:
<223> OTHER INFORMATION: IPO9:582-590

<400> SEQUENCE: 564

Leu Val Met Glu Thr Leu Cys Ile Val
1               5

<210> SEQ ID NO 565
<211> LENGTH: 9
<212> TYPE: PRT
<213> ORGANISM: Artificial Sequence
<220> FEATURE:
<223> OTHER INFORMATION: IPO4:163-171

<400> SEQUENCE: 565

Leu Leu Asn Glu Thr Leu Gly Glu Val
1               5

<210> SEQ ID NO 566
<211> LENGTH: 9
<212> TYPE: PRT
<213> ORGANISM: Artificial Sequence
<220> FEATURE:
<223> OTHER INFORMATION: SF3B1:969-977

<400> SEQUENCE: 566

Lys Leu Met Gly His Leu Gly Val Val
1               5

<210> SEQ ID NO 567
<211> LENGTH: 9
<212> TYPE: PRT
<213> ORGANISM: Artificial Sequence
<220> FEATURE:
<223> OTHER INFORMATION: DOCK11:1282-1290

<400> SEQUENCE: 567

Leu Leu Met Cys Tyr Leu Tyr Ile Val
1               5

```
<210> SEQ ID NO 568
<211> LENGTH: 9
<212> TYPE: PRT
<213> ORGANISM: Artificial Sequence
<220> FEATURE:
<223> OTHER INFORMATION: hCNOT1:1962-1970

<400> SEQUENCE: 568

Leu Leu Asn Lys Val Leu Gly Ile Val
1               5

<210> SEQ ID NO 569
<211> LENGTH: 9
<212> TYPE: PRT
<213> ORGANISM: Artificial Sequence
<220> FEATURE:
<223> OTHER INFORMATION: synthetic

<400> SEQUENCE: 569

Ala Met Leu Asp Leu Gln Pro Glu Thr
1               5

<210> SEQ ID NO 570
<211> LENGTH: 9
<212> TYPE: PRT
<213> ORGANISM: Artificial Sequence
<220> FEATURE:
<223> OTHER INFORMATION: synthetic

<400> SEQUENCE: 570

Tyr Ala Leu Asp Leu Gln Pro Glu Thr
1               5

<210> SEQ ID NO 571
<211> LENGTH: 9
<212> TYPE: PRT
<213> ORGANISM: Artificial Sequence
<220> FEATURE:
<223> OTHER INFORMATION: synthetic

<400> SEQUENCE: 571

Tyr Met Ala Asp Leu Gln Pro Glu Thr
1               5

<210> SEQ ID NO 572
<211> LENGTH: 9
<212> TYPE: PRT
<213> ORGANISM: Artificial Sequence
<220> FEATURE:
<223> OTHER INFORMATION: synthetic

<400> SEQUENCE: 572

Tyr Met Leu Ala Leu Gln Pro Glu Thr
1               5

<210> SEQ ID NO 573
<211> LENGTH: 9
<212> TYPE: PRT
<213> ORGANISM: Artificial Sequence
<220> FEATURE:
<223> OTHER INFORMATION: synthetic

<400> SEQUENCE: 573

Tyr Met Leu Asp Ala Gln Pro Glu Thr
1               5

<210> SEQ ID NO 574
```

<210> SEQ ID NO 574
<211> LENGTH: 9
<212> TYPE: PRT
<213> ORGANISM: Artificial Sequence
<220> FEATURE:
<223> OTHER INFORMATION: synthetic

<400> SEQUENCE: 574

Tyr Met Leu Asp Leu Ala Pro Glu Thr
1               5

<210> SEQ ID NO 575
<211> LENGTH: 9
<212> TYPE: PRT
<213> ORGANISM: Artificial Sequence
<220> FEATURE:
<223> OTHER INFORMATION: synthetic

<400> SEQUENCE: 575

Tyr Met Leu Asp Leu Gln Ala Glu Thr
1               5

<210> SEQ ID NO 576
<211> LENGTH: 9
<212> TYPE: PRT
<213> ORGANISM: Artificial Sequence
<220> FEATURE:
<223> OTHER INFORMATION: synthetic

<400> SEQUENCE: 576

Tyr Met Leu Asp Leu Gln Pro Ala Thr
1               5

<210> SEQ ID NO 577
<211> LENGTH: 9
<212> TYPE: PRT
<213> ORGANISM: Artificial Sequence
<220> FEATURE:
<223> OTHER INFORMATION: synthetic

<400> SEQUENCE: 577

Tyr Met Leu Asp Leu Gln Pro Glu Ala
1               5

<210> SEQ ID NO 578
<211> LENGTH: 453
<212> TYPE: PRT
<213> ORGANISM: Artificial Sequence
<220> FEATURE:
<223> OTHER INFORMATION: HC 17363N

<400> SEQUENCE: 578

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Thr Trp Val Arg Gln Ala Pro Gly Met Gly Leu Glu Trp Val
            35                  40                  45

Ser Val Ile Ser Gly Ser Gly Ser Glu Thr Tyr Tyr Ala Asp Ser Val
        50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Ser Ser Tyr Arg Ser Ser Ser Arg Ala Tyr Tyr Tyr Tyr

```
            100                 105                 110
Gly Met Asp Val Trp Gly Leu Gly Thr Thr Val Thr Val Ser Ser Ala
        115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 579
<211> LENGTH: 215
<212> TYPE: PRT
<213> ORGANISM: Artificial Sequence
<220> FEATURE:
<223> OTHER INFORMATION: LC 17363N

<400> SEQUENCE: 579

Asp Ile Gln Met Thr Gln Ser Pro Ser Ser Leu Ser Ala Ser Val Gly
```

```
              1               5                  10                 15
Asp Arg Val Thr Ile Thr Cys Arg Ala Ser Gln Ser Ile Ser Ser Tyr
                20                  25                 30

Leu Asn Trp Tyr Gln Gln Lys Pro Gly Lys Ala Pro Lys Leu Leu Ile
                35                  40                 45

Tyr Ala Val Ser Ile Leu Gln Ser Gly Val Pro Ser Arg Phe Ser Gly
                50                  55                 60

Ser Gly Ser Gly Thr Asp Phe Thr Leu Thr Ile Asn Ser Leu Gln Pro
 65                 70                  75                 80

Glu Asp Phe Ala Thr Tyr Ser Cys Gln Gln Thr Tyr Ser Thr Pro Pro
                85                  90                 95

Ile Thr Phe Gly Gln Gly Thr Arg Leu Glu Ile Lys Arg Thr Val Ala
                100                 105                110

Ala Pro Ser Val Phe Ile Phe Pro Pro Ser Asp Glu Gln Leu Lys Ser
                115                 120                125

Gly Thr Ala Ser Val Val Cys Leu Leu Asn Asn Phe Tyr Pro Arg Glu
                130                 135                140

Ala Lys Val Gln Trp Lys Val Asp Asn Ala Leu Gln Ser Gly Asn Ser
145                 150                 155                160

Gln Glu Ser Val Thr Glu Gln Asp Ser Lys Asp Ser Thr Tyr Ser Leu
                165                 170                175

Ser Ser Thr Leu Thr Leu Ser Lys Ala Asp Tyr Glu Lys His Lys Val
                180                 185                190

Tyr Ala Cys Glu Val Thr His Gln Gly Leu Ser Ser Pro Val Thr Lys
                195                 200                205

Ser Phe Asn Arg Gly Glu Cys
                210                 215

<210> SEQ ID NO 580
<211> LENGTH: 453
<212> TYPE: PRT
<213> ORGANISM: Artificial Sequence
<220> FEATURE:
<223> OTHER INFORMATION: HC 17364N

<400> SEQUENCE: 580

Glu Val Gln Leu Leu Glu Ser Gly Gly Gly Leu Val Gln Pro Gly Gly
1               5                   10                 15

Ser Leu Arg Leu Ser Cys Ala Ala Ser Gly Phe Thr Phe Ser Ser Tyr
                20                  25                 30

Ala Met Thr Trp Val Arg Gln Ala Pro Gly Lys Gly Leu Glu Trp Val
                35                  40                 45

Ser Val Ile Ser Gly Ser Gly Ser Glu Thr Tyr Tyr Ala Asp Ser Val
                50                  55                 60

Lys Gly Arg Phe Thr Ile Ser Arg Asp Asn Ser Lys Asn Thr Leu Tyr
 65                 70                  75                 80

Leu Gln Met Asn Ser Leu Arg Ala Glu Asp Thr Ala Val Tyr Tyr Cys
                85                  90                 95

Val Lys Asp Ser Ser Tyr Arg Ser Ser Ser Arg Ala Tyr Tyr Tyr Tyr
                100                 105                110

Gly Met Asp Val Trp Gly Leu Gly Thr Thr Val Thr Val Ser Ser Ala
                115                 120                125

Ser Thr Lys Gly Pro Ser Val Phe Pro Leu Ala Pro Cys Ser Arg Ser
                130                 135                140

Thr Ser Glu Ser Thr Ala Ala Leu Gly Cys Leu Val Lys Asp Tyr Phe
```

| | | | | 145 | | | | 150 | | | | 155 | | | | 160 |

Pro Glu Pro Val Thr Val Ser Trp Asn Ser Gly Ala Leu Thr Ser Gly
                        165                  170                  175

Val His Thr Phe Pro Ala Val Leu Gln Ser Ser Gly Leu Tyr Ser Leu
            180                  185                  190

Ser Ser Val Val Thr Val Pro Ser Ser Ser Leu Gly Thr Lys Thr Tyr
        195                  200                  205

Thr Cys Asn Val Asp His Lys Pro Ser Asn Thr Lys Val Asp Lys Arg
   210                  215                  220

Val Glu Ser Lys Tyr Gly Pro Pro Cys Pro Cys Pro Ala Pro Pro
225               230                  235                  240

Val Ala Gly Pro Ser Val Phe Leu Phe Pro Lys Pro Lys Asp Thr
            245                  250                  255

Leu Met Ile Ser Arg Thr Pro Glu Val Thr Cys Val Val Asp Val
        260                  265                  270

Ser Gln Glu Asp Pro Glu Val Gln Phe Asn Trp Tyr Val Asp Gly Val
        275                  280                  285

Glu Val His Asn Ala Lys Thr Lys Pro Arg Glu Glu Gln Phe Asn Ser
   290                  295                  300

Thr Tyr Arg Val Val Ser Val Leu Thr Val Leu His Gln Asp Trp Leu
305               310                  315                  320

Asn Gly Lys Glu Tyr Lys Cys Lys Val Ser Asn Lys Gly Leu Pro Ser
            325                  330                  335

Ser Ile Glu Lys Thr Ile Ser Lys Ala Lys Gly Gln Pro Arg Glu Pro
        340                  345                  350

Gln Val Tyr Thr Leu Pro Pro Ser Gln Glu Glu Met Thr Lys Asn Gln
        355                  360                  365

Val Ser Leu Thr Cys Leu Val Lys Gly Phe Tyr Pro Ser Asp Ile Ala
   370                  375                  380

Val Glu Trp Glu Ser Asn Gly Gln Pro Glu Asn Asn Tyr Lys Thr Thr
385               390                  395                  400

Pro Pro Val Leu Asp Ser Asp Gly Ser Phe Phe Leu Tyr Ser Arg Leu
        405                  410                  415

Thr Val Asp Lys Ser Arg Trp Gln Glu Gly Asn Val Phe Ser Cys Ser
            420                  425                  430

Val Met His Glu Ala Leu His Asn His Tyr Thr Gln Lys Ser Leu Ser
            435                  440                  445

Leu Ser Leu Gly Lys
        450

<210> SEQ ID NO 581
<211> LENGTH: 215
<212> TYPE: PRT
<213> ORGANISM: Artificial Sequence
<220> FEATURE:
<223> OTHER INFORMATION: LC 17364N

<400> SEQUENCE: 581

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Ile Leu Gln Ser Gly Val Pro Ser Arg Phe Ser Gly

```
                 50                  55                  60
Ser Gly Ser Gly Thr Asp Phe Thr Leu Thr Ile Ser Ser Leu Gln Pro
 65                  70                  75                  80

Glu Asp Phe Ala Thr Tyr Ser Cys Gln Gln Thr Tyr Ser Thr Pro Pro
                 85                  90                  95

Ile Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215

<210> SEQ ID NO 582
<211> LENGTH: 451
<212> TYPE: PRT
<213> ORGANISM: Artificial Sequence
<220> FEATURE:
<223> OTHER INFORMATION: HC 17670P

<400> SEQUENCE: 582

Glu Val Gln Leu Val Glu Ser Gly Gly Asp Leu Val Gln Pro Gly Thr
 1               5                  10                  15

Ser Leu Arg Leu Ser Cys Glu Ala Ser Gly Phe Thr Leu Ser Phe Tyr
                20                  25                  30

Ala Met Tyr Trp Val Arg Gln Ala Pro Gly Lys Glu Leu Glu Leu Val
                35                  40                  45

Ser Gly Ile Ser Gly Asn Gly Glu Ser Met Phe Tyr Gly Asn Ser Val
 50                  55                  60

Lys Gly Arg Phe Ser Ile Ser Arg Asp Asn Ser Lys Asn Thr Leu Tyr
 65                  70                  75                  80

Leu Gln Met Gly Ser Val Arg Ala Glu Asp Met Ala Val Tyr Tyr Cys
                85                  90                  95

Ala Arg Ala Tyr Ala Ser Gly Asn Ser Tyr Phe Phe Tyr Tyr Gly Met
                100                 105                 110

Asp Val Trp Gly Gln Gly Thr Thr Val Thr Val Ser Ser Ala Ser Thr
                115                 120                 125

Lys Gly Pro Ser Val Phe Pro Leu Ala Pro Cys Ser Arg Ser Thr Ser
                130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
```

195                 200                 205
Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 583
<211> LENGTH: 215
<212> TYPE: PRT
<213> ORGANISM: Artificial Sequence
<220> FEATURE:
<223> OTHER INFORMATION: LC 17670P

<400> SEQUENCE: 583

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Gly Pro Pro
                85                  90                  95

Ile Thr Phe Gly Gln Gly Thr Arg Leu Glu Ile Lys Arg Thr Val Ala

```
                  100                 105                 110
Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 584
<211> LENGTH: 451
<212> TYPE: PRT
<213> ORGANISM: Artificial Sequence
<220> FEATURE:
<223> OTHER INFORMATION: HC 17675P

<400> SEQUENCE: 584

Glu Val Gln Leu Val Glu Ser Gly Gly Gly Leu Val Gln Pro Gly Ala
1               5                   10                  15

Ser Leu Arg Leu Ser Cys Glu Ala Ser Gly Phe Thr Leu Ser Phe Tyr
            20                  25                  30

Ala Met His Trp Val Arg Gln Ala Pro Gly Lys Glu Leu Glu Tyr Val
        35                  40                  45

Ser Gly Ile Ser Gly Asn Gly Asn Ser Ile Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Val Gly Ala Glu Asp Met Ala Val Tyr Tyr Cys
                85                  90                  95

Ala Arg Ser Tyr Ser Ser Gly Asn Ser Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Pro Val Ala
225                 230                 235                 240

Gly Pro Ser Val Phe Leu Phe Pro Pro Lys Pro Lys Asp Thr Leu Met
```

-continued

```
                245                 250                 255
Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 585
<211> LENGTH: 215
<212> TYPE: PRT
<213> ORGANISM: Artificial Sequence
<220> FEATURE:
<223> OTHER INFORMATION: LC 17675P

<400> SEQUENCE: 585

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
```

```
145                 150                 155                 160
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 586
<211> LENGTH: 451
<212> TYPE: PRT
<213> ORGANISM: Artificial Sequence
<220> FEATURE:
<223> OTHER INFORMATION: HC 17930N2

<400> SEQUENCE: 586

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Leu His Trp Val Arg Gln Ala Pro Gly Lys Gly Leu Glu Tyr Val
        35                  40                  45

Ser Ala Ile Ser Gly Asn Gly Gly Ser Thr Tyr Tyr Ala Asp Ser Val
    50                  55                  60

Lys Gly Arg Phe Thr Ile Ser Arg Asp Lys Ser Met Ser Thr Val Tyr
65                  70                  75                  80

Leu Gln Val Gly Ser Leu Arg Ala Glu Asp Met Ala Val Tyr Tyr Cys
                85                  90                  95

Ala Arg Ser Tyr Ala Ser Ser Asp Tyr His Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
```

290                 295                 300
Arg Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Lys
    450

<210> SEQ ID NO 587
<211> LENGTH: 214
<212> TYPE: PRT
<213> ORGANISM: Artificial Sequence
<220> FEATURE:
<223> OTHER INFORMATION: LC 17930N2

<400> SEQUENCE: 587

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser 195                 200                 205

Phe Asn Arg Gly Glu Cys
    210

<210> SEQ ID NO 588
<211> LENGTH: 450
<212> TYPE: PRT
<213> ORGANISM: Artificial Sequence
<220> FEATURE:
<223> OTHER INFORMATION: HC 21058P

<400> SEQUENCE: 588

Glu Val Gln Leu Val Glu Ser Gly Gly Asn Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Asp Ser Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Ala Gly Ile Val Val Asp Trp Asn Tyr Ala Gly Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr

```
                 340                 345                 350
Thr Leu Pro Pro Ser Gln Glu Glu Met Thr Lys Asn Gln Val Ser Leu
             355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 589
<211> LENGTH: 215
<212> TYPE: PRT
<213> ORGANISM: Artificial Sequence
<220> FEATURE:
<223> OTHER INFORMATION: LC 21058P

<400> SEQUENCE: 589

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 590
<211> LENGTH: 451
<212> TYPE: PRT
```

<213> ORGANISM: Artificial Sequence
<220> FEATURE:
<223> OTHER INFORMATION: HC 21064P

<400> SEQUENCE: 590

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Phe Tyr
            20                  25                  30

Ala Met His Trp Val Arg Gln Ala Pro Gly Lys Gly Leu Glu Tyr Val
        35                  40                  45

Ser Gly Ile Ser Ser Asn Gly Gly Ser Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Leu Ala Val Tyr Tyr Cys
                85                  90                  95

Ala Arg Ser Tyr Ala Ser Ser Asp Tyr His Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro

```
                385                 390                 395                 400
Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Lys
    450

<210> SEQ ID NO 591
<211> LENGTH: 214
<212> TYPE: PRT
<213> ORGANISM: Artificial Sequence
<220> FEATURE:
<223> OTHER INFORMATION: LC 21064P

<400> SEQUENCE: 591

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 592
<211> LENGTH: 452
<212> TYPE: PRT
<213> ORGANISM: Artificial Sequence
<220> FEATURE:
<223> OTHER INFORMATION: HC 21104P

<400> SEQUENCE: 592

Gln Val Gln Leu Val Glu Ser Gly Gly Gly Leu Val Lys Pro Gly Gly
1               5                   10                  15
```

```
Ser Leu Arg Leu Ser Cys Thr Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Leu Gly Ile Phe Leu Trp Phe Gly Glu Leu Phe Leu Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
```

```
                435             440             445
Ser Leu Gly Lys
    450

<210> SEQ ID NO 593
<211> LENGTH: 215
<212> TYPE: PRT
<213> ORGANISM: Artificial Sequence
<220> FEATURE:
<223> OTHER INFORMATION: LC 21104P

<400> SEQUENCE: 593

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```